(12) United States Patent
Marasco

(10) Patent No.: US 10,556,956 B2
(45) Date of Patent: Feb. 11, 2020

(54) PHARMACEUTICAL COMPOSITIONS COMPRISING HUMANIZED ANTI-CCR4 IGG4 ANTIBODY

(71) Applicant: Dana-Farber Cancer Institute, Inc., Boston, MA (US)

(72) Inventor: Wayne A. Marasco, Wellesley, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 15/571,202

(22) PCT Filed: Apr. 6, 2016

(86) PCT No.: PCT/US2016/026232
§ 371 (c)(1),
(2) Date: Nov. 1, 2017

(87) PCT Pub. No.: WO2016/178779
PCT Pub. Date: Nov. 10, 2016

(65) Prior Publication Data
US 2018/0265587 A1 Sep. 20, 2018

Related U.S. Application Data

(60) Provisional application No. 62/237,942, filed on Oct. 6, 2015, provisional application No. 62/217,419, filed on Sep. 11, 2015, provisional application No. 62/155,966, filed on May 1, 2015.

(51) Int. Cl.
| | |
|---|---|
| *C07K 16/28* | (2006.01) |
| *A61P 35/00* | (2006.01) |
| *A61K 39/00* | (2006.01) |
| *A61K 39/395* | (2006.01) |

(52) U.S. Cl.
CPC ...... *C07K 16/2866* (2013.01); *A61K 39/0011* (2013.01); *A61K 39/39541* (2013.01); *A61P 35/00* (2018.01); *A61K 2039/505* (2013.01); *C07K 2317/24* (2013.01); *C07K 2317/31* (2013.01); *C07K 2317/52* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,485,045 A | 11/1984 | Regen | |
| 4,522,811 A | 6/1985 | Eppstein et al. | |
| 4,544,545 A | 10/1985 | Ryan et al. | |
| 4,676,980 A | 6/1987 | Segal et al. | |
| 4,816,567 A | 3/1989 | Cabilly et al. | |
| 4,946,778 A | 8/1990 | Ladner et al. | |
| 5,013,556 A | 5/1991 | Woodle et al. | |
| 5,030,719 A | 7/1991 | Umemoto et al. | |
| 5,091,513 A | 2/1992 | Huston et al. | |
| 5,132,405 A | 7/1992 | Huston et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,916,771 A | 6/1999 | Hori et al. | |
| 5,939,598 A | 8/1999 | Kucherlapati et al. | |

FOREIGN PATENT DOCUMENTS

| | | |
|---|---|---|
| WO | 1991/00360 | 1/1991 |
| WO | 1992/020373 | 11/1992 |
| WO | 1994/002602 | 2/1994 |
| WO | 1994/011026 | 5/1994 |
| WO | 1995/022618 | 8/1995 |
| WO | 1996/033735 | 10/1996 |
| WO | 1996/034096 | 10/1996 |
| WO | 1999/053049 | 10/1999 |
| WO | 2009/086514 | 7/2009 |
| WO | WO 2009/086514 A1 | 7/2009 |
| WO | 2013/166500 | 11/2013 |
| WO | WO 2013/166500 A1 | 11/2013 |
| WO | 2016/057488 | 4/2016 |

OTHER PUBLICATIONS

Stockinger et al., CD4+ memory T cells: functional heterogeneity and homeostasis. Immunol. Rev., 211, 39-48, 2006. (Year: 2006).*

Chang D. et al., "Humanization of an Anti-CCR4 Antibody That Kills Cutaneous T-Cell Lymphoma Cells and Abrogates Suppression by T-Regulatory Cells", Molecular Cancer Therapeutics, vol. 11, No. 11, 2012, pp. 2451-2461.

Hagemann U. et al. "Fully Human Antagonistic Antibodies against CCR4 Potently Inhibit Cell Signaling and Chemotaxis", PLOSONE, vol. 9, No. 7, 2014, pp. 1-22.

Ni, X. et al. "Reduction of regulatory T cells by Mogamulizumab, a defucosylated anti-CC chemokine receptor 4 antibody, in patients with aggressive/refractory mycosis fungoides and Sezary syndrome", Clinical Cancer Research, vol. 21, No. 2, 2015, pp. 274-285.

Sugiyama D. et al. "Anti-CCR4 mAb selectively depletes effector-type FoxP3+CD4+ regulatory T cells, evoking antitumor immune responses in humans", Proceedings of the National Academy of Sciences, vol. 110, No. 44, 2013, pp. 17945-17950.

(Continued)

*Primary Examiner* — Elly-Gerald Stoica

(74) *Attorney, Agent, or Firm* — Baker Donelson

(57) ABSTRACT

The present disclosure provides methods of modulating regulatory T-cell activity and function.

4 Claims, 22 Drawing Sheets

Specification includes a Sequence Listing.

(56) References Cited

OTHER PUBLICATIONS

Lim, F., et al, in DNA Cloning: Mammalian Systems, D. Glover, Ed. (Oxford Univ. Press, Oxford England) (1995).
Lindqvist CA, Christiansson LH, Simonsson B, Enblad G, Olsson-Stromberg U, Loskog AS. T regulatory cells control T-cell proliferation partly by the release of soluble CD25 in patients with B-cell malignancies. Immunology 2010;131 (3):371-6.
Liyanage UK, Moore TT, Joo HG, Tanaka Y, Herrmann V, Doherty G, et al.Prevalence of regulatory T cells is increased in peripheral blood and tumor microenvironment of patients with pancreas or breast adenocarcinoma. Journal of immunology 2002;169(5):2756-61.
Lo AS-Y, Xu C, Murakami A, Marasco WA. Regression of established renal cell carcinoma in nude mice using lentivirus-transduced human T cells expressing a human anti-CAIX chimeric antigen receptor. Molecular Therapy—Oncolytics 2014; 1: 14003.
Lonberg and Huszar, Intern. Rev. Immunol. 13 65-93(1995).
Lonberg et al, Nature 368 856-859 (1994).
Mackensen A, Meidenbauer N, Vogl S, Laumer M, Berger J, Andreesen R. Phase I study of adoptive T-cell therapy using antigen-specific CD 8+ T cells for the treatment of patients with metastatic melanoma. Journal of clinical oncology : official journal of the American Society of Clinical Oncology 2006;24(31):5060-9.
Malmqvist, Magnus. "Biospecific interaction analysis using biosensor technology." Nature 361.6408 (1993): 186-187.
Marks et al, Bio/Technology 10, 779-783 (1992).
Marks et al, J. Mol. Biol, 222:581 (1991).
Martin et al, J. Biol. Chem, 257: 286-288 (1982).
Moon EK, Wang LC, Dolfi DV, Wilson CB, Ranganathan R, Sun J, et al. Multifactorial T-cell hypofunction that is reversible can limit the efficacy of chimeric antigen receptor-transduced human T cells in solid tumors. Clinical cancer research : an official journal of the American Association for Cancer Research 2014;20(16):4262-73.
Morrison et al., Am. J. Physiol. 266:292-305 (1994).
Morrison, Nature 368, 812-13 (1994).
Morse MA, Hobeika AC, Osada T, Serra D, Niedzwiecki D, Lyerly HK, et al.Depletion of human regulatory T cells specifically enhances antigen-specific immune responses to cancer vaccines. Blood 2008;112(3):610-8.
Mortier E, Bernard J, Plet A, Jacques Y. Natural, proteolytic release of a soluble form of human IL-15 receptor alpha-chain that behaves as a specific, high affinity IL-15 antagonist. J Immunol 2004;173(3): 1681-8.
Munson, Peter J., and David Rodbard. "Ligand: a versatile computerized approach for characterization of ligand-binding systems." Analytical biochemistry 107.1 (1980): 220-239.
Nakagawa M, Schmitz R, Xiao W, Goldman CK, Xu W, Yang Y, et al. Gain-of-function CCR4 mutations in adult T cell leukemia/lymphoma. The Journal of experimental medicine 2014;211(13):2497-505.
Neuberger, Nature Biotechnology 14, 826 (1996).
Preston CC, Maurer MJ, Oberg AL, Visscher DW, Kalli KR, Hartmann LC, et al. The ratios of CD8+ T cells to CD4+CD25+ FOXP3+ and FOXP3-T cells correlate with poor clinical outcome in human serous ovarian cancer. PloS one 2013;8(I ):e80063.
Ramakrishnan, S. et al, Cancer Res. 44:201-208 (1984).
Richardson JH, Sodroski JG, Waldmann TA, Marasco WA. Phenotypic knockout of the high-affinity human interleukin 2 receptor by intracellular single-chain antibodies against the alpha subunit of the receptor. Proceedings of the National Academy of Sciences of the United States of America 1995;92(8):3137-41.
Ridgway et al, Protein Eng 7:617-621 (1996).
Sakaguchi S, Yamaguchi T, Nomura T, Ono M. Regulatory T cells and immune tolerance. Cell 2008;133(5):775-87.
Santulli-Marotto S, Boakye K, Lacy E, Wu SJ, Luongo J, Kavalkovich K, et al. Engagement of two distinct binding domains on CCL17 is required for signaling through CCR4 and establishment of localized inflammatory conditions in the lung. PloS one 2013;8(12):e81465.
Severson JJ, Serracino HS, Mateescu V, Raeburn CD, McIntyre RC, Sams SB, et al. Pd-I+Tim-3+ CD8+ T Lymphocytes Display Varied Degrees of Functional Exhaustion in Patients with Regionally Metastatic Differentiated Thyroid Cancer. Cancer immunology research 2015.
Sheu BC, Hsu SM, Ho HN, Lien HC, Huang SC, Lin RH. A novel role of metalloproteinase in cancer-mediated immunosuppression. Cancer Res 2001;61(I):237-42.
Shopes, J. Immunol, 148: 2918-2922 (1992).
Simpson TR, Li F, Montalvo-Ortiz W, Sepulveda MA, Bergerhoff K, Arce F, et al. Fc-dependent depletion of tumor-infiltrating regulatory T cells co-defines the efficacy of anti-CTLA-4 therapy against melanoma. The Journal of experimental medicine2013;210(9): 1695-710.
Soares KC, Rucki AA, Wu AA, Olino K, Xiao Q, Chai Y, et al. PD-1/Pd-L1 blockade together with vaccine therapy facilitates effector T-cell infiltration into pancreatic tumors. Journal of immunotherapy 2015;38(1): 1-11.
Stevenson et al, Anti-Cancer Drug Design, 3: 219-230 (1989).
Valzasina B, Piconese S, Guiducci C, Colombo MP. Tumor-induced expansion of regulatory T cells by conversion of CD4+CD25-lymphocytes is thymus and proliferation independent. Cancer research 2006;66(8):4488-95.
Van der Neut Kolfschoten, M. et al., 2007, Science 317: 1554-1557.
Vignali DA, Collison LW, Workman CJ. How regulatory T cells work. Nat Rev Immunol 2008;8(7):523-32.
Viney JM, Andrew DP, Phillips RM, Meiser A, Patel P, Lennartz-Walker M, et al. Distinct conformations of the chemokine receptor CCR4 with implications for its targeting in allergy. Journal of immunology 2014;192(7):3419-27.
Vitetta et al., Science 238: 1098 (1987).
Wilkinson, D. (The Scientist, published by The Scientist, Inc., Philadelphia PA, vol. 14, No. 8 (Apr. 17, 2000), pp. 25-28).
Wolchok JD, Kluger H, Callahan MK, Postow MA, Rizvi NA, Lesokhin AM, et al. Nivolumab plus ipilimumab in advanced melanoma. The New England journal of medicine 2013;369(2): 122-33.
Wolf D, Wolf AM, Rumpold H, Fiegl H, Zeimet AG, Muller-Holzner E, et al. The expression of the regulatory T cell-specific forkhead box transcription factor FoxP3 is associated with poor prognosis in ovarian cancer. Clinical cancer research : an official journal of the American Association for Cancer Research 2005; 11 (23): 8326-31.
Woo EY, Chu CS, Goletz TJ, Schlienger K, Yeh H, Coukos G, et al. Regulatory CD4(+)CD25(+) T cells in tumors from patients with early-stage non-small cell lung cancer and late-stage ovarian cancer. Cancer research 2001;61 (12):4766-72.
Yang, et al, J. Virol. 69:2004 (1995).
Zebedee et al, Proc. Natl. Acad. Sci. USA 89:3175-79 (1992).
Anagnostou VK, Brahmer JR. Cancer Immunotherapy: A Future Paradigm Shift in the Treatment of Non-Small Cell Lung Cancer. Clinical cancer research : an official journal of the American Association for Cancer Research 2015;21 (5):976-84.
Ansell SM, Lesokhin AM, Borrello I, Halwani A, Scott EC, Gutierrez M, et al. PD-1 blockade with nivolumab in relapsed or refractory Hodgkin's lymphoma. The New England journal of medicine 2015;372(4):311-9. 41.
Barbas et al, Proc. Natl. Acad. Sci. USA 89:9339-43 (1992).
Bobo et al, Proc. Natl. Acad. Sci. USA 91 :2076-2080 (1994).
Boon T, Cerottini JC, Van den Eynde B, van der Bruggen P, Van Pel A. Tumor antigens recognized by T lymphocytes. Annual review of immunology 1994;12:337-65.
Boyman O, Kovar M, Rubinstein MP, Surh CD, Sprent J. Selective stimulation of T cell subsets with antibody-cytokine immune complexes. Science 2006;311(5769): 1924-7.
Brodeur et al, Monoclonal Antibody Production Techniques and Applications, Marcel Dekker, Inc., New York, (1987) pp. 51-63.
Bruhns P, Iannascoli B, England P, Mancardi DA, Fernandez N, Jorieux S, et al. Specificity and affinity of human Fcgamma receptors and their polymorphic variants for human IgG subclasses. Blood 2009;113(16):3716-25.
Brusko TM, Wasserfall CH, Hulme MA, Cabrera R, Schatz D, Atkinson MA. Influence of membrane CD25 stability on T lymphocyte activity: implications for immunoregulation. PloS one 2009;4(II):e7980.

(56) References Cited

OTHER PUBLICATIONS

Caron et al, J. Exp Med., 176: 1191-1195 (1992).
Chang DK, Sui J, Geng S, Muvaffak A, Bai M, Fuhlbrigge RC, et al. Humanization of an anti-CCR4 antibody that kills cutaneous T-cell lymphoma cells and abrogates suppression by T-regulatory cells. Molecular cancer therapeutics 2012;11(11):2451-61.
Choi SY, Lin D, Gout PW, Collins CC, Xu Y, Wang Y. Lessons from patient-derived xenografts for better in vitro modeling of human cancer. Advanced drug delivery reviews 2014;79-80:222-37.
Cole, et al, 1985 In: Monoclonal Antibodies and Cancer Therapy, Alan R. Liss, Inc., pp. 77-96.
Cote, et al, 1983. Proc Natl Acad Sci USA 80: 2026-2030.
Cronshaw DG, Owen C, Brown Z, Ward SG. Activation of phosphoinositide 3-kinases by the CCR4 ligand macrophage-derived chemokine is a dispensable signal for T lymphocyte chemotaxis. Journal of immunology 2004;172(12):7761-70.
Cruse, J.M. and Lewis, R.E. (eds) "Conjugate Vaccines", Contributions to Microbiology and Immunology, Carger Press, New York, (1989).
Curiel TJ, Coukos G, Zou L, Alvarez X, Cheng P, Mottram P, et al. Specific recruitment of regulatory T cells in ovarian carcinoma fosters immune privilege and predicts reduced survival. Nature medicine 2004;10(9):942-9.
Curtin JF, Candolfi M, Fakhouri TM, Liu C, Alden A, Edwards M, et al. Treg depletion inhibits efficacy of cancer immunotherapy: implications for clinical trials. PloS one 2008;3(4):e1983.
Das R, Verma R, Sznol M, Boddupalli CS, Gettinger SN, Kluger H, et al. Combination therapy with anti-CTLA-4 and anti-PD-1 leads to distinct immunologic changes in vivo. Journal of immunology 2015; 194(3):950-9.
Davidson, et al, Nat. Genet 3:219 (1993).
Davies, David R., Eduardo A. Padlan, and Steven Sheriff. "Antibody-antigen complexes." Annual review of biochemistry59.1 (1990): 439-473.
De Paiva CS, Yoon KC, Pangelinan SB, Pham S, Puthenparambil LM, Chuang EY, et al. Cleavage of functional IL-2 receptor alpha chain (CD25) from murine corneal and conjunctival epithelia by MMP-9. Journal of inflammation 2009;6:31.
Dilek N, Poirier N, Hulin P, Coulon F, Mary C, Ville S, et al. Targeting CD28, CTLA-4 and PD-LI costimulation differentially controls immune synapses and function of human regulatory and conventional T-cells. PloS one 2013;8 (12):e83139.
Duraiswamy J, Kaluza KM, Freeman GJ, Coukos G. Dual blockade of PD-1 and CTLA-4 combined with tumor vaccine effectively restores T-cell rejection function in tumors. Cancer research 2013;73(12):3591-603.
El Houda Agueznay N, Badoual C, Hans S, Gey A, Vingert B, Peyrard S, et al. Soluble interleukin-2 receptor and metalloproteinase-9 expression in head and neck cancer: prognostic value and analysis of their relationships. Clinical and experimental immunology 2007;150(I): 114-23.
Epstein et al, Proc. Natl. Acad. Sci. USA, 82: 3688 (1985).
Fishwild et al, Nature Biotechnology 14, 845-51 (1996).
Geller, A. I. et al, J. Neurochem, 64:487 (1995).
Geller, A. I. et al., Proc Natl. Acad. Sci. : U.S.A. 90:7603 (1993).
Geller, A. I., et al, Proc Natl. Acad. Sci USA 87: 1149 (1990).
Goding, Monoclonal Antibodies: Principles and Practice. Academic Press, (1986) pp. 59-103.
Han T, Abdel-Motal UM, Chang DK, Sui J, Muvaffak A, Campbell J, et al. Human anti-CCR4 minibody gene transfer for the treatment of cutaneous T-cell lymphoma. PloS one 2012;7(9):e44455.
Harlow E, and Lane D., Antibodies: A Laboratory Manual, 1988, Cold Spring Harbor Laboratory Press, Cold Spring Harbor, NY.
Hodi FS, Butler M, Oble DA, Seiden MV, Haluska FG, Kruse A, et al. Immunologic and clinical effects of antibody blockade of cytotoxic T lymphocyte-associated antigen 4 in previously vaccinated cancer patients. Proceedings of the National Academy of Sciences of the United States of America 2008;105(8):3005-10.
Hodi FS, Mihm MC, Soiffer RJ, Haluska FG, Butler M, Seiden MV, et al. Biologic activity of cytotoxic T lymphocyte-associated antigen 4 antibody blockade in previously vaccinated metastatic melanoma and ovarian carcinoma patients. Proceedings of the National Academy of Sciences of the United States of America 2003;100(8):4712-7.
Hoogenboom and Winter, J. Mol. Biol., 227:381 (1991).
Huse, et al, 1989 Science 246: 1275-1281.
Huston et al. (1988) Proc Nat Acad Sci USA 85(16):5879-5883.
Hwang et al, Proc. Natl Acad. Sci. USA, 77: 4030 (1980).
Jansen et al., Immunological Reviews 62: 185-216 (1982).
Kaplitt, M. G. et al, Nat. Genet. 8: 148 (1994).
Killen and Lindstrom, Jour. Immun. 133: 1335-2549 (1984).
Kohler and Milstein, Nature, 256:495 (1975).
Kozbor, et al, 1983 Immunol Today 4: 72.
Kozbor, J. Immunol., 133:3001 (1984).
Kudo-Saito C, Schlom J, Camphausen K, Coleman CN, Hodge JW. The requirement of multimodal therapy (vaccine, local tumor radiation, and reduction of suppressor cells) to eliminate established tumors. Clinical cancer research : an official journal of the American Association for Cancer Research 2005;I I(12):4533-44.
Labrijn, A.F. et al, 2011, Journal of immunol 187:3238-3246.
Lam, Anticancer Drug Des., 12: 145, 1997.
Lanca T, Silva-Santos B. The split nature of tumor-infiltrating leukocytes:Implications for cancer surveillance and immunotherapy. Oncoimmunology 2012; 1(5): 717-25.
LeGal LaSalle et al, Science, 259:988 (1993).
Agarwal, Roshan, and Stan B. Kaye. "Ovarian cancer: strategies for overcoming resistance to chemotherapy." Nature Reviews Cancer 3.7 (2003): 502.
Disis ML, Rivkin S. Future directions in the management of ovarian cancer.Hematology/oncology clinics of North America 2003;17(4): 1075-85.
Wood KJ, Sakaguchi S. Regulatory T cells in transplantation tolerance. Nature reviews Immunology 2003;3(3): 199-210.
Baecher-Allan C, Anderson DE. Regulatory cells and human cancer. Seminars in cancer biology 2006;16(2):98-105.
Fontenot JD, Gavin MA, Rudensky AY. Foxp3 programs the development and function of CD4+CD25+ regulatory T cells. Nature immunology 2003;4(4):330-6.
Jacques Y, Le Mauff B, Boeffard F, Godard A, Soulillou JP. A soluble interleukin 2 receptor produced by a normal alloreactive human T cell clone binds interleukin 2 with low affinity. J Immunol 1987;139(7):2308-16.
Zou W. Immunosuppressive networks in the tumour environment and their therapeutic relevance. Nature reviews Cancer 2005;5(4):263-74.
Swaika A, Hammond WA, Joseph RW. Current state of anti-PD-LI and anti-PD-1 agents in cancer therapy. Molecular immunology 2015.
Nesspor TC, Raju TS, Chin CN, Vafa O, Brezski RJ. Avidity confers FcgammaR binding and immune effector function to aglycosylated immunoglobulin GI. Journal of molecular recognition : JMR 2012;25(3): 147-54.

\* cited by examiner

Figure 3
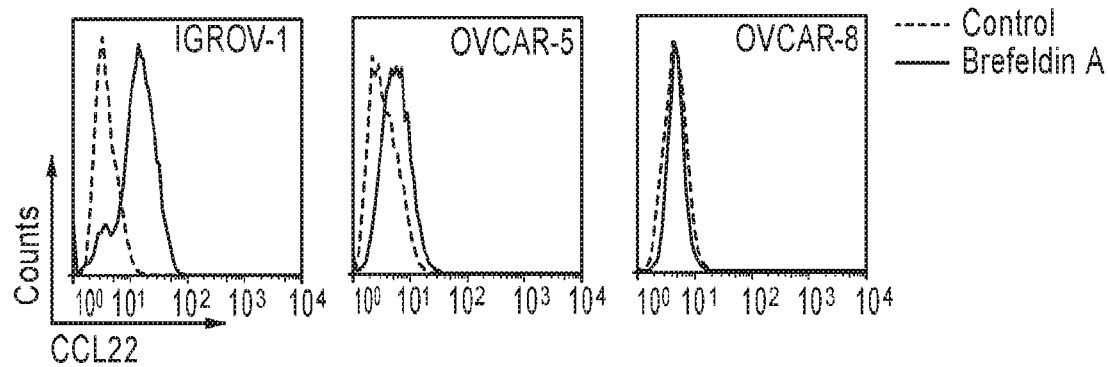
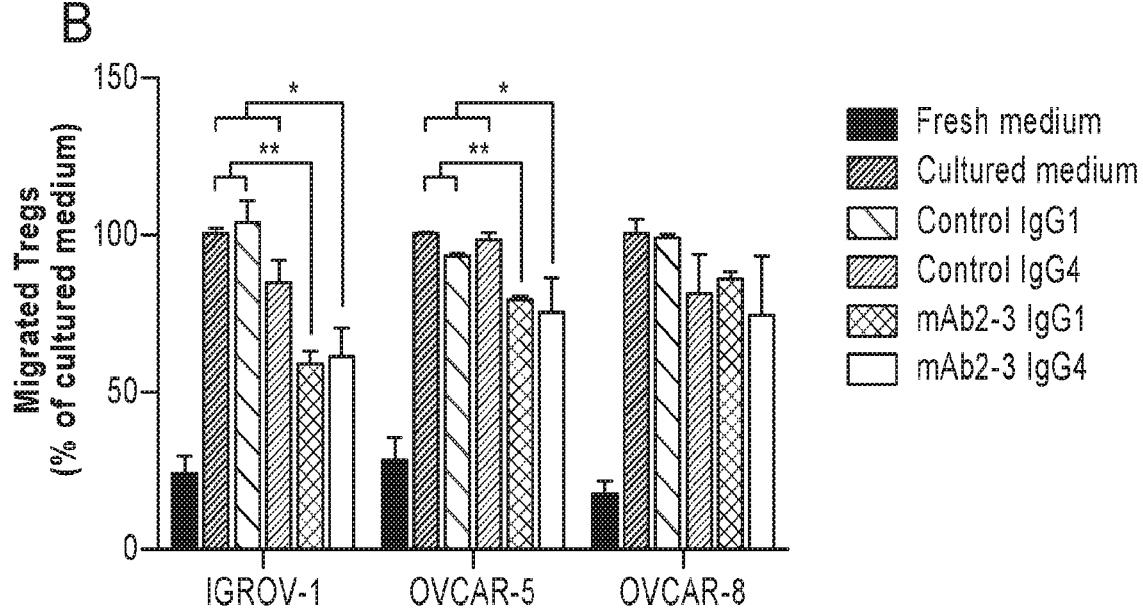
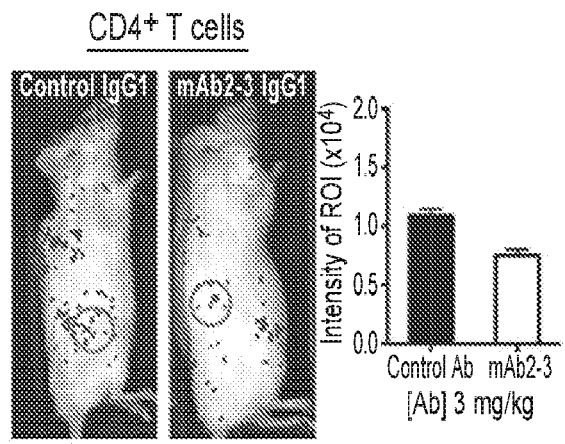
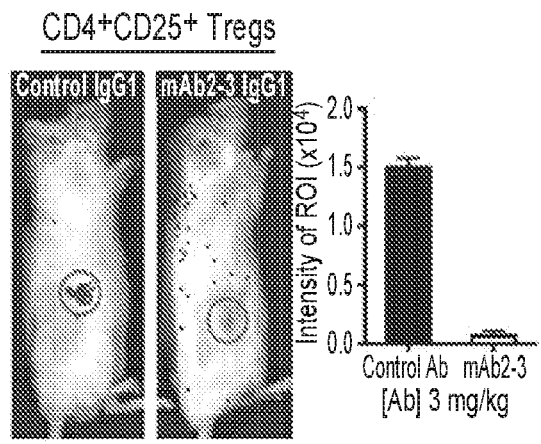

Figure 4
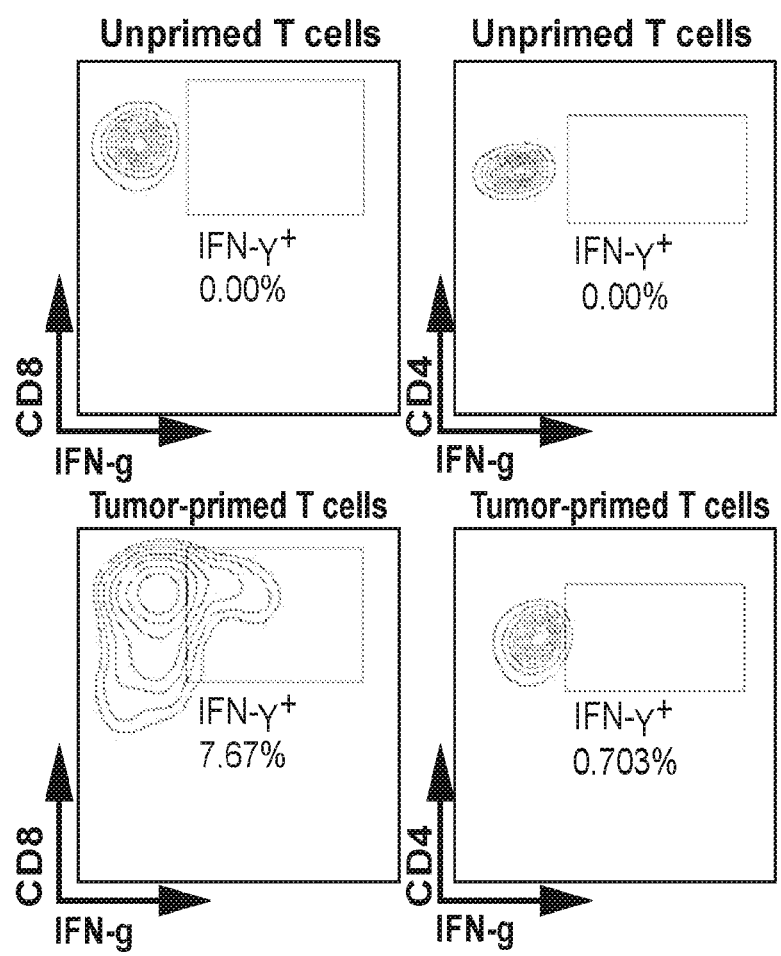
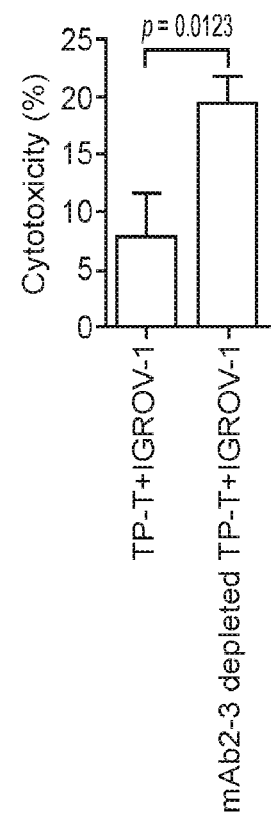

Figure 8

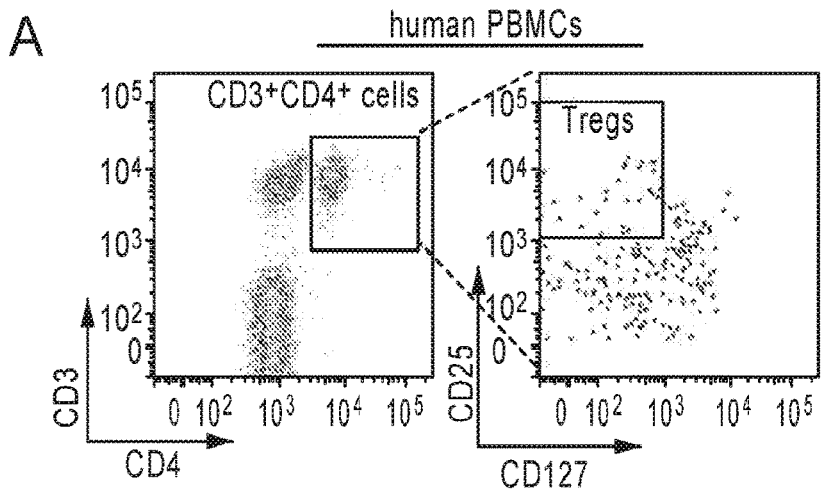

A

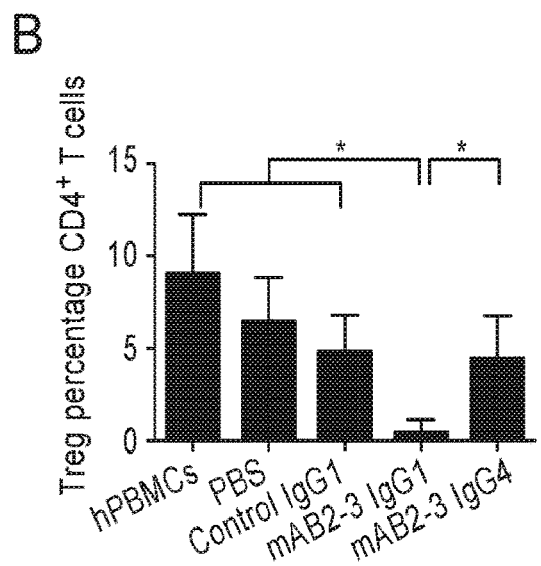

B

C

Analysis of CD4+CD25+CD127$^{dim/-}$ T cell subsets after in vivo circulation.

| | PBMCs | PBS | | Control IgG1 | | mAb2-3 IgG1 | | mAb2-3 IgG4 | |
|---|---|---|---|---|---|---|---|---|---|
| | | D1 | D7 | D1 | D7 | D1 | D7 | D1 | D7 |
| Tregs | 9.02±3.2 2 | 6.44±2.39 | 4.40±0.82 | 4.80±2.0 0 | 3.61±0.6 1 | 0.41±0.71 * | 2.14±0.37 * | 4.40±2.36 | 4.53±1.19 |

PBMCs from mouse blood were stained with the indicated surface marker and analyzed by FACS. Percentages of cells in the total CD4+ T cell population are shown. All the values are average ±S.D.. *, udent's t-test p value < 0.05 compared to PBS control group.

Figure 13
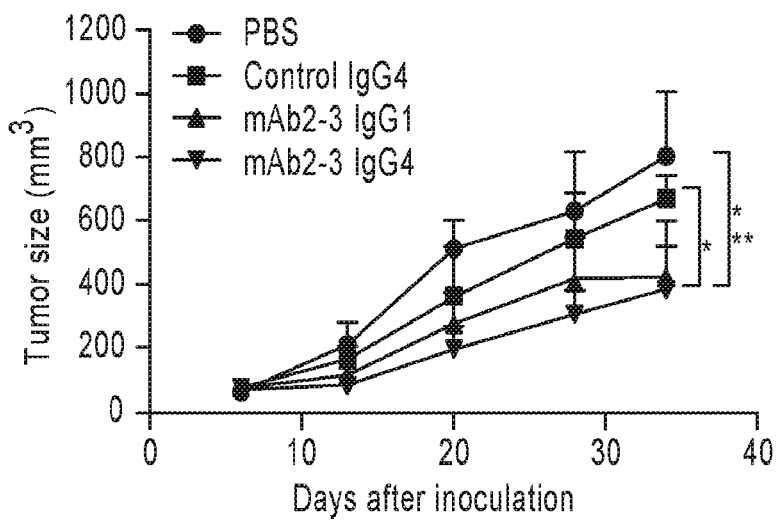
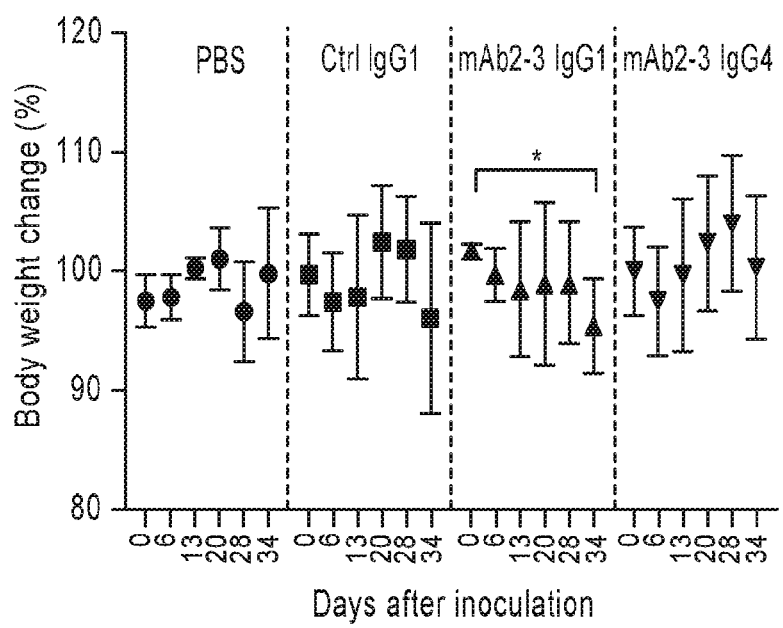

SEQUENCE LISTING

```
<160> NUMBER OF SEQ ID NOS: 46

<210> SEQ ID NO 1
<211> LENGTH: 354
<212> TYPE: DNA
<213> ORGANISM: Artificial Sequence
<220> FEATURE:
<223> OTHER INFORMATION: Humanized VH chain of mAb2-3 nucleic acid

<400> SEQUENCE: 1
caggtgcagc tggtgcagag cggcgcggaa gtgaaaaaac cgggcgcgag cgtgaaagtg      60
agctgcaaag cgagcggcta tacctttgcg agcgcgtgga tgcattggat gcgccaggcg     120
ccgggccagg gcctggaatg gattggctgg attaacccgg gcaacgtgaa caccaaatat     180
aacgaaaaat ttaaaggccg cgcgaccctg accgtggata ccagcaccaa caccgcgtat     240
atggaactga gcagcctgcg cagcgaagat accgcggtgt attattgcgc gcgcagcacc     300
tattatcgcc cgctggatta ttggggccag ggcaccctgg tgaccgtgag cagc           354

<210> SEQ ID NO 2
<211> LENGTH: 118
<212> TYPE: PRT
<213> ORGANISM: Artificial Sequence
<220> FEATURE:
<223> OTHER INFORMATION: VH chain of mAb2-3 IgG4

<400> SEQUENCE: 2
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ala
            20                  25                  30

Trp Met His Trp Met Arg Gln Ala Pro Gly Gln Gly Leu Glu Trp Ile
            35                  40                  45

Gly Trp Ile Asn Pro Gly Asn Val Asn Thr Lys Tyr Asn Glu Lys Phe
        50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
                100                 105                 110

Leu Val Thr Val Ser Ser
            115
```

<210> SEQ ID NO 3
<211> LENGTH: 336
<212> TYPE: DNA
<213> ORGANISM: Artificial Sequence
<220> FEATURE:
<223> OTHER INFORMATION: Humanized VL chain of mAb2-3 IgG4 nucleic acid

<400> SEQUENCE: 3

```
gatattgtga tgacccagag cccggatagc ctggcggtga gcctgggcga acgcgcgacc    60
attaactgca aaagcagcca gagcattctg tatagcagca accagaaaaa ctatctggcg   120
tggtatcagc agaaaccggg ccagagcccg aaactgctga tttattgggc gagcacccgc   180
gaaagcggcg tgccggatcg ctttagcggc agcggcagcg gcaccgattt taccctgacc   240
attagcagcc tgcaggcgga agatgtggcg gtgtattatt gccatcagta tatgagcagc   300
tatacctttg gccagggcac caaactggaa attaaa                             336
```

<210> SEQ ID NO 4
<211> LENGTH: 112
<212> TYPE: PRT
<213> ORGANISM: Artificial Sequence
<220> FEATURE:
<223> OTHER INFORMATION: VL chain of mAb2-3 IgG4

<400> SEQUENCE: 4

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Met Ser Ser Tyr Thr Phe Gly Gln Gly Thr Lys Leu Glu Ile Lys
                100                 105                 110
```

<210> SEQ ID NO 5

<211> LENGTH: 981
<212> TYPE: DNA
<213> ORGANISM: Artificial Sequence
<220> FEATURE:
<223> OTHER INFORMATION: Humanized IgG4 Isotype Region nucleic acid
      sequence

<400> SEQUENCE: 5

```
gcgagcacca aaggcccgag cgtgtttccg ctggcgccgt gcagccgcag caccagcgaa    60
agcaccgcgg cgctgggctg cctggtgaaa gattattttc cggaaccggt gaccgtgagc   120
tggaacagcg gcgcgctgac cagcggcgtg cataccttc cggcggtgct gcagagcagc   180
ggcctgtata gcctgagcag cgtggtgacc gtgccgagca gcagcctggg caccaaaacc   240
tatacctgca acgtggatca taaaccgagc aacaccaaag tggataaacg cgtggaaagc   300
aaatatggcc cgccgtgccc gagctgcccg gcgccggaat tctgggcgg cccgagcgtg   360
tttctgtttc cgccgaaacc gaaagatacc ctgatgatta gccgcacccc ggaagtgacc   420
tgcgtggtgg tggatgtgag ccaggaagat ccggaagtgc agtttaactg gtatgtggat   480
ggcgtggaag tgcataacgc gaaaaccaaa ccgcgcgaag aacagtttaa cagcacctat   540
cgcgtggtga gcgtgctgac cgtgctgcat caggattggc tgaacggcaa agaatataaa   600
tgcaaagtga gcaacaaagg cctgccgagc agcattgaaa aaaccattag caaagcgaaa   660
ggccagccgc gcgaaccgca ggtgtatacc ctgccgccga gccgggaaga atgaccaaa   720
aaccaggtga gcctgacctg cctggtgaaa ggcttttatc cgagcgatat tgcggtggaa   780
tgggaaagca acggccagcc ggaaaacaac tataaaacca ccccgccggt gctggatagc   840
gatggcagct ttttctgta tagccgcctg accgtggata aaagccgctg gcaggaaggc   900
aacgtgttta gctgcagcgt gatgcatgaa gcgctgcata accattatac ccagaaaagc   960
ctgagcctga gcctgggcaa a                                             981
```

<210> SEQ ID NO 6
<211> LENGTH: 327
<212> TYPE: PRT
<213> ORGANISM: Artificial Sequence
<220> FEATURE:
<223> OTHER INFORMATION: IgG4 Isotype Region amino acid sequence

<400> SEQUENCE: 6

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Pro Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 7
<211> LENGTH: 975
<212> TYPE: DNA
<213> ORGANISM: Artificial Sequence
<220> FEATURE:
<223> OTHER INFORMATION: Humanized IgG4 with stabilized IgG4 core hinge,
      nucleic acid sequence

<400> SEQUENCE: 7
accaaaggcc cgagcgtgtt tccgctggcg ccgtgcagcc gcagcaccag cgaaagcacc    60
gcggcgctgg gctgcctggt gaaagattat tttccggaac cggtgaccgt gagctggaac   120
agcggcgcgc tgaccagcgg cgtgcatacc tttccggcgg tgctgcagag cagcggcctg   180
tatagcctga gcagcgtggt gaccgtgccg agcagcagcc tgggcaccaa aacctatacc   240
tgcaacgtgg atcataaacc gagcaacacc aaagtggata acgcgtggga agcaaatat   300 ggcccgccgt gcccgccgtg cccggcgccg gaatttctgg gcggcccgag cgtgtttctg   360
tttccgccga aaccgaaaga taccctgatg attagccgca ccccggaagt gacctgcgtg   420
gtggtggatg tgagccagga agatccggaa gtgcagttta ctggtatgt ggatggcgtg    480 gaagtgcata acgcgaaaac caaaccgcgc gaagaacagt ttaacagcac ctatcgcgtg   540
gtgagcgtgc tgaccgtgct gcatcaggat tggctgaacg gcaaagaata taaatgcaaa   600
gtgagcaaca aaggcctgcc gagcagcatt gaaaaaacca ttagcaaagc gaaaggccag   660
ccgcgcgaaa cgcaggtgta tcctgccg ccgagcccgg aagaaatgac caaaaaccag   720
gtgagcctga cctgcctggt gaaaggcttt tatccgagcg atattgcggt ggaatgggaa   780
agcaacggcc agccggaaaa caactataaa accaccccgc cggtgctgga tagcgatggc   840
agcttttttc tgtatagcaa actgaccgtg gataaaagcc gctggcagga aggcaacgtg   900
tttagctgca gcgtgatgca tgaagcgctg cataaccatt atacccagaa aagcctgagc   960
ctgagcctgg gcaaa 975

<210> SEQ ID NO 8
<211> LENGTH: 325
<212> TYPE: PRT
<213> ORGANISM: Artificial Sequence
<220> FEATURE:
<223> OTHER INFORMATION: IgG4 with stabilized IgG4 core hinge, amino acid sequence

<400> SEQUENCE: 8

```
Thr Lys Gly Pro Ser Val Phe Pro Leu Ala Pro Cys Ser Arg Ser Thr
1               5                   10                  15

Ser Glu Ser Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Lys Thr Tyr Thr
65                  70                  75                  80

Cys Asn Val Asp His Lys Pro Ser Asn Thr Lys Val Asp Lys Arg Val
                85                  90                  95

Glu Ser Lys Tyr Gly Pro Pro Cys Pro Pro Cys Pro Ala Pro Glu Phe
            100                 105                 110

Leu Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser Gln Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Gly Leu Pro Ser
        195                 200                 205

Ser Ile Glu Lys Thr Ile Ser Lys Ala Lys Gly Gln Pro Arg Glu Pro
    210                 215                 220

Gln Val Tyr Thr Leu Pro Pro Ser Pro Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Lys Leu
        275                 280                 285

Thr Val Asp Lys Ser Arg Trp Gln Glu Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Leu Gly Lys
            325
```

<210> SEQ ID NO 9

```
<211> LENGTH: 8
<212> TYPE: PRT
<213> ORGANISM: Artificial Sequence
<220> FEATURE:
<223> OTHER INFORMATION: Humanized anti-CCR4 antibody heavy chain CDR

<400> SEQUENCE: 9

Gly Tyr Thr Phe Ala Ser Ala Trp
1               5

<210> SEQ ID NO 10
<211> LENGTH: 12
<212> TYPE: PRT
<213> ORGANISM: Artificial Sequence
<220> FEATURE:
<223> OTHER INFORMATION: Humanized anti-CCR4 antibody light chain CDR

<400> SEQUENCE: 10

Gln Ser Ile Leu Tyr Ser Ser Asn Gln Lys Asn Tyr
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Humanized anti-CCR4 antibody heavy chain CDR

<400> SEQUENCE: 11

Ile Asn Pro Gly Asn Val Asn Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Humanized anti-CCR4 antibody light chain CDR

<400> SEQUENCE: 12

Trp Ala Ser Thr Arg Glu
1               5

<210> SEQ ID NO 13
<211> LENGTH: 9
<212> TYPE: PRT
<213> ORGANISM: Artificial Sequence
<220> FEATURE:
<223> OTHER INFORMATION: Humanized anti-CCR4 antibody heavy chain CDR

<400> SEQUENCE: 13

Ser Thr Tyr Tyr Arg Pro Leu Asp Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Humanized anti-CCR4 antibody light chain CDR

<400> SEQUENCE: 14

His Gln Tyr Met Ser Ser Tyr Thr
1               5

<210> SEQ ID NO 15
<211> LENGTH: 354
```

<212> TYPE: DNA
<213> ORGANISM: Artificial Sequence
<220> FEATURE:
<223> OTHER INFORMATION: Synthetic antibody 1-44 VH chain nucleic acid
      sequence

<400> SEQUENCE: 15
caggtgcagc tggtgcagag cggagccgag gtgaagaagc ctggagcttc cgtcaaggtg       60
tcctgcaagg ccagcggcta caccttcgcc agccaatgga tgcactggat gcggcaggca      120
cctggacagg gcctcgaatg gatcggctgg atcaaccccg gcaacgtgaa caccaagtac      180
aacgagaagt tcaagggcag ggccacccctg accgtggaca ccagcaccaa caccgcctac      240
atggaactga gcagcctgcg gagcgaggac accgccgtgt actactgcgc cagaagcacc      300
tggtaccggc cgctggacta ctggggccag ggcaccctgg tgaccgtgag cagc            354

<210> SEQ ID NO 16
<211> LENGTH: 118
<212> TYPE: PRT
<213> ORGANISM: Artificial Sequence
<220> FEATURE:
<223> OTHER INFORMATION: Antibody 1-44 VH chain amino acid sequence

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Gln
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Trp Tyr Arg Pro Leu Asp Tyr Trp Gly Gln Gly Thr
            100                 105                 110

Leu Val Thr Val Ser Ser
        115

<210> SEQ ID NO 17
<211> LENGTH: 336
<212> TYPE: DNA
<213> ORGANISM: Artificial Sequence
<220> FEATURE:
<223> OTHER INFORMATION: Synthetic antibody 1-44 VL chain nucleic acid
      sequence

<400> SEQUENCE: 17
gacatcgtga tgacccagag ccccgacagc ctggccgtga gcctgggcga gcgggccacc       60
atcaactgca agagcagcca gagcatcctg tacagcagca ccagaagaa ctacctggcc      120 tggtatcagc agaagcccgg ccagagcccc aagctgctga tctactgggc cagcacccgg      180
gagagcggcg tgcccgaccg gtttagcggc agcggctccg gcaccgactt cacccctgacc      240 atcagcagcc tgcaggccga ggacgtggcc gtgtactact gccaccagta catcagcagc      300
tacaccttcg gccagggcac aaagctggaa atcaag                              336

<210> SEQ ID NO 18

-continued

```
<211> LENGTH: 112
<212> TYPE: PRT
<213> ORGANISM: Artificial Sequence
<220> FEATURE:
<223> OTHER INFORMATION: Antibody 1-44 VL chain amino acid sequence

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Ile Ser Ser Tyr Thr Phe Gly Gln Gly Thr Lys Leu Glu Ile Lys
            100                 105                 110

<210> SEQ ID NO 19
<211> LENGTH: 354
<212> TYPE: DNA
<213> ORGANISM: Artificial Sequence
<220> FEATURE:
<223> OTHER INFORMATION: Synthetic antibody 1-49 VH chain nucleic acid
      sequence

<400> SEQUENCE: 19
caggtgcagc tggtgcagag cggagccgag gtgaagaagc ctggagcttc cgtcaaggtg      60
tcctgcaagg ccagcggcta caccttcgcc agcagctgga tgcactggat gcggcaggca     120
cctggacagg gcctcgaatg gatcggctgg atcaaccccg gcaacgtgaa caccaagtac     180
aacgagaagt tcaagggcag ggccacactg accgtggaca ccagcaccaa caccgcctac     240
atggaactga gcagcctgcg gagcgaggac accgccgtgt actactgcgc cagaagcacg     300
tggtatcggc cgaatgacta ctggggccag ggcaccctgg tgaccgtgag cagc           354

<210> SEQ ID NO 20
<211> LENGTH: 118
<212> TYPE: PRT
<213> ORGANISM: Artificial Sequence
<220> FEATURE:
<223> OTHER INFORMATION: antibody 1-49 VH chain amino acid sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ser
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

Ala Arg Ser Thr Trp Tyr Arg Pro Asn Asp Tyr Trp Gly Gln Gly Thr
            100                 105                 110

Leu Val Thr Val Ser Ser
        115

<210> SEQ ID NO 21
<211> LENGTH: 336
<212> TYPE: DNA
<213> ORGANISM: Artificial Sequence
<220> FEATURE:
<223> OTHER INFORMATION: Synthetic antibody 1-49 VL chain nucleic acid
      sequence

<400> SEQUENCE: 21
gacatcgtga tgacccagag ccccgacagc ctggccgtga gcctgggcga gcgggccacc      60
atcaactgca agagcagcca gagcatcctg tacagcagca ccagaagaa ctacctggcc     120 tggtatcagc agaagcccgg ccagagcccc aagctgctga tctactgggc cagcacccgg    180
gagagcggcg tgcccgaccg gtttagcggc agcggctccg gcaccgactt caccctgacc    240
atcagcagcc tgcaggccga ggacgtggcc gtgtactact gccaccagta caaaagcagc    300
tacaccttcg gccagggcac aaagctggaa atcaag                              336

<210> SEQ ID NO 22
<211> LENGTH: 112
<212> TYPE: PRT
<213> ORGANISM: Artificial Sequence
<220> FEATURE:
<223> OTHER INFORMATION: Antibody 1-49 VL chain amino acid sequence

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Lys Ser Ser Tyr Thr Phe Gly Gln Gly Thr Lys Leu Glu Ile Lys
            100                 105                 110

<210> SEQ ID NO 23
<211> LENGTH: 354
<212> TYPE: DNA
<213> ORGANISM: Artificial Sequence
<220> FEATURE:
<223> OTHER INFORMATION: Synthetic antibody 2-1 VH chain nucleic acid
      sequence

<400> SEQUENCE: 23
caggtgcagc tggtgcagag cggagccgag gtgaagaagc ctggagcttc cgtcaaggtg      60
tcctgcaagg ccagcggcta caccttcgcc agcagctgga tgcactggat gcggcaggca    120
cctggacagg gctcgaatg gatcggctgg atcaaccccg caacgtgaa caccaagtac    180 aacgagaagt tcaagggcag ggccaccctg accgtggaca ccagcaccaa caccgcctac    240

```
atggaactga gcagcctgcg gagcgaggac accgccgtgt actactgcgc cagaaccacc       300
cgttatcggc ccctggacta ctggggccag ggcaccctgg tgaccgtgag cagc             354
```

<210> SEQ ID NO 24
<211> LENGTH: 118
<212> TYPE: PRT
<213> ORGANISM: Artificial Sequence
<220> FEATURE:
<223> OTHER INFORMATION: Antibody 2-1 VH chain amino acid sequence

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Ser
            20                  25                  30

Trp Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Thr Arg Tyr Arg Pro Leu Asp Tyr Trp Gly Gln Gly Thr
            100                 105                 110

Leu Val Thr Val Ser Ser
        115
```

<210> SEQ ID NO 25
<211> LENGTH: 336
<212> TYPE: DNA
<213> ORGANISM: Artificial Sequence
<220> FEATURE:
<223> OTHER INFORMATION: Synthetic antibody 2-1 VL chain nucleic acid
      sequence

<400> SEQUENCE: 25

```
gacatcgtga tgacccagag ccccgacagc ctggccgtga gcctgggcga gcgggccacc       60
atcaactgca agagcagcca gagcatcctg tacagcagca ccagaagaa ctacctggcc       120 tggtatcagc agaagcccgg ccagagcccc aagctgctga tctactgggc cagcacccgg       180
gagagcggcg tgcccgaccg gtttagcggc agcggctccg gcaccgactt cacccctgacc       240 atcagcagcc tgcaggccga ggacgtggcc gtgtactact gccaccagta ccgtagcagc       300
tacaccttcg gccagggcac aaagctggaa atcaag                                 336
```

<210> SEQ ID NO 26
<211> LENGTH: 112
<212> TYPE: PRT
<213> ORGANISM: Artificial Sequence
<220> FEATURE:
<223> OTHER INFORMATION: Antibody 2-1 VL chain amino acid sequence

<400> SEQUENCE: 26

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
```

35                  40                  45
Ser Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                 85                  90                  95

Tyr Arg Ser Ser Tyr Thr Phe Gly Gln Gly Thr Lys Leu Glu Ile Lys
            100                 105                 110

<210> SEQ ID NO 27
<211> LENGTH: 354
<212> TYPE: DNA
<213> ORGANISM: Artificial Sequence
<220> FEATURE:
<223> OTHER INFORMATION: Synthetic antibody 2-2 VH chain nucleic acid
      sequence

<400> SEQUENCE: 27
caggtgcagc tggtgcagag cggagccgag gtgaagaagc ctggagcttc cgtcaaggtg      60
tcctgcaagg ccagcggcta caccttcgcc agccaatata tgcactggat gcggcaggca     120
cctggacagg gcctcgaatg gatcggctgg atcaaccccg gcaacgtgaa caccaagtac     180
aacgagaagt tcaagggcag ggccacccty accytggaca ccagcaccaa caccgcctac     240
atggaactga gcagcctgcg gagcgaggac accgccgtgt actactgcgc cagactgacc     300
tattatcggc cgccggacta ctggggccag ggcaccctgg tgaccgtgag cagc           354

<210> SEQ ID NO 28
<211> LENGTH: 118
<212> TYPE: PRT
<213> ORGANISM: Artificial Sequence
<220> FEATURE:
<223> OTHER INFORMATION: Antibody 2-2 VH chain amino acid sequence

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Gln
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Thr Tyr Tyr Arg Pro Pro Asp Tyr Trp Gly Gln Gly Thr
            100                 105                 110

Leu Val Thr Val Ser Ser
        115

<210> SEQ ID NO 29
<211> LENGTH: 336
<212> TYPE: DNA
<213> ORGANISM: Artificial Sequence
<220> FEATURE:
<223> OTHER INFORMATION: Synthetic antibody 2-2 VL chain nucleic acid
      sequence

<400> SEQUENCE: 29

```
gacatcgtga tgacccagag ccccgacagc ctggccgtga gcctgggcga gcgggccacc      60
atcaactgca agagcagcca gagcatcctg tacagcagca accagaagaa ctacctggcc     120
tggtatcagc agaagcccgg ccagagcccc aagctgctga tctactgggc cagcacccgg     180
gagagcggcg tgcccgaccg gtttagcggc agcggctccg gcaccgactt caccctgacc     240
atcagcagcc tgcaggccga ggacgtggcc gtgtactact gccaccagta ctatagcagc     300
tacaccttcg gccagggcac aaagctggaa atcaag                               336
```

```
<210> SEQ ID NO 30
<211> LENGTH: 112
<212> TYPE: PRT
<213> ORGANISM: Artificial Sequence
<220> FEATURE:
<223> OTHER INFORMATION: Antibody 2-2 VL chain amino acid sequence
```

<400> SEQUENCE: 30

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Ser Tyr Thr Phe Gly Gln Gly Thr Lys Leu Glu Ile Lys
            100                 105                 110
```

```
<210> SEQ ID NO 31
<211> LENGTH: 8
<212> TYPE: PRT
<213> ORGANISM: Mus musculus
```

<400> SEQUENCE: 31

```
Gly Tyr Thr Phe Ala Ser Tyr Tyr
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Ab1-44 heavy chain CDR
```

<400> SEQUENCE: 32

```
Gly Tyr Thr Phe Ala Ser Gln Trp
1               5
```

```
<210> SEQ ID NO 33
<211> LENGTH: 8
<212> TYPE: PRT
<213> ORGANISM: Artificial Sequence
<220> FEATURE:
<223> OTHER INFORMATION: Ab1-49 heavy chain CDR
```

<400> SEQUENCE: 33

```
Gly Tyr Thr Phe Ala Ser Ser Trp
1               5

<210> SEQ ID NO 34
<211> LENGTH: 9
<212> TYPE: PRT
<213> ORGANISM: Artificial Sequence
<220> FEATURE:
<223> OTHER INFORMATION: Ab1-44 heavy chain CDR

<400> SEQUENCE: 34

Ser Thr Trp Tyr Arg Pro Leu Asp Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: Ab1-49 heavy chain CDR

<400> SEQUENCE: 35

Ser Thr Trp Tyr Arg Pro Asn Asp Tyr
1               5

<210> SEQ ID NO 36
<211> LENGTH: 9
<212> TYPE: PRT
<213> ORGANISM: Artificial Sequence
<220> FEATURE:
<223> OTHER INFORMATION: Ab2-1 heavy chain CDR

<400> SEQUENCE: 36

Thr Thr Arg Tyr Arg Pro Leu Asp Tyr
1               5

<210> SEQ ID NO 37
<211> LENGTH: 9
<212> TYPE: PRT
<213> ORGANISM: Artificial Sequence
<220> FEATURE:
<223> OTHER INFORMATION: Ab2-2 heavy chain CDR

<400> SEQUENCE: 37

Leu Thr Tyr Tyr Arg Pro Pro Asp Tyr
1               5

<210> SEQ ID NO 38
<211> LENGTH: 8
<212> TYPE: PRT
<213> ORGANISM: Mus musculus

<400> SEQUENCE: 38

His Gln Tyr Leu Ser Ser Tyr Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Ab1-44 light chain CDR

<400> SEQUENCE: 39

His Gln Tyr Ile Ser Ser Tyr Thr
1               5
```

<210> SEQ ID NO 40
<211> LENGTH: 8
<212> TYPE: PRT
<213> ORGANISM: Artificial Sequence
<220> FEATURE:
<223> OTHER INFORMATION: Ab1-49 light chain CDR

<400> SEQUENCE: 40

His Gln Tyr Lys Ser Ser Tyr Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Ab2-1 light chain CDR

<400> SEQUENCE: 41

His Gln Tyr Arg Ser Ser Tyr Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Ab2-2 light chain CDR

<400> SEQUENCE: 42

His Gln Tyr Tyr Ser Ser Tyr Thr
1               5

<210> SEQ ID NO 43
<211> LENGTH: 354
<212> TYPE: DNA
<213> ORGANISM: Homo sapiens

<400> SEQUENCE: 43
caggtgcagc tggtgcagag cggagccgag gtgaagaagc ctggagcttc cgtcaaggtg      60
tcctgcaagg ccagcggcta caccttcgcc agctactaca tgcactggat gcggcaggca     120
cctggacagg gcctcgaatg gatcggctgg atcaaccccg gcaacgtgaa caccaagtac     180
aacgagaagt tcaagggcag ggccaccctg accgtggaca ccagcaccaa caccgcctac     240
atggaactga gcagcctgcg gagcgaggac accgccgtgt actactgcgc cagaagcacc     300
tactaccggc ccctggacta ctggggccag ggcaccctgg tgaccgtgag cagc           354

<210> SEQ ID NO 44
<211> LENGTH: 118
<212> TYPE: PRT
<213> ORGANISM: Homo sapiens

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
                20                  25                  30

Tyr Met His Trp Met Arg Gln Ala Pro Gly Gln Gly Leu Glu Trp Ile
            35                  40                  45

Gly Trp Ile Asn Pro Gly Asn Val Asn Thr Lys Tyr Asn Glu Lys Phe
        50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Thr Tyr Tyr Arg Pro Leu Asp Tyr Trp Gly Gln Gly Thr
        100                 105                 110

Leu Val Thr Val Ser Ser
        115

<210> SEQ ID NO 45
<211> LENGTH: 336
<212> TYPE: PRT
<213> ORGANISM: Homo sapiens

<400> SEQUENCE: 45

Gly Ala Cys Ala Thr Cys Gly Thr Gly Thr Gly Ala Cys Cys Cys
1               5                   10                  15

Ala Gly Ala Gly Cys Cys Cys Gly Ala Cys Ala Gly Cys Cys Thr
            20                  25                  30

Gly Gly Cys Cys Gly Thr Gly Ala Cys Cys Thr Gly Gly Gly Cys
        35                  40                  45

Gly Ala Gly Cys Gly Gly Cys Cys Ala Cys Ala Thr Cys Ala
    50                  55                  60

Ala Cys Thr Gly Cys Ala Ala Gly Ala Gly Cys Ala Gly Cys Cys Ala
65                  70                  75                  80

Gly Ala Gly Cys Ala Thr Cys Cys Thr Gly Thr Ala Cys Ala Gly Cys
            85                  90                  95

Ala Gly Cys Ala Ala Cys Cys Ala Gly Ala Ala Gly Ala Ala Cys Thr
        100                 105                 110

Ala Cys Cys Thr Gly Cys Cys Thr Gly Gly Thr Ala Thr Cys Ala
            115                 120                 125

Gly Cys Ala Gly Ala Ala Gly Cys Cys Cys Gly Gly Cys Cys Ala Gly
    130                 135                 140

Ala Gly Cys Cys Cys Cys Ala Ala Gly Cys Thr Gly Cys Thr Gly Ala
145                 150                 155                 160

Thr Cys Thr Ala Cys Thr Gly Gly Cys Cys Ala Gly Cys Ala Cys
            165                 170                 175

Cys Cys Gly Gly Gly Ala Gly Ala Gly Cys Gly Gly Cys Gly Thr Gly
        180                 185                 190

Cys Cys Cys Gly Ala Cys Gly Gly Thr Thr Thr Ala Gly Cys Gly
            195                 200                 205

Gly Cys Ala Gly Cys Gly Gly Cys Thr Cys Cys Gly Gly Cys Ala Cys
    210                 215                 220

Cys Gly Ala Cys Thr Thr Cys Ala Cys Cys Cys Thr Gly Ala Cys Cys
225                 230                 235                 240

Ala Thr Cys Ala Gly Cys Ala Gly Cys Cys Thr Gly Cys Ala Gly Gly
            245                 250                 255

Cys Cys Gly Ala Gly Gly Ala Cys Gly Thr Gly Gly Cys Cys Gly Thr
        260                 265                 270

Gly Thr Ala Cys Thr Ala Cys Thr Gly Cys Cys Ala Cys Ala Gly
            275                 280                 285

Thr Ala Cys Cys Thr Gly Ala Gly Cys Ala Gly Cys Thr Ala Cys Ala
    290                 295                 300

Cys Cys Thr Thr Cys Gly Gly Cys Cys Ala Gly Gly Gly Cys Ala Cys

```
                305                 310                 315                 320
Ala Ala Ala Gly Cys Thr Gly Gly Ala Ala Ala Thr Cys Ala Ala Gly
                325                 330                 335

<210> SEQ ID NO 46
<211> LENGTH: 112
<212> TYPE: PRT
<213> ORGANISM: Homo sapiens

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Tyr Thr Phe Gly Gln Gly Thr Lys Leu Glu Ile Lys
            100                 105                 110
```

PHARMACEUTICAL COMPOSITIONS COMPRISING HUMANIZED ANTI-CCR4 IGG4 ANTIBODY

RELATED APPLICATIONS

This application is a national stage entry of PCT application No. PCT/US2016/026232 filed on Apr. 6, 2016, which claims the benefit of, and priority to, U.S. Provisional Application No. 62/155,966, filed on May 1, 2015, U.S. Provisional Application No. 62/217,419, filed on Sep. 11, 2015, and U.S. Provisional Application No. 62/237,942, filed on Oct. 6, 2015, the contents of each of which are hereby incorporated in their entireties.

GOVERNMENT INTEREST

This invention was made with government support under U01 CA-152990 awarded by the National Institutes of Health. The government has certain rights in the invention.

INCORPORATION-BY-REFERENCE OF SEQUENCE LISTING

The contents of the file named "DFCI_116_001WO_ST25.txt", which was created on Jun. 3, 2016 and is 35 KB in size are hereby incorporated by reference in their entirety.

FIELD OF THE INVENTION

The present invention relates generally to modulating T-cell function.

BACKGROUND OF THE INVENTION

Chemokines are a family of secreted proteins known primarily for their roles in leukocyte activation and chemotaxis. Their specific interaction with chemokine receptors on target cells trigger signaling cascades that result in inflammatory mediator release, changes in cell shape, and cellular migration. The CC chemokine receptor 4 (CCR4) is the cognate receptor for the CC chemokines CCL17 and CCL22, and is expressed on functionally distinct subsets of T cells, including T helper type 2 cells (Th2), and the majority of regulatory T cells (Tregs). Growing evidence indicates that CCL17/22 secretion promotes increased numbers of tumor-infiltrating Tregs by malignant entities such as colorectal, ovarian, Hodgkin's lymphoma and glioblastoma Increased levels of Treg in tumors hinder efficient antitumor immune responses and are often associated with poor clinical outcome and tumor progression.

Accordingly, one major obstacle of successful cancer therapies might be caused by migration of Tregs into tumors and their suppression of antitumor immune responses in the tumor microenvironment. In an effort to abrogate Treg suppressive function and consequently promote antitumor immunity, monoclonal antibodies (mAbs) as immunotherapeutics against Tregs have been evaluated in preclinical and clinical studies in recent years However, a caveat to systemic Treg depletion with mAb immunotherapy is its highly anticipated association with autoimmunity. An alternative strategy to avoid Treg induced cancer immune evasion is to develop a tumor-associated Treg targeting therapy that directly hinders Treg attraction and accumulation in tumor tissue.

SUMMARY OF THE INVENTION

The invention provides methods of depleting regulatory T-cells (Tregs) in a subject by administering to a subject in need thereof a humanized anti-CCR4 antibody having a heavy chain with three CDRs having the amino acid sequences GYTFASAW (SEQ ID NO: 9), INPGNVNT (SEQ ID NO: 11), and STYYRPLDY (SEQ ID NO: 13) respectively and a light chain with three CDRs having the amino acid sequences QSILYSSNQKNY (SEQ ID NO: 10), WASTRE (SEQ ID NO: 12), and HQYMSSYT (SEQ ID NO: 14) respectively. Optionally, the antibody has an IgG1 heavy chain constant region.

In another aspect the inventions provides methods of inhibiting migration of regulatory T-cells (Tregs) to a cytokine secreting tumor in a subject by administering to a subject having a cytokine secreting tumor a humanized anti-CCR4 antibody having a heavy chain with three CDRs having the amino acid sequences GYTFASAW (SEQ ID NO: 9), INPGNVNT (SEQ ID NO: 11), and STYYRPLDY (SEQ ID NO: 13) respectively and a light chain with three CDRs having the amino acid sequences QSILYSSNQKNY (SEQ ID NO: 10), WASTRE (SEQ ID NO: 12), and HQYMSSYT (SEQ ID NO: 14) respectively. Optionally, the antibody has an IgG4 heavy chain constant region. In some aspects the constant region comprises a S228P mutation. The cytokine is CCl2, CCl4, CCL5, CCL17 or CCL22.

The effector T-cells are not substantially depleted. The ratio of effector T cells to regulatory T-cells is modulated, e.g. increased in the tumor or subject. The effector T-cell proliferation is increased or not substantially reduced. The effector T-cell number is increased or not substantially reduced.

In some aspects the regulatory T-cell is a follicular regulatory T-cell.

In various aspects cytokine release from an effector T-cell population is modulated. The cytokine is for example interferon-gamma. In another aspect, an effector polypeptide released from an effector T-cell population is modulated. The effector polypeptide is for example granzyme B or a perforin.

In yet another aspect the invention provides methods of inhibiting tumor cell growth in a subject by administering to a subject in need thereof a humanized anti-CCR4 antibody having a heavy chain with three CDRs comprising the amino acid sequences GYTFASAW (SEQ ID NO: 9), INPGNVNT (SEQ ID NO: 11), and STYYRPLDY (SEQ ID NO: 13) respectively and a light chain with three CDRs comprising the amino acid sequences QSILYSSNQKNY (SEQ ID NO: 10), WASTRE (SEQ ID NO: 12), and HQYMSSYT (SEQ ID NO: 14) respectively. The antibody has an IgG4 heavy chain constant region or an IgG1 heavy chain constant region.

The tumor is a solid tumor or a hematologic tumor. The hematologic tumor is cutaneous T-cell Lymphoma (CTCL), mycosis fungoides (MF), primary cutaneous anaplastic large cell Lymphoma (cutaneous ALCL), Sezary syndrome, or adult T cell Leukemia/Lymphoma (ATLL).

The solid tumor is renal cell carcinoma, breast cancer, lung cancer, ovarian cancer, skin cancer, prostate cancer, colon cancer, cervical cancer, brain cancer, liver cancer, pancreatic cancer, kidney or stomach cancer, Hodgkins disease or glioblastoma multiforme (GBM).

In another aspect, the invention provides a method of vaccinating for an antigen by administering to a subject an antigen and an anti-CCR4 antibody. The anti CCR4 antibody is administered before, at the same time or after administration of an antigen In a further aspect the invention provides methods of inhibiting IL-2 binding to CCR4+ Tregs comprising contacting Tregs with a humanized anti-CCR4 antibody having a heavy chain with three CDRs comprising the amino acid sequences GYTFASAW (SEQ ID NO: 9), INPGNVNT (SEQ ID NO: 11), and STYYRPLDY (SEQ ID NO: 13) respectively and a light chain with three CDRs comprising the amino acid sequences QSILYSSNQKNY (SEQ ID NO: 10), WASTRE (SEQ ID NO: 12), and HQYMSSYT (SEQ ID NO: 14) respectively.

In another aspect the invention provides methods of inducing CD25 cleavage comprising contacting a Treg with a humanized anti-CCR4 antibody having a heavy chain with three CDRs comprising the amino acid sequences GYTFASAW (SEQ ID NO: 9), INPGNVNT (SEQ ID NO: 11), and STYYRPLDY (SEQ ID NO: 13) respectively and a light chain with three CDRs comprising the amino acid sequences QSILYSSNQKNY (SEQ ID NO: 10), WASTRE (SEQ ID NO: 12), and HQYMSSYT (SEQ ID NO: 14) respectively.

In various aspects the humanized anti-CCR4 antibody is a first member of a bispecific antibody. The second member of the bispecific antibody is specific for a tumor associated antigen, a T-cell function modulating molecule, a T-cell receptor polypeptide. The tumor associated antigen is CA-IX, ErbB2 or HVEM. The T-cell function modulating molecule is PD-L1, PD1, CTLA4, GITR, IL21, IL21R, CD160, TIM3, LAG3 or GAL9. The T-cell receptor polypeptide is CD3.

Also provided by the invention are pharmaceutical compositions having a humanized anti-CCR4 antibody in an amount effective to increase the ratio effector T-cells to regulatory T-cells in or associated with a tumor present in a human subject to whom the pharmaceutical composition is administered one or more times. The tumor is for example a solid tumor.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 3. Inhibition of ovarian cancer cells mediated Treg chemotaxis by mAb2-3 in vitro and in vivo. (A) Intracellular chemokine CCL22 staining was performed with (blue lines) or without (red lines) the addition of brefeldin A (BFA) in the culture of ovarian cancer cell lines, IGROV-1, OVCAR-5, and OVCAR-8. (B) In vitro chemotaxis of CD4+ CD25+ Tregs induced by CCL22-expressing ovarian cancer cell supernatant was performed using transwell assay. Treg recruitment was inhibited by mAb2-3 IgG1 and IgG4, but not by control antibodies. (C) The in vivo bioluminescence images of ovarian cancer xenograft mouse model at 18 h post-injection of luciferized CD4+ T cells and (D) $CD4^+$ $CD25^+$ $CD127^{dim/-}$ Tregs. The intensity of the region of interest (ROI) (red circle, xenografted tumor) was further quantified in the left panel. Results were expressed as means±S.D. "*" and "**" represent student's t-test p value<0.05 and 0.01, respectively.

FIG. 8. In vivo distribution of human PBMCs in the presence and absence of mAb2-3. (A) $1\times10^7$ human PBMCs and antibodies were injected into mice intravenously. After 24 hour circulation in vivo, mouse blood were collected and human PBMCs were stained with Pacific Blue conjugated anti-CD3, Brilliant Violet conjugated anti-CD4, APC conjugated anti-CD25, and PE-Cy7 conjugated anti-CD127, gated to distinguish Tregs. (B) The percentage of CD25$^+$ CD127$^-$ Treg was shown the average from three individual mice in each group. *, p value<0.05. (C) Analysis of Tregs after in vivo circulation.

DETAILED DESCRIPTION OF THE INVENTION

The invention is based in part upon the discovery that an anti-CCR4 antibody, mAb2-3 can inhibit regulatory T-cell (Treg) chemotactic activity, restore effector T-cell (Teff) proliferation and deplete $CCR4^+$ Tregs.

One important role of human mAbs in cancer immunotherapy lies in their capacity to reverse the immune dysregulation caused by tumor cell commandeering of surface expression and secretion of proteins that promote immune evasion. The tumor microenvironment contains a plethora of mixed immune cell types that play a paradoxical role in tumor immunosurveillance by either activating anti-tumor responses or promoting tumor progression. Among these tumor infiltrating lymphocytes (TILs) are $CD4^+$ $CD25^+$ $FoxP3^+$ Tregs that have been shown in several malignancies to play a critical role in suppressing local tumor immunity. The recruitment of Tregs to the tumor is mediated through high-level secretion of the CCR4 receptor chemokine CCL22 by tumor cells and microenviornmental macrophages. These CCR4+ Tregs create a favorable environment for dysregulation of local anti-tumor immunity and enhancement of tumor growth. Moreover, the tumor-associated chemokines of CCR4 have been detected in patients with different types of cancer. Thus, the targeted approach of human anti-CCR4 mAb immunotherapy described herein offers significant advantages in improving cancer immunotherapeutic efficacy while simultaneously reducing its side effects.

Figure 1:
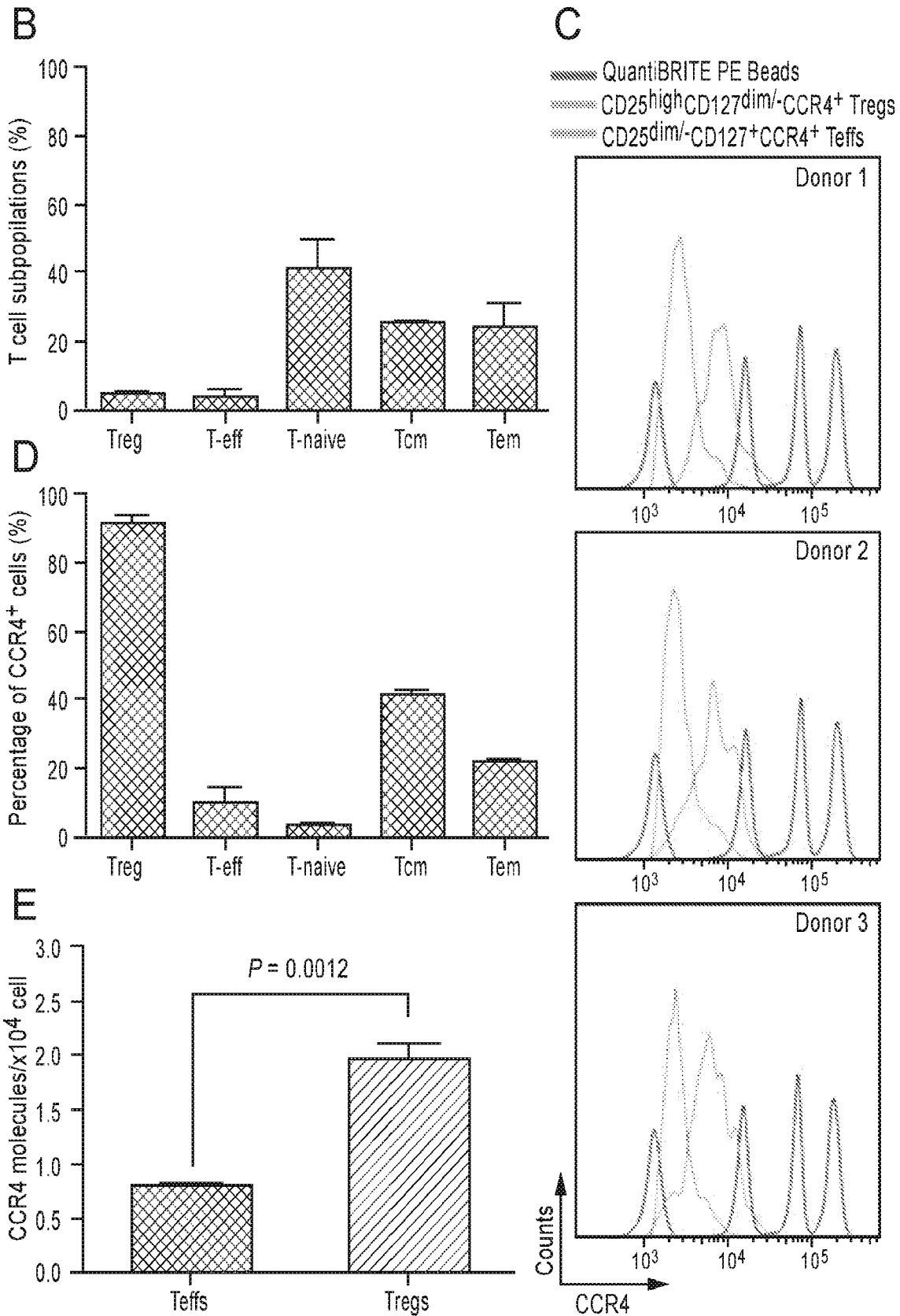
FIG. 1. Identification of CCR4 molecules on CD4+ T cell populations. (A) Gating strategy for identification of human T cell populations and the CCR4-expressing T cell subsets. (B) The percentage of T cell subpopulations. (C) Fluorescence histograms of QuantiBRITE PE beads (red line), $CD25^{high}CD127^{dim/-}CCR4^+$ Tregs (blue line), and $CD25^{dim/-}CD127^+CCR4^+$ T cells (orange line) were performed by flow cytometry in three independent healthy donors. PE beads showed the fluorochrome contained low level (474 PE molecules/bead), medium low level (5,359 PE molecules/bead), medium high level (23,843 PE molecules/bead), and high level (62,336 PE molecules/bead) of PE molecules. (D) The percentage of CCR4+ subsets in each T cell subpopulation. (E) The expression levels of CCR4 molecule on $CD4^+$ $CD25^-$ $CD127^+$ Teffs and $CD4^+$ $CD25^{high}CD127^{dim/-}$ Tregs. All experiments were performed in three independent donors and showed the means±S.E.M.
Figure 2:
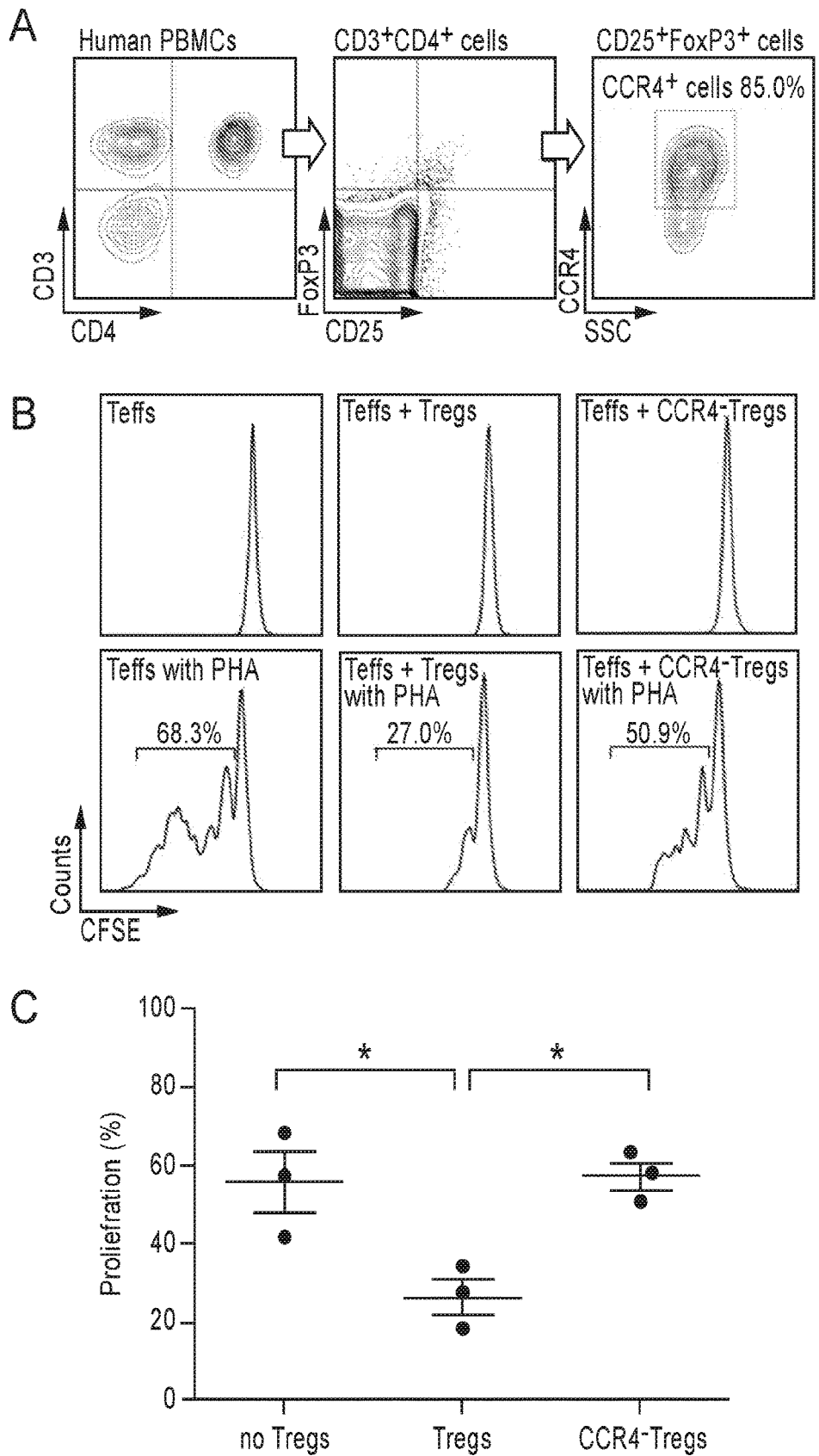
FIG. 2. CCR4+ Treg mediated immunosuppression. (A) Expression of CCR4 on CD4+ CD25+FoxP3+ Tregs was assessed by flow cytometry. Representative fluorescence-activated cell sorter (FACS) plots of CD25 and FoxP3 expression gated on CD3+ CD4+ lymphocytes (left two plots) and CCR4 staining gated on CD25+FoxP3+ lymphocytes (right plot) in healthy donor blood sample. (B) CFSE cell proliferation profiles of CD4+ effector T cells cultured with or without 20 μg/ml PHA and Tregs or CCR4-Tregs (at the ratio of Teff:Treg=10:1) were analyzed using flow cytometry by gating CFSE+ cells. CCR4−Tregs were separated by using mAb2-3-conjugated beads. Percentages represent the proportion of dividing CFSE-labeled CD4+ Teffs after 7 days in culture. Experiments were reproduced in three independent donors. (C) In vitro suppression assay of Teffs in the coculture of CCR4-depleted Tregs. The suppression assay was measured by the proliferation of CFSE-labeled Teffs cocultured in the presence or absence of $CD4^+$ $CD25^+$ $CD127^{dim/-}$ CCR4+ Tregs from three independent healthy donors at the Teff/Treg ratio of 10/1 and stimulated with PHA for 5 days. Percentages of CFSE-diluting Teffs were calculated. Shown are mean±S.E.M. analyzed by two-way ANOVA. value<0.05.
Figure 4:
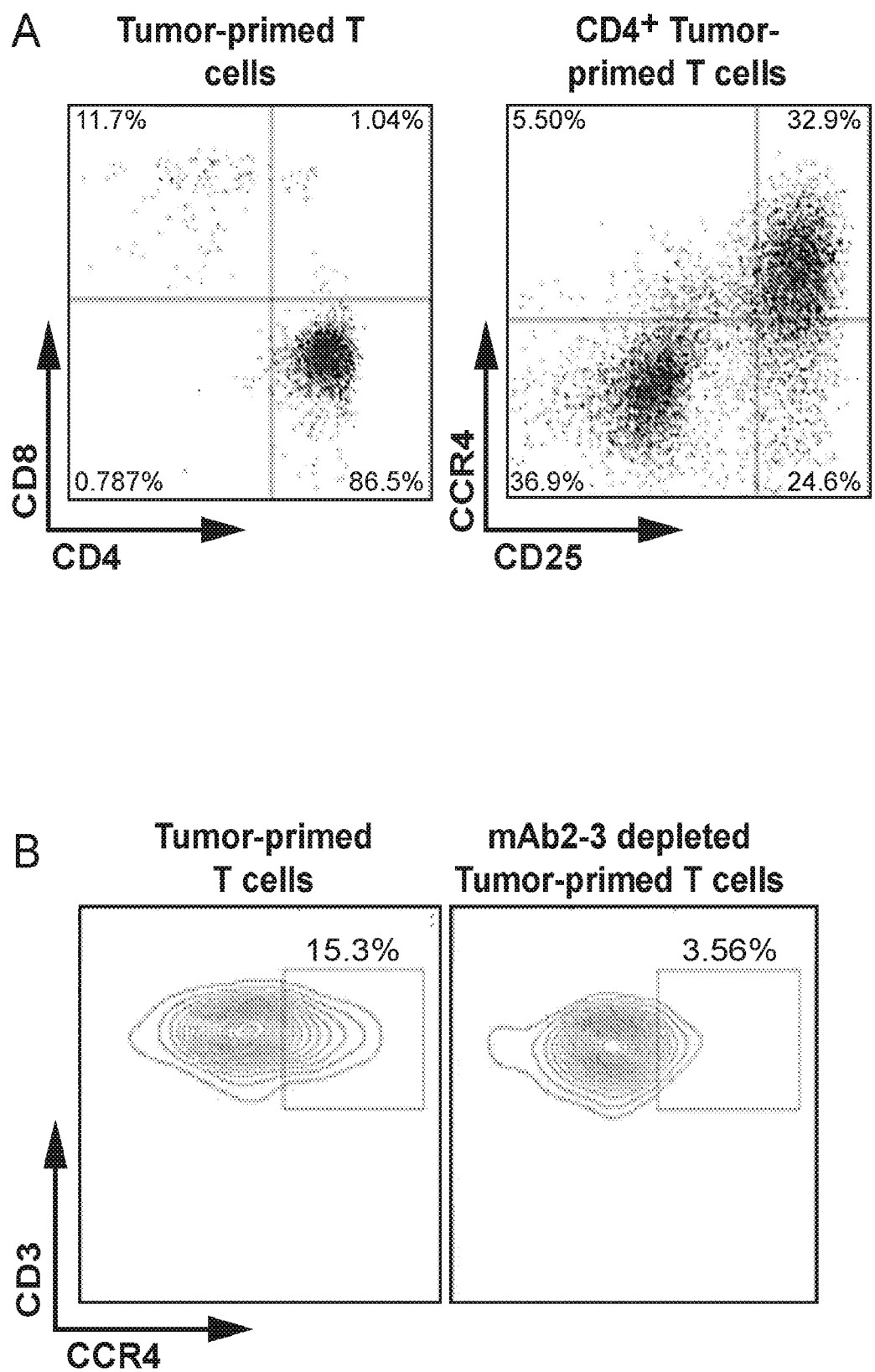
FIG. 4. The activity of tumor-primed T cells on IGROV-1 cells. (A) Tumor-primed T cells were stained by anti-CD3, CD4, CD8, CD25 and (B) CCR4 antibodies. CCR4-depleted tumor-primed T cells by mAb2-3-conjugated beads and T cell subsets in tumor-primed T cells were analyzed by flow cytometry. (C) Tumor-primed T cells and mAb2-3-depleted tumor-primed T cells were incubated with IGROV-1 cells for 24 and 48 hours and then the supernatant were harvested and detected the expression level of IFN-γ. The IFN-γ in the cocultured supernatant was measured by mesoscale discovery (MSD) and showed the folds of the IFN-γ concentration in the tumor-primed T cells cultured supernatant. (D) Intracellular IFN-γ staining of CD4 and CD8 T cells from coculture. Cells were harvested at 48 hours post-coculture; incubated for 6 h in the presence of brefeldin A; stained for CD3, CD4, and CD8; fixed in paraformaldehyde; permeabilized; and stained for intracellular IFN-γ. The cells were gated on lymphocytes by size and CD markers and analyzed by flow cytometry. (E) The cytotoxic activities of tumor-primed T cells and mAb2-3-depleted tumor primed T cells were further detected by LDH ELISA assay. All experiments represented triplicates in each time point with the means±S.D. and performed in two independent experiments. *, , and * represents student's t-test p value<0.05, 0.01, and 0.005, respectively.
Figure 4:
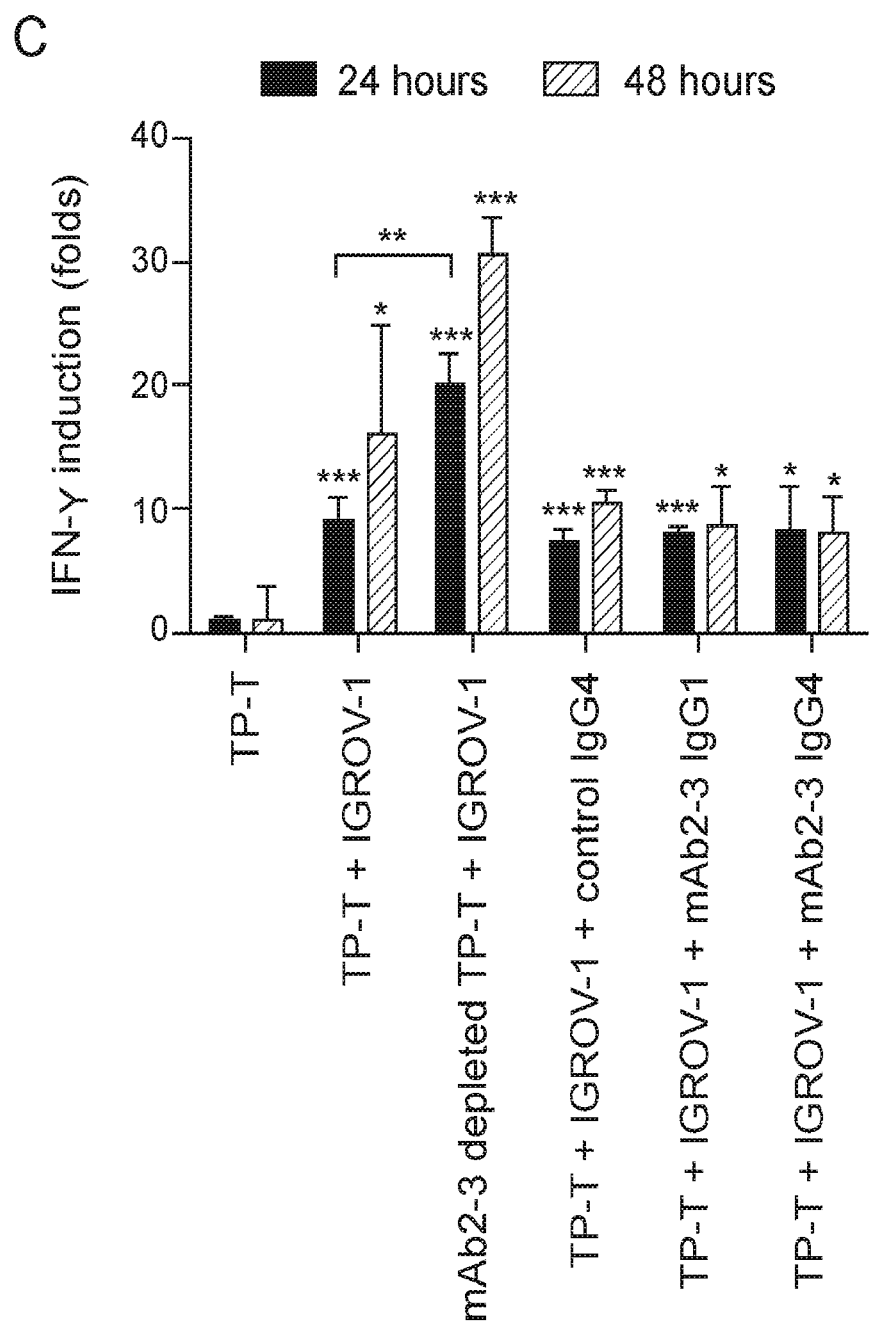
Figure 5:
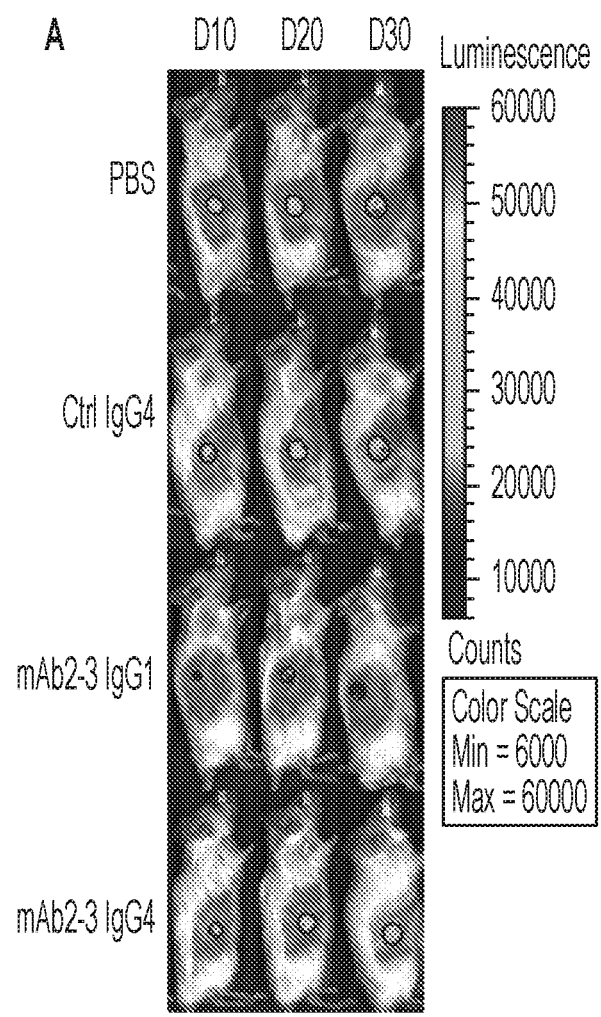
FIG. 5. mAb2-3 mediated the tumor growth inhibition in IGROV-1-xenografted mice reconstructed with IGROV-1-primed T cells. (A) NSG mice were inoculated with $2\times10^6$ luciferased IGROV-1 tumor cells subcutaneously, injected $4\times10^6$ IGROV-1-primed T cells intravenously, and treated with anti-CCR4 antibodies. Tumor growth curves of luciferased IGROV-1 human ovarian carcinoma tumor xenografts in NSG mice were measured. Mice were treated with 3 mg/kg of control IgG4 (n=2), mAb2-3 IgG1 (n=3), and mAb2-3 IgG4 (n=3) and equal volume of PBS (n=2). Antibodies were administered intravenously twice a week for 5 weeks. Mice were imaged using an IVIS imaging system every 10 days. Color scale: luminescent signal intensity: blue, least intense signal; red, most intense signal. (B) Luciferase signals of tumor tissues in each group were quantified. (C) Tumor size and (D) body weight in mice treated with antibodies were measured twice a week. (E) Tumor tissue and (F) tumor weight were harvested and measured. Bar scale, 1 cm. *, p<0.05; ***, p<0.005; p value was calculated with two-way ANOVA. All data were shown the means±S.E.M.
Figure 7:
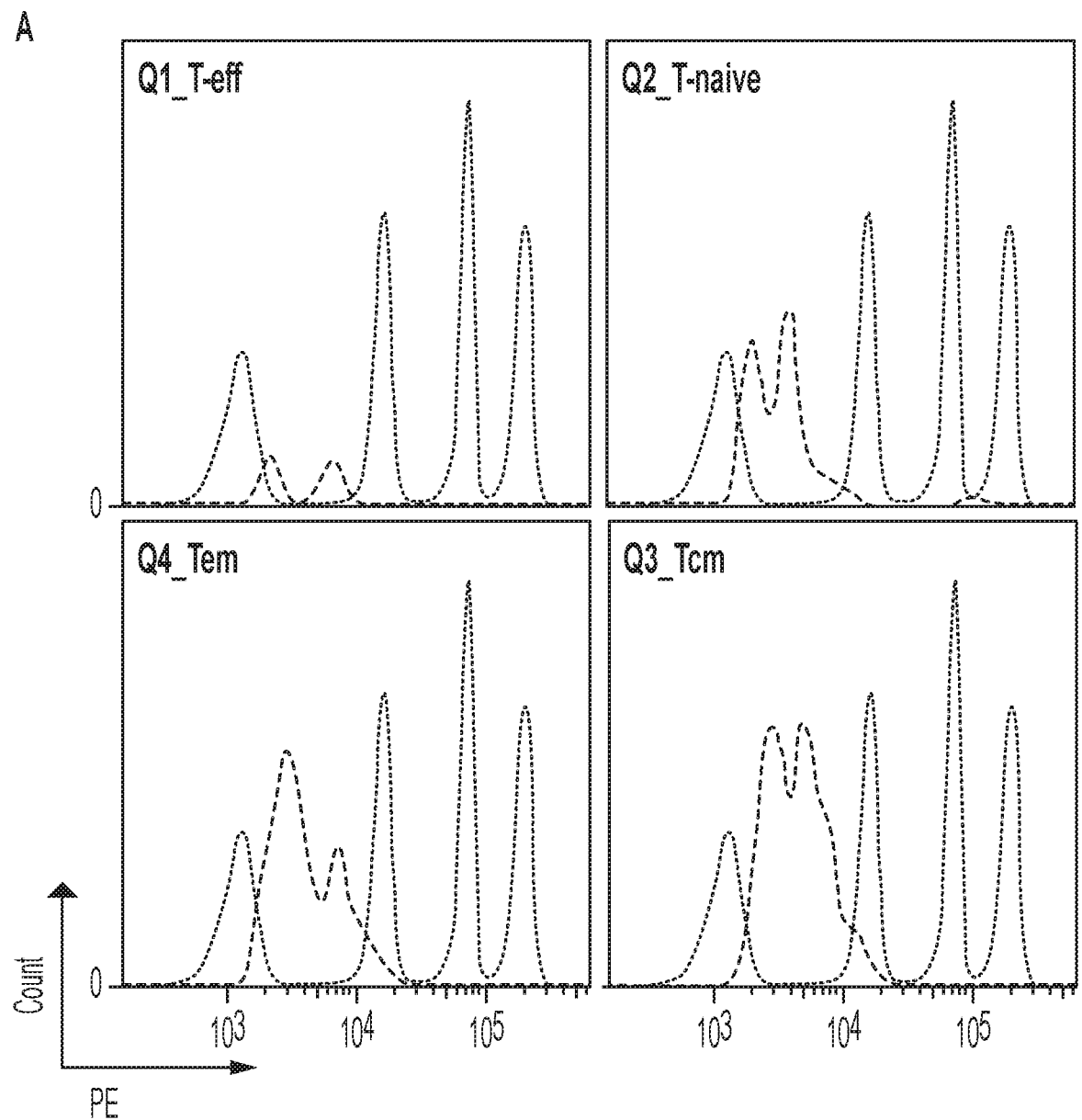
FIG. 7. Representative flow cytometry plots for human peripheral blood T cells and phycoerythrin (PE)-conjugated beads. (A) The CD3$^+$ CD4$^+$ T cells were gated and stained with PE-Cy5 conjugated anti-CD45RA and PerCp-Cy5 conjugated anti-CCR7 antibodies to distinguish Tcms, Tems, Teffs, and Tnaïve (as shown in FIG. 1). CD4$^+$ CD25$^-$ CD127$^+$CCR4$^+$ T cell subpopulations were gated for further analysis. Fluorescence histograms of PE beads and T cell subpopulations were shown in red and blue lines, respectively. (B) Calibration curve relating PE fluorescence to the number of PE molecules per bead. (C) The expression levels of CCR4 molecule on T cell subpopulations. All experiments were performed in three independent donors and showed the means±S.D.
Figure 13:
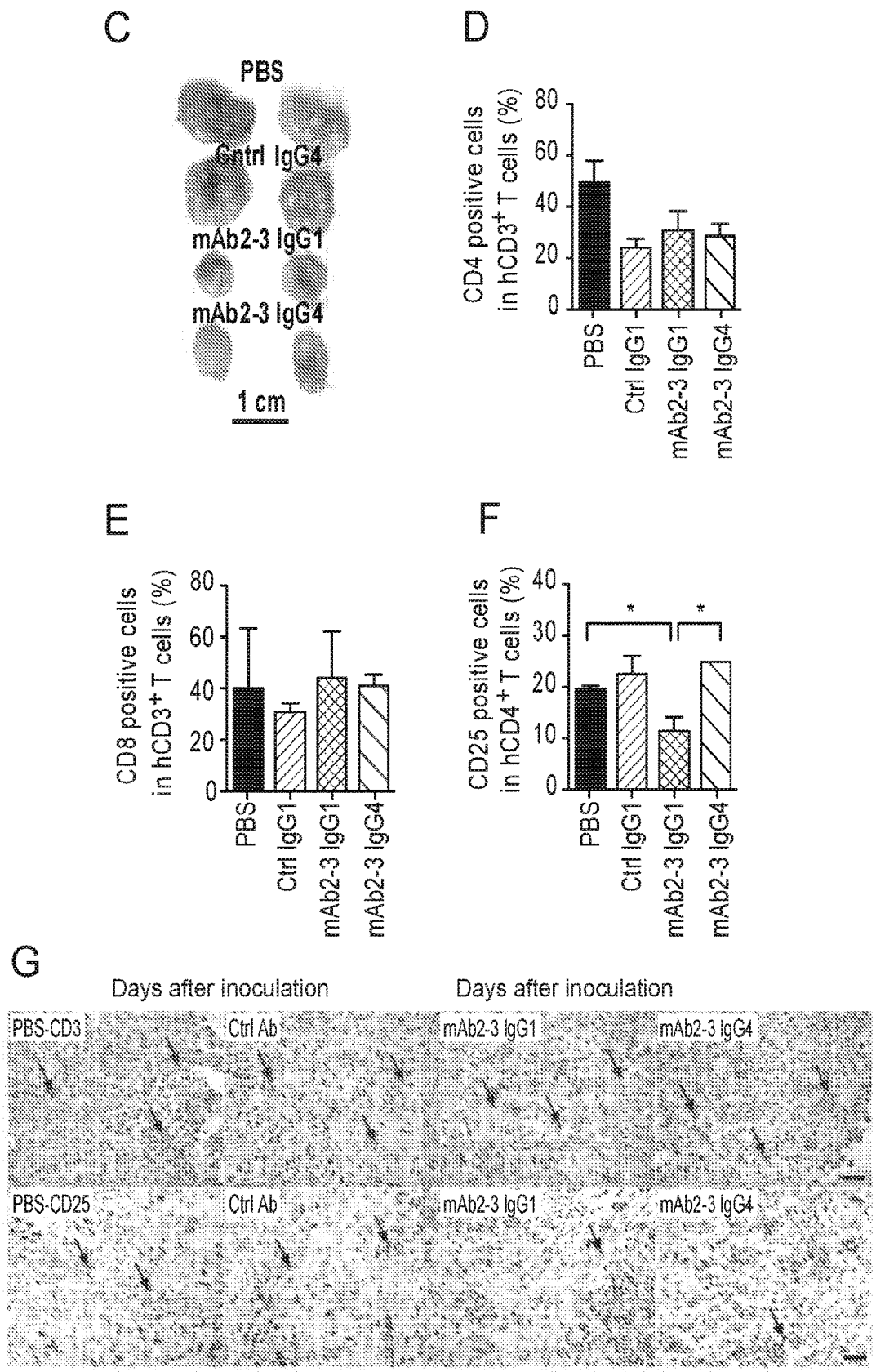
FIG. 13. mAb2-3 mediated tumor growth inhibition in large-scale IGROV-1-xenografted mice bearing IGROV-1-primed T cells. (A) NSG mice were inoculated with $5\times10^6$ IGROV-1 tumor cells subcutaneously, injected $1\times10^7$ IGROV-1-primed T cells intravenously, and treated with anti-CCR4 antibodies. Tumor growth curves of IGROV-1 human ovarian carcinoma tumor xenografts in NSG mice were measured. Mice were treated with 3 mg/kg of control IgG4 (n=2), mAb2-3 IgG1 (n=2), mAb2-3 IgG4 (n=2) and equal volume of PBS (n=2). Antibodies were administered intravenously twice a week for 4 weeks. Tumor size and (B) body weight in mice treated with antibodies were measured once a week. (C) Tumor tissues were harvested. Bar scale, 1 cm. (D) Mouse PBMCs were stained by anti-human CD3, CD4, (E) CD8, and (F) CD25 antibodies and analyzed using flow cytometry. *, P<0.05; **, P<0.01; p value were calculated with two-way ANOVA; black and grey asterisks indicate respectively mAb2-3 IgG1 and IgG4 compared to control groups. All data were shown as means±S.E.M. (G) Immunohistochemistry staining was performed using anti-CD3 (upper panel) and anti-CD25 (lower panel) antibodies in tumor tissues of each group. The dark red staining membrane (arrows) represents CD3 or CD25 TP-T cell in tumor. Bar scale, 50 μm.

As described in detail in the Examples below, the in vitro and in vivo activity of a human anti-CCR4 mAb, mAb2-3, against Tregs was examined. About 85% of $CD4^+$ $CD25^+$ $FoxP3^+$ Tregs overexpress CCR4 compared to Teffs (FIGS. 1 and 7) and they are responsible for the majority of suppressor activity. In addition, removal of $CCR4^+$ Tregs by mAb2-3 restores Teff proliferation (FIG. 2). In vitro studies demonstrated that mAb2-3 can inhibit Treg chemotactic activity to CCL22-expressing OvCA cells. In a humanized mouse model bearing a OvCA xenograft, mAb2-3 showed therapeutic capability to modulate human Treg function and enhance anti-tumor activity (FIGS. 4, 5, and 13).

Figure 9:
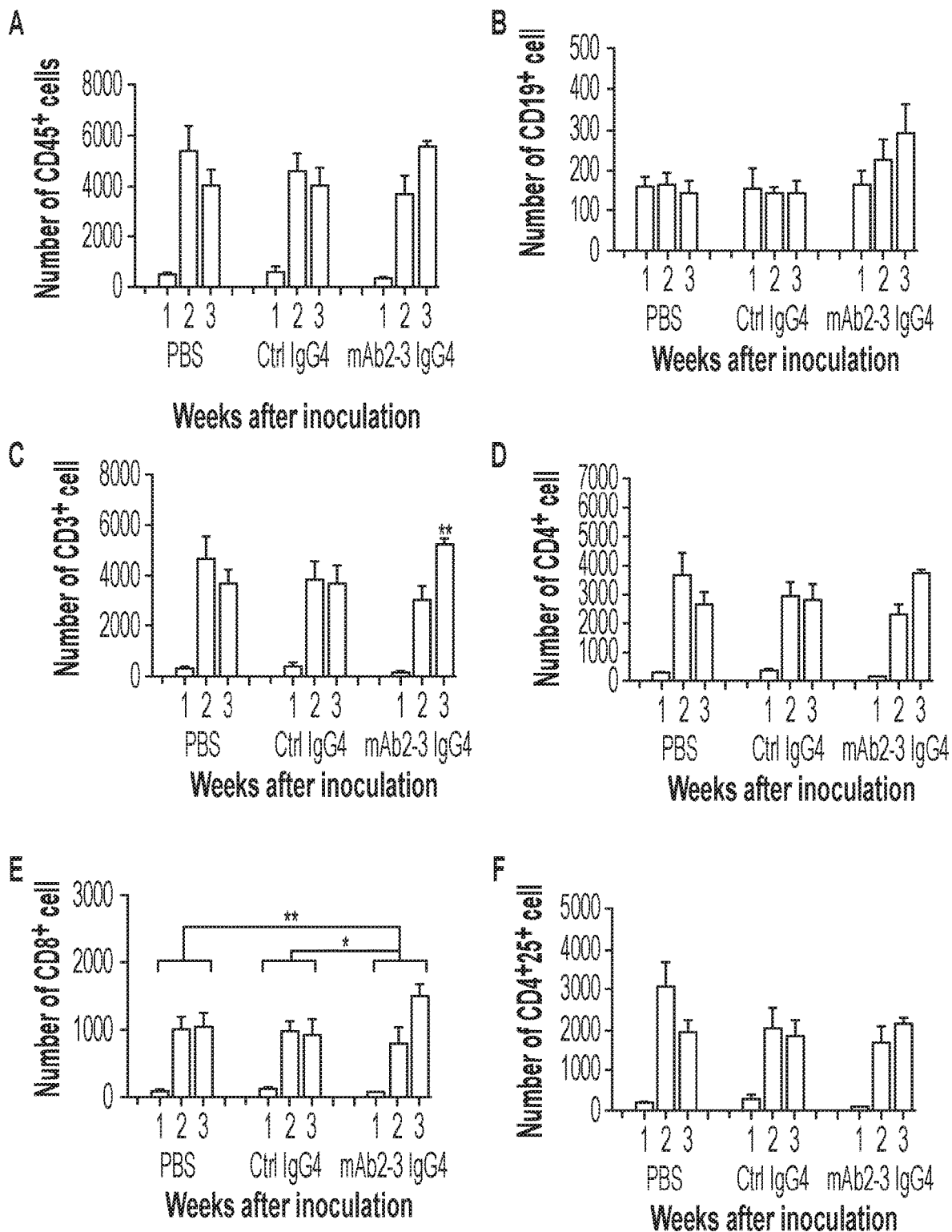
FIG. 9. In vivo response of human PBMCs to mAb2-3 IgG4 in a huPBL-NSG animal model. (A) $10^7$ freshly isolated human PBMCs were injected intravenously via the tail vein into adult NSG immunodeficiency mice. The huPBL-NSG mice were received 1 mg/kg antibodies through tail vein twice a week. Peripheral blood was collected from huPBL-NSG mice weekly and stained with anti-human specific antibodies for human CD45, (B) CD19 with CD45, (C) CD3 with CD45, (D) CD4 with CD3 and CD45, (E) CD8 with CD3 and CD45, and (F) CD25 with CD3 and CD45, and quantified per $10^4$ PBMCs by flow cytometry. (G) The percentages of CD3$^+$ CD4$^+$ CD25$^+$ CD127$^-$ cells in CD45$^+$ cells from blood were examined each week in different treatment. (H) The percentage of CD3$^+$ CD4$^+$ CD25$^+$ CD127$^-$ cells in CD45$^+$ cells from blood, spleen, and bone marrow are shown at the third week. Two-way ANOVA test was performed. Each data point represents the average (n=6 NSG mice, 2 PBMC donors) ±S.E.M. * and **, p value<0.05 and 0.01, respectively.
Figure 10:
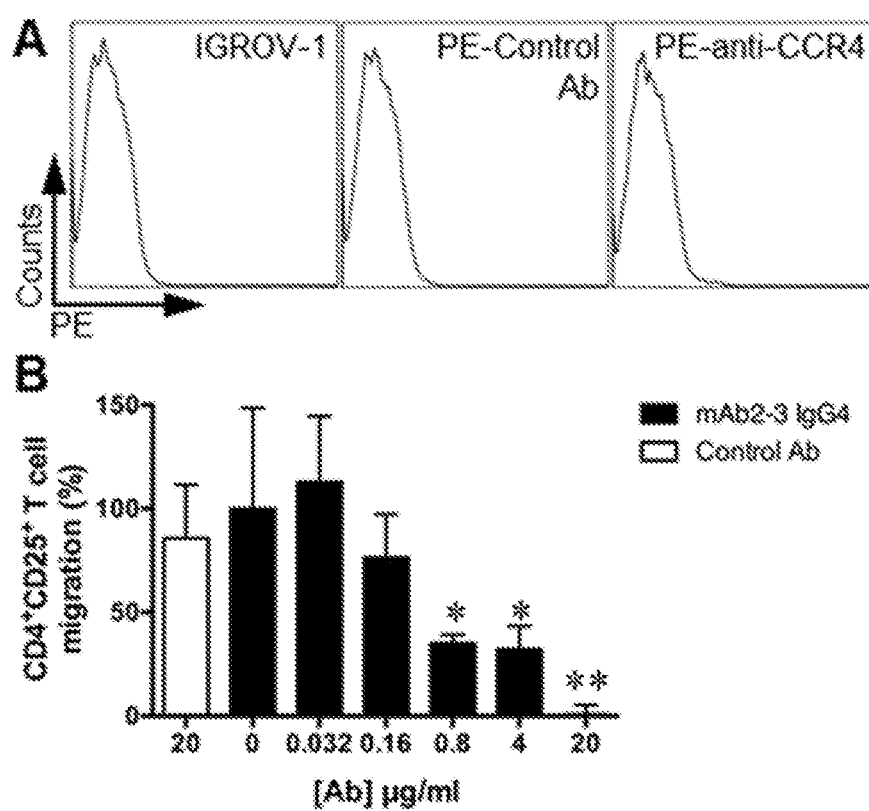
FIG. 10. mAb2-3 inhibited the chemoattraction mediated by CCL22. (A) The expression of CCR4 on IGROV-1 ovarian cancer cells. (B) mAb2-3 effectively inhibited chemotaxis of CD4$^+$ CD25$^-$ and (C) CD4$^+$ CD25$^+$ T cells to CCR4 ligand, CCL22 in a dose-dependent manner.
Figure 11:
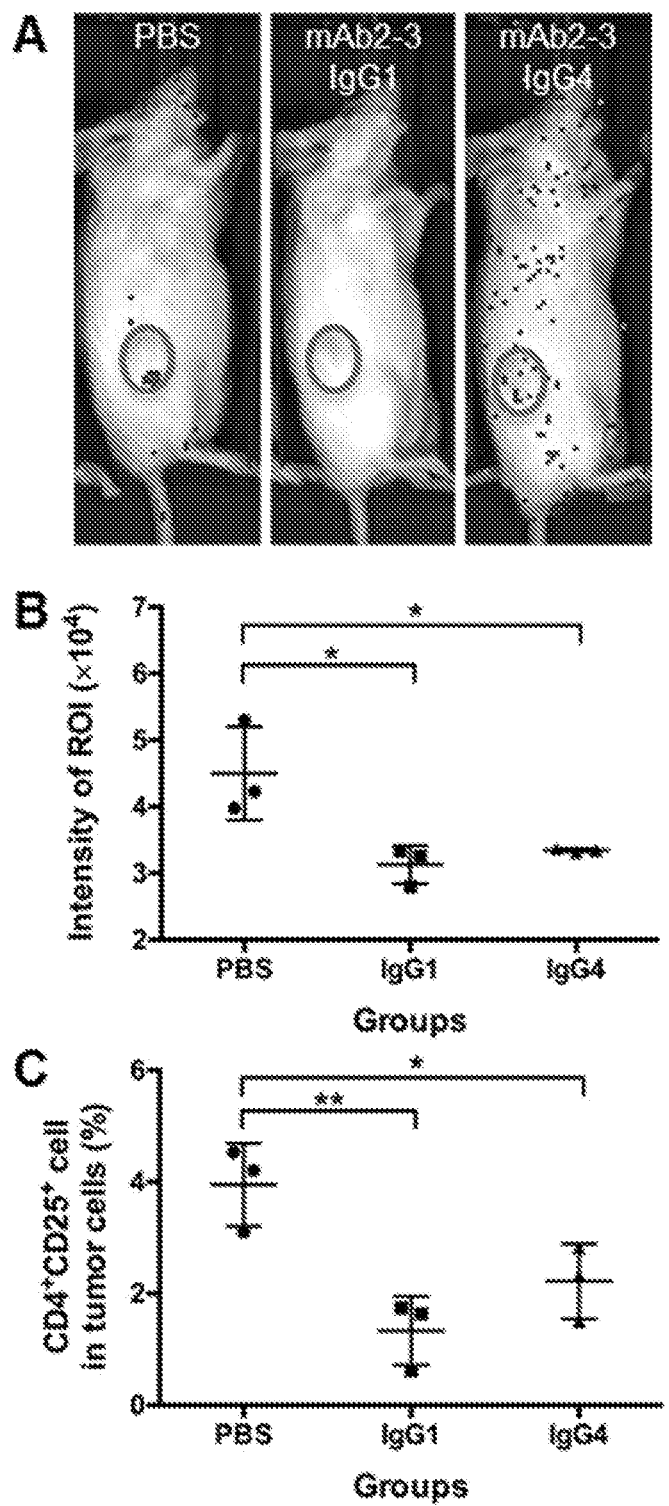
FIG. 11. Chemoattraction of human lymphocytes by CCL22-secreting ovarian cancer cells is inhibited by mAb2-3. (A) The images show in vivo bioluminescence images of ovarian cancer xenograft mouse model at 48 hours (imaging) post-injection of luciferized CD4$^+$ CD25$^+$ CD127$^{dim/-}$ T cells. (B) The quantification of intensity of ROI (red circle, xenografted tumor) was shown that mAb2-3 inhibits Tregs recruitment to tumor tissue. (C) Tumor tissues were harvested, digested by collagenase, and then stained by anti-CD3, CD4, and CD25 antibodies. CD3$^+$ CD4$^+$ CD25$^+$ T cells were analyzed and counted by flow cytometry and shown as the percentage of total cells from tumor tissues.

It has been previously demonstrated that mAb2-3 IgG1 exhibits potent antibody-dependent cellular cytotoxicity (ADCC) and complement-dependent cytotoxicity (CDC) activities in vitro and in vivo against CCR4 expressing tumors (18,42). (See, WO 2009/086514 and WO 2013/166500 the contents of which are incorporated by reference in their entireties). In the Examples provided herein, the biological functions of both IgG1 and IgG4 isotypes of mAb2-3 were tested and showed similar capacity to block CCR4$^+$Treg migration in vitro (FIGS. 3B and 10B) but revealed their different mechanisms of action in vivo. In particular, mAb2-3 IgG1 induced a profound immunodepletion of Tregs as evidenced by in vivo clearance studies (FIGS. 3D and 8B) and decreased tumor cell infiltration (FIG. 11). In OvCA xenograft studies, mAb2-3 IgG1 treatment led to marked inhibition of tumor cell growth (FIGS. 5 and 13) and in two animal studies the mice showed significant weight loss (FIGS. 5D and 13B). In contrast, the IgG4 isotype appeared to work primarily through ligand-receptor blockade (FIGS. 3, 9, and 11). In vivo trafficking studies showed that this isotype caused blockade of Treg chemotaxis to CCL22 secreting OvCA tumors and a decrease in tumor cell infiltration (FIG. 11). The IgG4 isotype also caused a slower and less complete depletion of Tregs (FIG. 9G). The slower in vivo clearance observed for IgG4-mediated depletion of Tregs may be through a different mechanism of action as a recent report showed that IgG4 isotype has similar ADCP capacity to IgG1 (43). In addition, mAb2-3 IgG4 treatment showed lesser anti-tumor effect however, the mice had no weight loss (FIGS. 5D and 5F). These results suggest that the two mAb2-3 isotypes may have unique roles at different stages of OvCA disease with IgG4 treatment having a possibly preferred role at earlier stages when tumor burden is smaller and immune dysfunction is more easily reversed.

Figure 6:
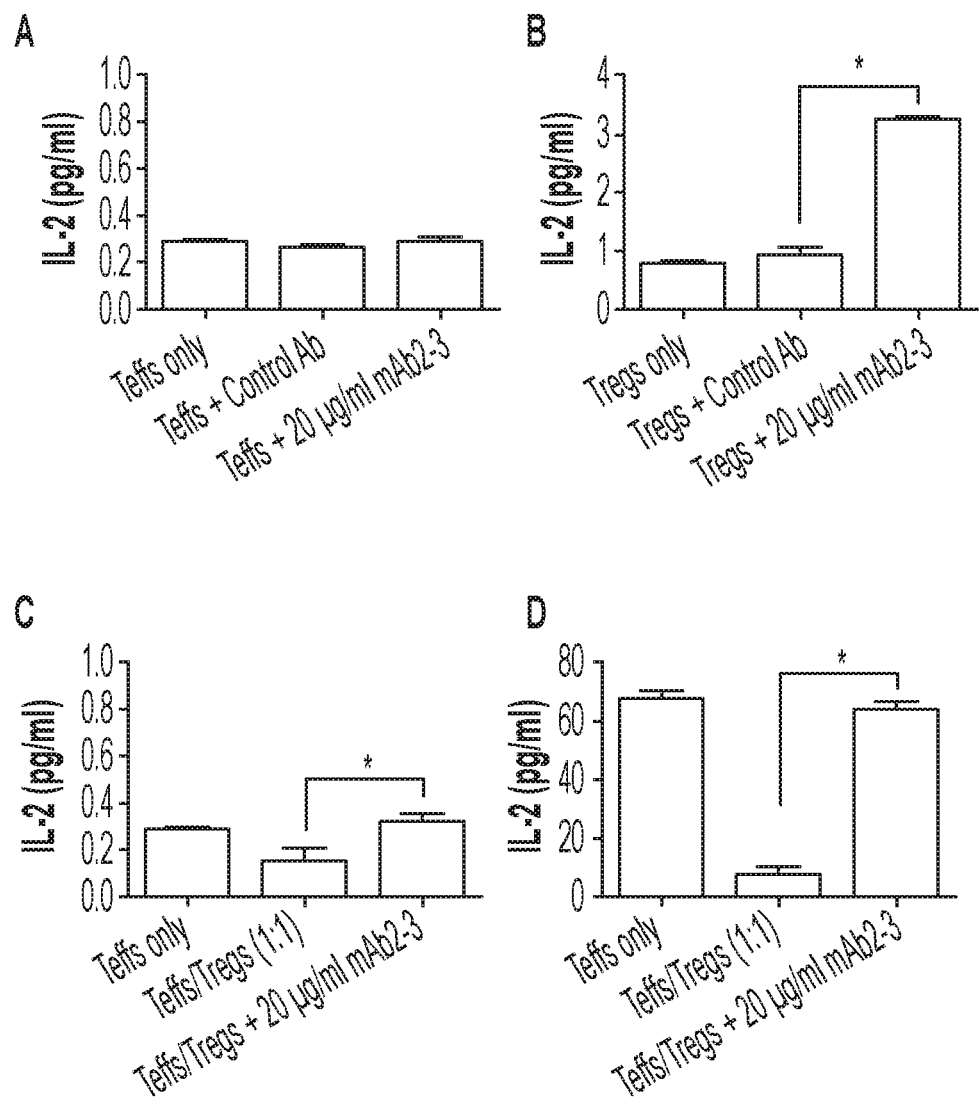
FIG. 6. The intermediation of mAb2-3 in interaction between IL-2 and CD25. (A) In the absence of exogenous IL-2, endogenous IL-2 levels in $1\times10^4$ CD4$^+$CD25$^-$ Teffs cultured supernatants incubated with or without mAb2-3 were analyzed by ELISA. (B) CD4$^+$ CD127$^{dim}$CD49d$^-$ Tregs (3000/reaction) were incubated with 0.25 IU/ml of exogenous IL-2 in the presence and absence of 20 µg/ml of mAbs and 0.5/1 µg/ml of plate-bound anti-CD3/28 antibodies. Bars represent ±S.D. (C) In the absence of exogenous IL-2, endogenous IL-2 concentration was shown from $1\times10^4$ Teffs alone or with Tregs and treated with 20 µg/ml of mAb2-3. Bars represent ±S.D. (D) The concentrations of IL-2 in supernatants from Teffs and Tregs coculture treated with mAb2-3 in the presence of 4 IU/ml of exogenously added IL-2. Bars represent ±S.D. (E) In the presence of exogenous IL-2 (20 IU/ml), the IL-2 concentrations of supernatants from $2\times10^5$ Mac-1 cells treated with or without antibodies (mAb2-3 or anti-CD25, including anti-TAC and control mAbs) were detected by ELISA. Bars represent ±S.D. (F) In vitro cell survival assay was performed by measuring the viability dye in cultured Tregs treated with the presence or absence of 0.5 IU/ml IL-2, 20 µg/ml mAb2-3 IgG1, and 20 µg/ml control IgG1 for 5 days. The normalized percentage of dead Tregs from different groups among spontaneous death Tregs was shown. Each dot indicates an individual donor in each group. Bars represent means±S.E.M. "" and "*" represent p value<0.01 and 0.005, respectively, by using student's t-test.
Figure 17:
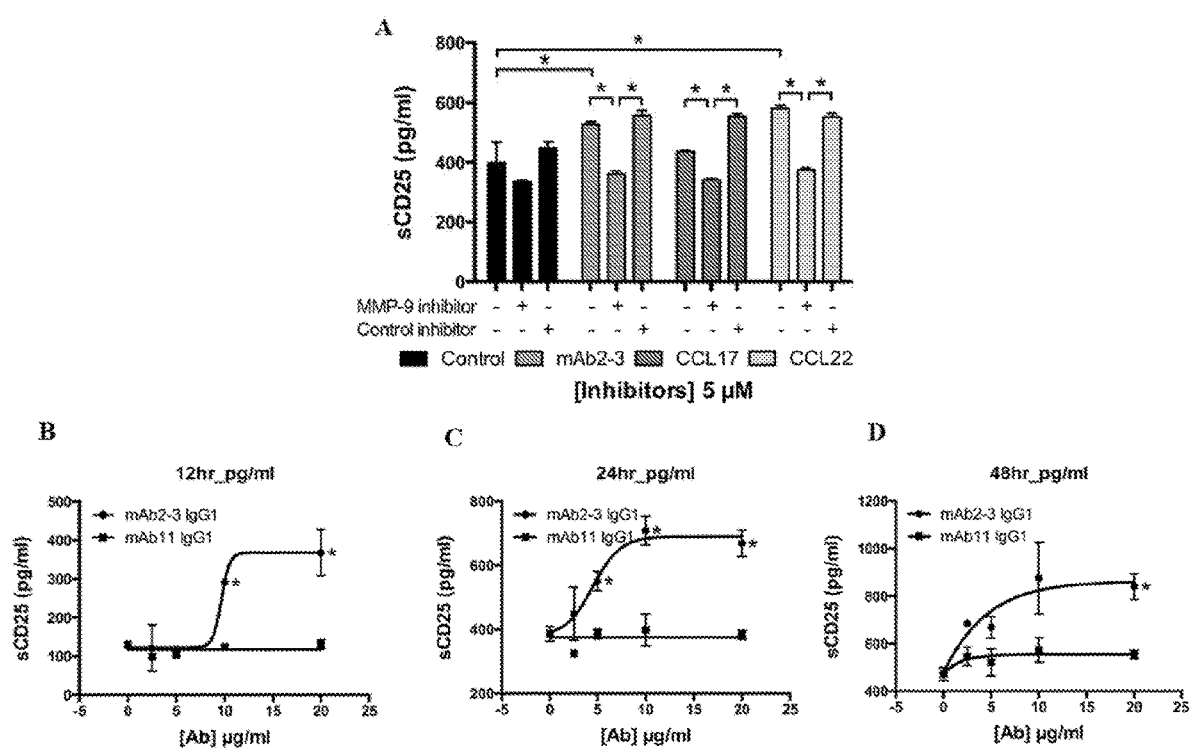
FIG. 17 mAb2-3 and chemokine induced shedding of CD25 from Mac-1 cells (A) Mac-1 cells were incubated with mAb2-3, CCL17, or CCL22 in the presence or absence of MMP-9 inhibitor or with negative control for MMP inhibitors. After 24 hours incubation, culture supernatants were harvested and tested the concentration of soluble CD25 by ELISA. Bars represent ±S.E.M. (B) The concentration of soluble CD25 in 12-hour, (C) 24-hour, and (D) 48-hour cultured supernatant of Mac-1 cells treated with mAb2-3 or control mAbs was investigated with ELISA. The figure shows soluble CD25 concentration expressed as pg/ml in the cultured supernatant. Bars represent ±S.E.M. "*" indicates p value<0.05 by student's t-test.
Figure 18:
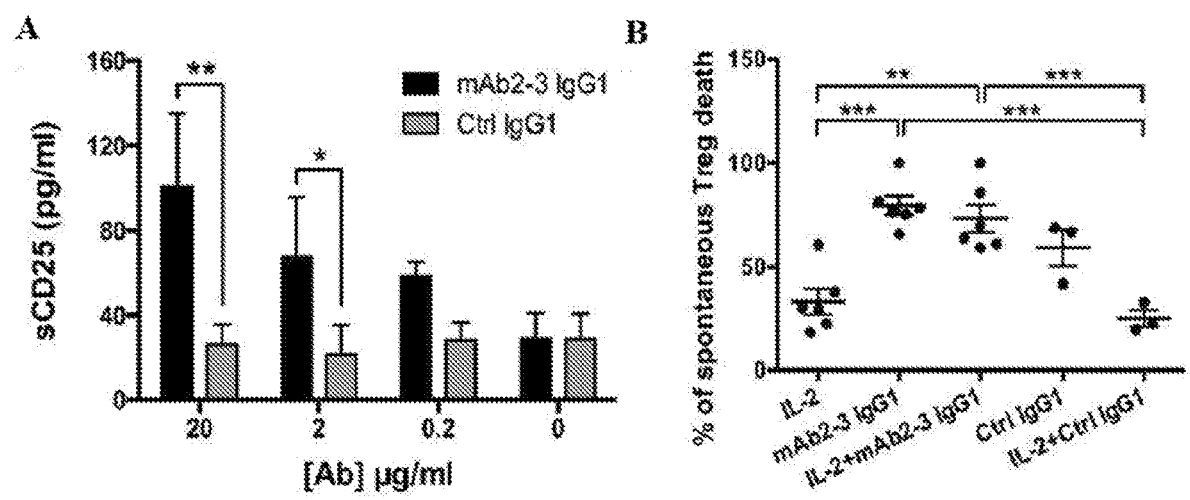
FIG. 18. mAb2-3 induced CD25 shedding from Tregs Tregs were incubated with mAb2-3 and control IgG1. After 48 hours incubation, culture supernatants were harvested and tested the concentration of soluble CD25 by ELISA. (A) The concentration of soluble CD25 (sCD25) in 48-hour cultured supernatant of Tregs treated with mAb-2-3 or control IgG1 was investigated with ELISA. The data presented are the average from three independent donors. Bars represent ±S.E.M. "*" and "**" represent p value<0.05 and 0.01, respectively, by using two-way ANOVA. (B) The results are presented from in vitro cell survival assays that were performed by measuring the viability dye in cultured Tregs treated with the presence or absence of IL-2, mAB2-3 IgG1, and control IgG1 for 5 days. The normalized percentage of Treg death from the different groups among spontaneous death of Tregs is shown. Bars represent ±S.E.M. "*" and "**" represent p value<0.01 and 0.005, respectively, by using Student's t-Test.
Figure 19:
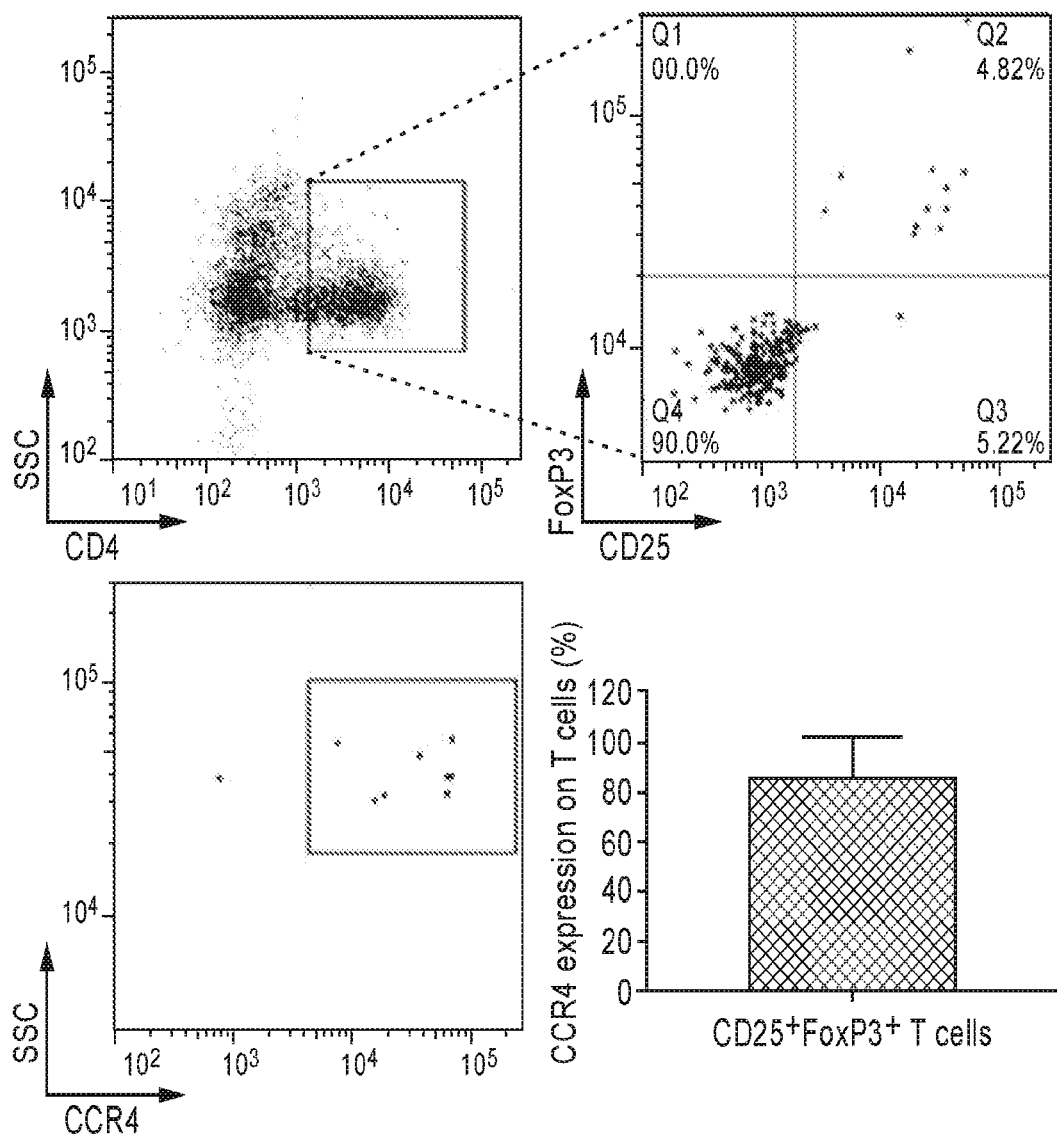
FIG. 19. Representative phenotypic analysis of CCR4 expression in $CD4^+$ $CD25^+FoxP3^+$ T cells of Macaque PBMCs Freshly isolated PBMCs were stained for CD4, CD25, CCR4 and intracellular FoxP3. CCR4 expression was analyzed in the $CD4^+$ $CD25^+FoxP3^+$ population. The average CCR4 expression on Tregs was calculated in three independent macaques.

Additionally, it was shown that mAb2-3 can inhibit IL-2 binding to CCR4$^+$ IL-2R$^+$ Mac-1 and Treg cells (FIG. 6), but did not did not cross-bind to IL-2R subunits alone or in combination using transfected 293T cells. With Mac1 cells, mAb2-3 treatment led to enhanced cleavage of sCD25, a property that was shared by the CCR4 ligands CCL22 and CCL17 (FIG. 18A and FIG. 17 B-D). This shared activity suggests that mAb2-3 has agonist activity and triggers cell activation which results in CD25 cleavage. Studies of CCR4 signaling through CCL22/CCL17 binding have shown evidence of PI(3) kinase/AKT activation (25,26). In addition, distinct conformations of CCR4 have been reported to respond differently to the two ligands, a property that is supported by our evidence that CCL22 and mAb2-3 are more potent activators of sCD25 cleavage than is CCL17 (FIG. 17A) (44,45). High level CD25 expression on Tregs leads to formation of the trimeric high affinity IL-2 receptor that supports greater IL-2 binding which has been shown to be required for survival (46). It is possible that the increased cleavage of CD25 will result in decreased affinity for IL-2 binding to Tregs and the released sCD25 may be associated with blockade of IL-2 uptake by Tregs and their decreased survival (FIGS. 6A-F) (47).

Data presented herein demonstrates that circa 85% of peripheral blood CD4+CD25+FoxP3+ Tregs overexpress CCR4 compared to Teffs and they are responsible for the majority of suppressor activity. In vitro studies demonstrated that CCR4+ Treg depletion by mAb2-3 inhibits Treg chemotactic activity to CCL22-expressing ovarian cancer (OvCA) cells and restores Teff proliferation and anti-OvCA immunity. In a humanized mouse model bearing an OvCA xenograft, both mAb2-3 IgG1 and IgG4 isotypes showed therapeutic capability to modulate human Treg function and enhance anti-tumor activity.

The data presented here also demonstrate that mAb2-3 treatment also leads to blockade of IL-2 uptake by Tregs and inhibition of IL-2-mediated survival which may play a role in the in vivo anti-tumor effects seen with non-immunodepleting mAb2-3 IgG4.

The biological functions of both IgG1 and IgG4 isotypes of mAb2-3 were tested and showed similar capacity to block CCR4+Treg migration in vitro but revealed their different mechanisms of action in vivo. In particular, mAb2-3 IgG1 induced a profound immunodepletion of Tregs as evidenced by in vivo clearance studies and decreased tumor cell infiltration. In OvCA xenograft studies, mAb2-3 IgG1 treatment led to marked inhibition of tumor cell growth and in two animal studies the mice showed significant weight loss. In contrast, the IgG4 isotype appeared to work primarily through ligand-receptor blockade. In vivo trafficking studies showed that this isotype caused blockade of Treg chemotaxis to CCL22 secreting OvCA tumors and a decrease in tumor cell infiltration. The IgG4 isotype also caused a slower and less complete depletion of Tregs.

Methods of Treatment

The invention provides for both prophylactic and therapeutic methods of treating a subject at risk of (or susceptible to) a cancer, or other diseases or disorders by administering an anti-CCR4 antibody. Such diseases or disorders include but are not limited to, e.g., those diseases or disorders associated with regulatory T cell mediated immunosuppression. By regulatory T cells it is meant to include Treg and/or follicular regulatory T cells ($T_{FR}$). Administration of a prophylactic agent can occur prior to the manifestation of disease such that the disease is prevented or, alternatively, delayed in its progression. The invention further provides methods of vaccination in which an CCR4 antibody is include in or administered in conjunction with an antigen. The CCR4 antibody act as an adjuvant to increase the immune response to the antigen by depleting regulatory T cells and/or increasing effector T-cell proliferation.

For example, the methods are used to deplete regulatory T-cells (Tregs and or $T_{FR}$) and or inhibit the migration (e.g, chemotaxis) of regulatory T-c ell to a cytokine secreting tumor by contacting a cell or administering to a subject a CCR4 antibody. The cytokine secreting tumor secretes CCL1, CCL4, CCl5, CCL17 and/or CCL22. When the CCR4 antibody is used to deplete regulatory cells, the antibody preferably has an IgG1 heavy chain constant region. When the CCR4 antibody is used to inhibit migration of a regulatory T-cell, the antibody preferably has an IgG4 heavy chain constant region.

In various embodiments the effector T-cells are not substantially depleted By "not substantially depleted" it is meant that no more than 1%, 2%, 3%, 4%, 5%, 10%, 15%. 20%, 25% effector T-cells are depleted. In other embodiments effector T-cell proliferation and or number is increased or not substantially reduced. By "not substantially reduced" it is meant that effector T-cells proliferation and/or is not reduced more than 1%, 2%, 3%, 4%, 5%, 10%, 15%. 20%, 25% compared to untreated cell population.

In other embodiments the methods are uses to increase effector T-cell proliferation. Effector T-cell proliferation is increased 1%, 2%, 3%, 4%, 5%, 10%, 15%. 20%, 25%, 50%, 75%, 80%, 85%, 90%, 95% or more compared to an untreated cell population.

In other embodiments the methods modulate (e.g., increase), the ratio of effector T cells to regulatory T-cells in the tumor or subject. The ratio is increases 1, 2, 3, 4, 5 or more fold.

The methods modulate cytokine (e.g., interferon-gamma) or effector polypeptide (e.g., granzyme B or a perforin) release from an effector T-cell population. By modulate it is meant an increase or decrease cytokine or effector polypeptide release. Cytokine or effector polypeptide release is increased of decrease 1%, 2%, 3%, 4%, 5%, 10%, 15%, 20%, 25%, 50%, 75%, 80%, 85%, 90%, 95% or more compared to an untreated cell population.

In another aspect, tumor cell growth is inhibited or slowed by contacting a cell or administering to a subject with a CCR4 antibody. For example, the tumor is a hematologic cancer such cutaneous T-cell Lymphoma (CTCL), mycosis fungoides (MF), primary cutaneous anaplastic large cell Lymphoma (cutaneous ALCL), Sezary syndrome, or adult T cell Leukemia/Lymphoma (ATLL).

Alternatively, the tumor is a solid tumor such as renal cell carcinoma, breast cancer, lung cancer, ovarian cancer, prostate cancer, colon cancer, cervical cancer, brain cancer, skin cancer (e.g., melanoma), liver cancer, pancreatic cancer Hodgkins disease, glioblastoma mutiforme (GBM) or stomach cancer. In particular embodiments, the cancer is ovarian cancer or melanoma.

Inhibiting or slowing tumor growth increase the survival of a subject having the tumor. Survival is increased by 1, 2, 3, 4, 5, or more years.

In a further aspect, the invention provides methods of inhibiting IL-2 binding to $CCR4^+$ regulatory T cells or inducing CD25 cleavage by contacting the regulatory T cell with a CCR4 antibody. The loss of IL-2 binding through CD25 results in metabolic starvation due to the dependency of IL-2 for regulatory T cells survival thereby inducing regulatory T cells death. An increase of regulatory T cells increases the ratio of effector T-cells to regulatory T cells.

In some aspects the CCR4 antibody uses in the above described methods has an IgG1 or IgG4 heavy chain constant region. In some embodiments the heavy chain constant region has one or more mutations. For example the IgG4 constant region has a S228P mutation.

In particular embodiments, of the invention the subject both a CCR4 antibody with a IgG1 heavy chain constant region and a CCR4 antibody with a IgG4 heavy chain constant region. Alternatively, the subject is selected to receive CCR4 antibody with a IgG1 heavy chain constant region or a CCR4 antibody with a IgG4 heavy chain constant region depending upon the disease stage. For example, it may be advantageous for a patient in the early stage of a disease to receive treatment with a CCR4 antibody with a IgG4 heavy chain constant region as the tumor burden is smaller and the immune dysfunction is more easily reversed. In contrast, when a patient has a later stage of a disease, e.g., high tumor burden it may be advantageous for the subject to receive treatment with a CCR4 antibody with a IgG1 heavy chain constant region The cell is any cell that expresses CCR4. For example the cell is a T-cell. T cell includes regulatory T cell, follicular regulatory T cells, and effector T cells.

CCR4 Antibodies

CCR4 antibodies are known in the art and are suitable for use in the methods of the inventions. Exemplary humanized CCR4 antibodies are described in for example in WO 2009/086514, WO 2013/166500 and PCT/US2015/054202, the contents of which are incorporated by reference in their entireties and are described below. A preferred CCR4 antibody is mAb2-3. The Exemplary antibodies described herein have advantageous features compared to other humanized CCR4 antibodies, such as Mogamulizumab. For example, the exemplary antibodies of the invention, in particular mAb2-3 recognize a conformational epitope that encompasses the N-terminal domain and the extracellular loop that mediates biological signaling. In this regard, mAb2-3 treatment of Mac 1 cell and Tregs led to enhanced sCD25 shedding, a property that is shared with the CCR4 ligands CCL22 and CCL17. Thus the exemplary antibodies of the invention, in particular MAb2-3 have agonist activity and triggers cell activation. Additionally, in contrast to Mogamulizumab, the exemplary antibodies of the invention, in particular mAb2-3 mediates complement-dependent cytotoxicity (CDC). This may be the direct result of an optimal orientation of the Fc region, allowing the angle of attachment to be permissive for complement pore formation.

TABLE 1A mAb2-3 Variable Region nucleic acid sequences $V_H$ chain of mAb2-3 (SEQ ID NO: 1)
CAGGTGCAGCTGGTGCAGAGCGGCGCGGAAGTGAAAAAACCGGGCGCGAG
CGTGAAAGTGAGCTGCAAAGCGAGCGGCTATACCTTTGCGAGCGCGTGGA
TGCATTGGATGCGCCAGGCGCCGGGCCAGGGCCTGGAATGGATTGGCTGG
ATTAACCCGGGCAACGTGAACACCAAATATAACGAAAAATTTAAAGGCCG
CGCGACCCTGACCGTGGATACCAGCACCAACACCGCGTATATGGAACTGA
GCAGCCTGCGCAGCGAAGATACCGCGGTGTATTATTGCGCGCGCAGCACC
TATTATCGCCCGCTGGATTATTGGGGCCAGGGCACCCTGGTGACCGTGAG
CAGC $V_L$ chain of mAb2-3 IgG4 (SEQ ID NO: 3)
GATATTGTGATGACCCAGAGCCCGGATAGCCTGGCGGTGAGCCTGGGCGA
ACGCGCGACCATTAACTGCAAAAGCAGCCAGAGCATTCTGTATAGCAGCA
ACCAGAAAAACTATCTGGCGTGGTATCAGCAGAAACCGGGCCAGAGCCCG
AAACTGCTGATTTATTGGGCGAGCACCCGCGAAAGCGGCGTGCCGGATCG
CTTTAGCGGCAGCGGCAGCGGCACCGATTTTACCCTGACCATTAGCAGCC
TGCAGGCGGAAGATGTGGCGGTGTATTATTGCCATCAGTATATGAGCAGC
TATACCTTTGGCCAGGGCACCAAACTGGAAATTAAA

TABLE 1B mAb2-3 IgG4 Variable Region amino acid sequences $V_H$ chain of mAb2-3 IgG4 (SEQ ID NO: 2)
QVQLVQSGAEVKKPGASVKVSCKASGYTFASAWMHWMRQAPGQGLEWIGW
INPGNVNTKYNEKFKGRATLTVDTSTNTAYMELSSLRSEDTAVYYCARST
YYRPLDYWGQGTLVTVSS $V_L$ chain of mAb2-3 IgG4 (SEQ ID NO: 4)
DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYMSS
YTFGQGTKLEIK

TABLE 2A

Antibody 1-44 Variable Region nucleic acid sequences $V_H$ chain of 1-44 (SEQ ID NO: 15)
CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCCAATGGA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGAAGCACC
TGGTACCGGCCGCTGGACTACTGGGGCCAGGGCACCCTGGTGACCGTGAG
CAGC $V_L$ chain of 1-44 (SEQ ID NO: 17)
GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC

TABLE 2A-continued

Antibody 1-44 Variable Region nucleic acid sequences

AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACATCAGCAGC
TACACCTTCGGCCAGGGCACAAAGCTGGAAATCAAG

TABLE 2B

Antibody 1-44 Variable Region amino acid sequences $V_H$ chain of 1-44 (SEQ ID NO: 16)
QVQLVQSGAEVKKPGASVKVSCKASGYTFASQWMHWMRQAPGQGLEWIGW
INPGNVNTKYNEKFKGRATLTVDTSTNTAYMELSSLRSEDTAVYYCARST
WYRPLDYWGQGTLVTVSS $V_L$ chain of 1-44 (SEQ ID NO: 18)
DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYISS
YTFGQGTKLEIK

TABLE 3A

Antibody 1-49 Variable Region nucleic acid sequences $V_H$ chain of 1-49 (SEQ ID NO: 19)
CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCAGCTGGA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGGAGCGAGGACACCGCCGTGTACTACTGCGCCAGAAGCACG
TGGTATCGGCCGAATGACTACTGGGGCCAGGGCACCCTGGTGACCGTGAG
CAGC $V_L$ chain of 1-49 (SEQ ID NO: 21)
GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACAAAAGCAGC
TACACCTTCGGCCAGGGCACAAAGCTGGAAATCAAG

TABLE 3B

Antibody 1-49 Variable Region amino acid sequences $V_H$ chain of 1-49 (SEQ ID NO: 20)
QVQLVQSGAEVKKPGASVKVSCKASGYTFASSWMHWMRQAPGQGLEWIGW
INPGNVNTKYNEKFKGRATLTVDTSTNTAYMELSSLRSEDTAVYYCARST
WYRPNDYWGQGTLVTVSS $V_L$ chain of 1-49 (SEQ ID NO: 22)
DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYKSS
YTFGQGTKLEIK

TABLE 4A

Antibody 2-1 Variable Region nucleic acid sequences $V_H$ chain of 2-1 (SEQ ID NO: 23)
CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCAGCTGGA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGAACCACC
CGTTATCGGCCCCTGGACTACTGGGGCCAGGGCACCCTGGTGACCGTGAG
CAGC

TABLE 4A-continued

Antibody 2-1 Variable Region nucleic acid sequences $V_L$ chain of 2-1 (SEQ ID NO: 25)
GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACCGTAGCAGC
TACACCTTCGGCCAGGGCACAAAGCTGGAAATCAAG

TABLE 4B

Antibody 2-1 Variable Region amino acid sequences $V_H$ chain of 2-1 (SEQ ID NO: 24)
QVQLVQSGAEVKKPGASVKVSCKASGYTFASSWMHWMRQAPGQGLEWIGW
INPGNVNTKYNEKFKGRATLTVDTSTNTAYMELSSLRSEDTAVYYCARTT
RYRPLDYWGQGTLVTVSS $V_L$ chain of 2-1 (SEQ ID NO: 26)
DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYRSS
YTFGQGTKLEIK

TABLE 5A

Antibody 2-2 Variable Region nucleic acid sequences $V_H$ chain of 2-2 (SEQ ID NO: 27)
CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCCAATATA
TGCACTGGATGCGGCAGGCACCTGGACAGGGCCTCGAATGGATCGGCTGG
ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGGAGCGAGGACACCGCCGTGTACTACTGCGCCAGACTGACC
TATTATCGGCCGCCGGACTACTGGGGCCAGGGCACC
CTGGTGACCGTGAGCAGC $V_L$ chain of 2-2 (SEQ ID NO: 29)
GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCG
GTTTAGCGGCAGCGGCTCCGGCACCGACTTCACCCTGACCATCAGCAGCC
TGCAGGCCGAGGACGTGGCCGTGTACTACTGCCACCAGTACTATAGCAGC
TACACCTTCGGCCAGGGCACAAAGCTGGAAATCAAG

TABLE 5B

Antibody 2-2 Variable Region amino acid sequences $V_H$ chain of 2-2 (SEQ ID NO: 28)
QVQLVQSGAEVKKPGASVKVSCKASGYTFASQYMHWMRQAPGQGLEWIGW
INPGNVNTKYNEKFKGRATLTVDTSTNTAYMELSSLRSEDTAVYYCARLT
YYRPPDYWGQGTLVTVSS $V_L$ chain of 2-2 (SEQ ID NO: 30)
DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYYSS
YTFGQGTKLEIK

TABLE 6A huCCR4 Variable Region nucleic acid sequences $V_H$ chain of huCCR (SEQ ID NO: 43)
CAGGTGCAGCTGGTGCAGAGCGGAGCCGAGGTGAAGAAGCCTGGAGCTTC
CGTCAAGGTGTCCTGCAAGGCCAGCGGCTACACCTTCGCCAGCTACTACA
TGCACTGGATGCGGCAGGCACCTGGACAGGGCCTCGAATGGATCGGCTGG

TABLE 6A-continued huCCR4 Variable Region nucleic acid sequences

ATCAACCCCGGCAACGTGAACACCAAGTACAACGAGAAGTTCAAGGGCAG
GGCCACCCTGACCGTGGACACCAGCACCAACACCGCCTACATGGAACTGA
GCAGCCTGCGGAGCGAGGACACCGCCGTGTACTACTGCGCCAGAAGCACC
TACTACCGGCCCCTGGACTACTGGGGCCAGGGCACCCTGGTGACCGTGAG
CAGC

V_L chain of huCCR (SEQ ID NO: 45)
GACATCGTGATGACCCAGAGCCCCGACAGCCTGGCCGTGAGCCTGGGCGA
GCGGGCCACCATCAACTGCAAGAGCAGCCAGAGCATCCTGTACAGCAGCA
ACCAGAAGAACTACCTGGCCTGGTATCAGCAGAAGCCCGGCCAGAGCCCC
AAGCTGCTGATCTACTGGGCCAGCACCCGGGAGAGCGGCGTGCCCGACCC
GTTTAGCGGCAGCGGCTCCGGCACCGACTTCACCCTGACCATCAGCAGCC
TGCAGGCCGAGGACGTGGCCGTGTACTACTGCCACCAGTACCTGAGCAGC
TACACCTTCGGCCAGGGCACAAAGCTGGAAATCAAG

TABLE 6B huCCR4 Variable Region, amino acid sequences

V_H chain of huCCR (SEQ ID NO: 44)
QVQLVQSGAEVKKPGASVKVSCKASGYTFASYYMHWMRQAPGQGLEWIGW
INPGNVNTKYNEKFKGRATLTVDTSTNTAYMELSSLRSEDTAVYYCARST
YYRPLDYWGQGTLVTVSS V_L chain of huCCR (SEQ ID NO: 46)
DIVMTQSPDSLAVSLGERATINCKSSQSILYSSNQKNYLAWYQQKPGQSP
KLLIYWASTRESGVPDRFSGSGSGTDFTLTISSLQAEDVAVYYCHQYLSS
YTFGQGTKLEIK

TABLE 7A

IgG4 Isotype Region nucleic acid sequences

IgG4 Isotype Region nucleic acids (SEQ ID NO: 5)
GCGAGCACCAAAGGCCCGAGCGTGTTTCCGCTGGCGCCGTGCAGCCGCAG
CACCAGCGAAAGCACCGCGGCGCTGGGCTGCCTGGTGAAAGATTATTTTC
CGGAACCGGTGACCGTGAGCTGGAACAGCGGCGCGCTGACCAGCGGCGTG
CATACCTTTCCGGCGGTGCTGCAGAGCAGCGGCCTGTATAGCCTGAGCAG
CGTGGTGACCGTGCCGAGCAGCAGCCTGGGCACCAAAACCTATACCTGCA
ACGTGGATCATAAACCGAGCAACACCAAAGTGGATAAACGCGTGGAAAGC
AAATATGGCCCGCCGTGCCCGAGCTGCCCGGCGCCGGAATTTCTGGGCGG
CCCGAGCGTGTTTCTGTTTCCGCCGAAACCGAAAGATACCCTGATGATTA
GCCGCACCCCGGAAGTGACCTGCGTGGTGGTGGATGTGAGCCAGGAAGAT
CCGGAAGTGCAGTTTAACTGGTATGTGGATGGCGTGGAAGTGCATAACGC
GAAAACCAAACCGCGCGAAGAACAGTTTAACAGCACCTATCGCGTGGTGA
GCGTGCTGACCGTGCTGCATCAGGATTGGCTGAACGGCAAAGAATATAAA
TGCAAAGTGAGCAACAAAGGCCTGCCGAGCAGCATTGAAAAAACCATTAG
CAAAGCGAAAGGCCAGCCGCGCGAACCGCAGGTGTATACCCTGCCGCCGA
GCCCGGAAGAAATGACCAAAAACCAGGTGAGCCTGACCTGCCTGGTGAAA
GGCTTTTATCCGAGCGATATTGCGGTGGAATGGGAAAGCAACGGCCAGCC
GGAAAACAACTATAAAACCACCCCGCCGGTGCTGGATAGCGATGGCAGCT
TTTTTCTGTATAGCCGCCTGACCGTGGATAAAAGCCGCTGGCAGGAAGGC
AACGTGTTTAGCTGCAGCGTGATGCATGAAGCGCTGCATAACCATTATAC
CCAGAAAAGCCTGAGCCTGAGCCTGGGCAAA

TABLE 7B

IgG4 Isotype Region amino acid sequences

IgG4 Isotype Region amino acid sequences
(SEQ ID NO: 6)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSPEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK

TABLE 8A

IgG4 with stabilized IgG4 core hinge, nucleic acid sequences

IgG4 Isotype Region nucleic acids (SEQ ID NO: 7)
ACCAAAGGCCCGAGCGTGTTTCCGCTGGCGCCGTGCAGCCGCAGCACCAG
CGAAAGCACCGCGGCGCTGGGCTGCCTGGTGAAAGATTATTTTCCGGAAC
CGGTGACCGTGAGCTGGAACAGCGGCGCGCTGACCAGCGGCGTGCATACC
TTTCCGGCGGTGCTGCAGAGCAGCGGCCTGTATAGCCTGAGCAGCGTGGT
GACCGTGCCGAGCAGCAGCCTGGGCACCAAAACCTATACCTGCAACGTGG
ATCATAAACCGAGCAACACCAAAGTGGATAAACGCGTGGAAAGCAAATAT
GGCCCGCCGTGCCCGCCGTGCCCGGCGCCGGAATTTCTGGGCGGCCCGAG
CGTGTTTCTGTTTCCGCCGAAACCGAAAGATACCCTGATGATTAGCCGCA
CCCCGGAAGTGACCTGCGTGGTGGTGGATGTGAGCCAGGAAGATCCGGAA
GTGCAGTTTAACTGGTATGTGGATGGCGTGGAAGTGCATAACGCGAAAAC
CAAACCGCGCGAAGAACAGTTTAACAGCACCTATCGCGTGGTGAGCGTGC
TGACCGTGCTGCATCAGGATTGGCTGAACGGCAAAGAATATAAATGCAAA
GTGAGCAACAAAGGCCTGCCGAGCAGCATTGAAAAAACCATTAGCAAAGC
GAAAGGCCAGCCGCGCGAACCGCAGGTGTATACCCTGCCGCCGAGCCCGG
AAGAAATGACCAAAAACCAGGTGAGCCTGACCTGCCTGGTGAAAGGCTTT
TATCCGAGCGATATTGCGGTGGAATGGGAAAGCAACGGCCAGCCGGAAAA
CAACTATAAAACCACCCCGCCGGTGCTGGATAGCGATGGCAGCTTTTTTC
TGTATAGCAAACTGACCGTGGATAAAAGCCGCTGGCAGGAAGGCAACGTG
TTTAGCTGCAGCGTGATGCATGAAGCGCTGCATAACCATTATACCCAGAA
AAGCCTGAGCCTGAGCCTGGGCAAA

TABLE 8B

IgG4 with stabilized IgG4 core hinge, amino acid sequences

IgG4 Isotype Region amino acid sequences
(SEQ ID NO: 8)
TKGPSVFPLAPCSRSTSESTAALGCLVKDYFPEPVTVSWNSGALTSGVHT
FPAVLQSSGLYSLSSVVTVPSSSLGTKTYTCNVDHKPSNTKVDKRVESKY
GPPCPPCPAPEFLGGPSVFLFPPKPKDTLMISRTPEVTCVVVDVSQEDPE
VQFNWYVDGVEVHNAKTKPREEQFNSTYRVVSVLTVLHQDWLNGKEYKCK
VSNKGLPSSIEKTISKAKGQPREPQVYTLPPSPEEMTKNQVSLTCLVKGF
YPSDIAVEWESNGQPENNYKTTPPVLDSDGSFFLYSKLTVDKSRWQEGNV
FSCSVMHEALHNHYTQKSLSLSLGK The amino acid sequences of the heavy and light chain complementarity determining regions of selected antibodies are shown in Table 9 below.

TABLE 9

Amino Acid Sequences of Heavy and Light Chains.

| Antibody | Variable region | CDR1 | CDR2 | CDR3 |
|---|---|---|---|---|
| Mouse 1567 | VH | GYTFASYY (SEQ ID NO: 31) | INPGNVNT (SEQ ID NO: 11) | STYYRPLDY (SEQ ID NO: 13) |
| Humanized 1567 | VH | GYTFASYY (SEQ ID NO: 31) | INPGNVNT (SEQ ID NO: 11) | STYYRPLDY (SEQ ID NO: 13) |

TABLE 9-continued

Amino Acid Sequences of Heavy and Light Chains.

| Antibody | Variable region | CDR1 | CDR2 | CDR3 |
|---|---|---|---|---|
| Ab1-44 | VH | GYTFASQW (SEQ ID NO: 32) | INPGNVNT (SEQ ID NO: 11) | STWYRPLDY (SEQ ID NO: 34) |
| Ab1-49 | VH | GYTFASSW (SEQ ID NO: 33) | INPGNVNT (SEQ ID NO: 11) | STWYRPNDY (SEQ ID NO: 35) |
| Ab2-1 | VH | GYTFASSW (SEQ ID NO: 33) | INPGNVNT (SEQ ID NO: 11) | TTRYRPLDY (SEQ ID NO: 36) |
| Ab2-2 | VH | GYTFASQY (SEQ ID NO: 33) | INPGNVNT (SEQ ID NO: 11) | LTYYRPPDY (SEQ ID NO: 37) |
| Ab2-3 | VH | GYTFASAW (SEQ ID NO: 9) | INPGNVNT (SEQ ID NO: 11) | STYYRPLDY (SEQ ID NO: 13) |
| Mouse 1567 | VL | QSILYSSNQKNY (SEQ ID NO: 10) | WASTRE (SEQ ID NO: 12) | HQYLSSYT (SEQ ID NO: 38) |
| Humanized 1567 | VL | QSILYSSNQKNY (SEQ ID NO: 10) | WASTRE (SEQ ID NO: 12) | HQYLSSYT (SEQ ID NO: 38) |
| Ab1-44 | VL | QSILYSSNQKNY (SEQ ID NO: 10) | WASTRE (SEQ ID NO: 12) | HQYISSYT (SEQ ID NO: 39) |
| Ab1-49 | VL | QSILYSSNQKNY (SEQ ID NO: 10) | WASTRE (SEQ ID NO: 12) | HQYKSSYT (SEQ ID NO: 40) |
| Ab2-1 | VL | QSILYSSNQKNY (SEQ ID NO: 10) | WASTRE (SEQ ID NO: 12) | HQYRSSYT (SEQ ID NO: 41) |
| Ab2-2 | VL | QSILYSSNQKNY (SEQ ID NO: 10) | WASTRE (SEQ ID NO: 12) | HQYYSSYT (SEQ ID NO: 42) |
| Ab2-3 | VL | QSILYSSNQKNY (SEQ ID NO: 10) | WASTRE (SEQ ID NO: 12) | HQYMSSYT (SEQ ID NO: 14) |

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$, and $F_{(ab')2}$ fragments, scFvs, and $F_{ab}$ expression libraries.

A single chain Fv ("scFv") polypeptide molecule is a covalently linked $V_H$:$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, $IgG_3$, $IgG_4$ and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CCR4 epitope when the equilibrium binding constant ($K_d$) is preferably ≤100 nM, more preferably ≤10 nM, and most preferably ≤100 pM to about ≤1 pM, as measured by assays such as radioligand binding assays or similar assays known to those skilled in the art.

A CCR4 protein, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to CCR4. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the CCR4 protein, with which it is normally reactive, and then add the human monoclonal antibody being tested to determine if the human monoclonal antibody being tested is inhibited in its ability to bind CCR4. If the human monoclonal antibody being tested is inhibited then, in all likelihood, it has the same, or functionally equivalent, epitope specificity as the monoclonal antibody of the invention. Screening of human monoclonal antibodies of the invention, can be also carried out by utilizing CCR4 and determining whether the test monoclonal antibody is able to neutralize CCR4.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "mAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771.

This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of CCR4 in a sample. The antibody can also be used to try to bind to and disrupt a CCR4 activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may also refer to bi-specific antibodies, wherein a bi-specific antibody is composed of, for example, two covalently joined single chain antibodies, or scFvs, or two covalently joined variable heavy chain-variable light chain dimers from two antibodies that recognize different antigens.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radio conjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, mutations are introduced to the constant regions of the mAb such that the antibody dependent cell-mediated cytotoxicity (ADCC) activity of the mAb is altered. For example, the mutation is an LALA mutation in the CH2 domain, wherein the leucines at positions 234 and 235 of the Fc region is mutated to alanine, and abrogates binding by specific Fc receptors. In one aspect, the mAb contains mutations on one scFv molecule of the heterodimeric mAb, which reduces the ADCC activity. In another aspect, the mAb contains mutations on both chains of the heterodimeric mAb, which completely ablates the ADCC activity. For example, the mutations introduced one or both scFv molecules of the mAb are LALA mutations in the CH2 domain. These mAbs with variable ADCC activity can be optimized such that the mAbs exhibits maximal selective killing towards cells that express one antigen that is recognized by the mAb, however exhibits minimal killing towards the second antigen that is recognized by the mAb.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Pharmaceutical Compositions

The CCR4 antibodies (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Bi-Specific Antibodies

A bi-specific antibody (bsAb) is an antibody comprising two variable domains or scFv units such that the resulting antibody recognizes two different antigens. The present invention provides for bi-specific antibodies that recognize CCR4 and a second antigen. Exemplary second antigens include tumor associated antigens, cytokines and cell surface receptors such as a T-cell receptor polypeptide. In some embodiments, the second antigen can be CAIX (carbonic anhydrase IX, or G250), ErbB2, PD-L1, CTLA-4, PD1, IL21, IL21R, HVEM, CD160, CD3, TIM3 or GAL9.

A bi-specific antibody of the present invention comprises a heavy chain and a light chain combination or scFv of the CCR4 antibody.

Bi-specific antibodies of the present invention can be constructed using methods known art. In some embodiments, the bi-specific antibody is a single polypeptide wherein two different heavy-light chain heterodimers or two different scFv antibodies, or fragments thereof, that each recognize a different antigen are joined by a long linker polypeptide, of sufficient length to allow intramolecular association between the two scFv molecules to form a bi-specific antibody, with two heavy chains and two light chains. In one embodiment, one of the scFv molecules recognizes CCR4, for example, any of the scFv antibodies described herein. In other embodiments, the bi-specific antibody consists of more than one polypeptide, for example, two separate scFv antibodies, or fragments thereof, linked by covalent or non-covalent bonds, wherein one of the scFv antibodies recognizes CCR4.

In one embodiment, the bi-specific antibody is constructed using the "knob into hole" method (Ridgway et al., Protein Eng 7:617-621 (1996)). In this method, the Ig heavy chains of the two different variable domains are reduced to selectively break the heavy chain pairing while retaining the heavy-light chain pairing. The two heavy-light chain heterodimers that recognize two different antigens are mixed to promote heteroligation pairing, which is mediated through the engineered "knob into holes" of the CH3 domains.

In another embodiment, the bi-specific antibody can be constructed through exchange of heavy-light chain heterodimers from two or more different antibodies to generate a hybrid antibody where the first heavy-light chain heterodimer recognizes CCR4 and the second heavy-light chain heterodimer recognizes a second antigen. The mechanism for generating a bi-specific antibody consisting of two heavy-light chain heterodimers from two different antibodies is similar to the formation of human IgG4, which also functions as a bispecific molecule. Dimerization of IgG heavy chains is driven by intramolecular force, such as the pairing the CH3 domain of each heavy chain and disulfide bridges. Presence of a specific amino acid in the CH3 domain (R409) has been shown to promote dimer exchange and construction of the IgG4 molecules. Heavy chain pairing is also stabilized further by interheavy chain disulfide bridges in the hinge region of the antibody. Specifically, in IgG4, the hinge region contains the amino acid sequence Cys-Pro-Ser-Cys (in comparison to the stable IgG1 hinge region which contains the sequence Cys-Pro-Pro-Cys) at amino acids 226-230. This sequence difference of Serine at position 229 has been linked to the tendency of IgG4 to form novel intrachain disulfides in the hinge region (Van der Neut Kolfschoten, M. et al., 2007, Science 317:1554-1557 and Labrijn, A. F. et al, 2011, *Journal of immunol* 187:3238-3246).

In another embodiment, the use of glutathione and glutathione disulfide can be used in the production of bi-specific antibodies from two distinct full antibodies. For example, the full antibodies, each which recognize different antigens, are incubated with reducing glutathione to separate the antibodies into heavy-light chain heterodimers, or molecules. The heavy-light chain heterodimers may be mixed with oxidized glutathione (GSSG) which allows reassembly and reoxidation to form highly pure bi-specific antibodies.

Therefore, bi-specific antibodies of the present invention can be created through introduction of the R409 residue in the CH3 domain and the Cys-Pro-Ser-Cys sequence in the hinge region of antibodies that recognize CCR4 or a second antigen, so that the heavy-light chain dimers exchange to produce an antibody molecule with one heavy-light chain dimer recognizing CCR4 and the second heavy-light chain dimer recognizing a second antigen, wherein the second antigen is any antigen disclosed herein. Heavy-light chain heterodimer exchange can also be enhanced with addition of a reducing agent, such as reduced glutathione, to promote the exchange. Known IgG4 molecules may also be altered such that the heavy and light chains recognize CCR4 or a second antigen, as disclosed herein. Use of this method for constructing the bi-specific antibodies of the present invention may be beneficial due to the intrinsic characteristic of IgG4 molecules wherein the Fc region differs from other IgG subtypes in that it interacts poorly with effector systems of the immune response, such as complement and Fc receptors expressed by certain white blood cells. This specific property makes these IgG4-based bi-specific antibodies attractive for therapeutic applications, in which the antibody is required to bind the target(s) and functionally alter the signaling pathways associated with the target(s), however not trigger effector activities.

In some embodiments, mutations are introduced to the constant regions of the bsAb such that the antibody dependent cell-mediated cytotoxicity (ADCC) activity of the bsAb is altered. For example, the mutation is an LALA mutation in the CH2 domain, wherein the leucines at positions 234 and 235 of the Fc region is mutated to alanine, and abrogates binding by specific Fc receptors. In one aspect, the bsAb contains mutations on one scFv molecule of the heterodimeric bsAb, which reduces the ADCC activity. In another aspect, the bsAb contains mutations on both chains of the heterodimeric bsAb, which completely ablates the ADCC activity. For example, the mutations introduced one or both scFv molecules of the bsAb are LALA mutations in the CH2 domain. These bsAbs with variable ADCC activity can be optimized such that the bsAbs exhibits maximal selective killing towards cells that express one antigen that is recognized by the bsAb, however exhibits minimal killing towards the second antigen that is recognized by the bsAb.

The present invention provides for bi-specific antibodies that recognize CCR and a second antigen. In one embodiment, the second antigen is PD-L1. In another embodiment, the second antigen is CAIX. In other embodiments the second antigen is CA-IX, ErbB2, PD-L1, PD-1, CD3, IL21, IL21R, HVEM, CD160, TIM3, GITR, LAG3 or GAL9.

The bi-specific antibodies disclosed herein may be useful in treatment of diseases or medical conditions, for example, cancer. The cancer is, for example, a solid cancer, such as renal cell carcinoma, breast cancer or prostate cancer. In other embodiments, the cancer is a cancer in which CAIX, PD-L1 or HVEM is overexpressed when compared to tissue or a subject that does not have cancer. The bi-specific antibodies of the present invention may be used to treat, prevent, or alleviate a symptom of the cancer.

The bi-specific antibodies of the present invention may be used to increase T cell proliferation, in which the T cell is a regulatory T cell. The bi-specific antibodies of the present invention may be particularly useful for promoting or augmenting a T cell response, such as an antigen-specific T cell response. The bi-specific antibodies of the present invention can also be useful for reversing regulatory T cell-mediated suppression of effector T cell proliferation.

Fusion Proteins

In some embodiments, the CCR4 antibody, or functional fragment thereof, is joined directly to the second protein. In other embodiments, the CCR4 antibody, or functional fragment thereof, is joined to the second protein via a linker, such as a flexible polypeptide chain. The linker can be any suitable linker of any length, but can be at least 1, 2, 3, 4, 5, 10, 15, 20, 25, or 30 amino acids in length. In one embodiment, the linker is an amino acid sequence that is naturally present in immunoglobulin molecules of the host, such that the presence of the linker would not result in an immune response against the linker sequence by the mammal. Fusion proteins of the present invention that include more than one additional protein to the CCR4 antibody may have multiple linker sequences that join each additional protein or peptide sequence.

The fusion proteins of the present invention may be constructed by recombinant methods known to the skilled artisan. For example, an expression vector containing the nucleic acid sequence encoding a CCR4 antibody of the present invention can be operably linked to the nucleic acid sequence encoding the second protein and can be introduced to an expression system to translate and produce the fusion protein. Alternatively, one skilled in the art could readily utilize de novo protein synthesis techniques to produce the fusion proteins described herein.

Combinatory Methods

The invention provides method of administering two antibodies that bind to the same epitope of the CCR4 protein or, alternatively, two different epitopes of the CCR4 protein. Also, the cancer is treated by administering a first antibody that binds to CCR4 and a second antibody that binds to a protein other than CCR4.

Additionally, the invention provides administration of an antibody that binds to the CCR4 protein and an antineoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

It should be understood that the present invention is not limited to the particular methodologies, protocols and reagents, and examples described herein. The terminology and examples used herein is for the purpose of describing particular embodiments only, for the intent and purpose of providing guidance to the skilled artisan, and is not intended to limit the scope of the present invention.

EXAMPLES

Example 1 General Methods

Determining Molecular Densities on the Surfaces of T Cells

T cells were incubated with PacBlue-anti-CD3, BV570-anti-CD4, APC-anti-CD25, PE-Cy7-anti-CD127, PE-Cy5-anti-CD45RA, PerCP-Cy5.5-CCR7 and PE-anti-CCR4 mAbs at the concentration recommended in the datasheet. Cells were stained in 100 µl of FACS buffer (PBS supplemented with 5 mM EDTA and 1% BSA) at 4° C. for 30 min. T cells were gated into different T cell subsets according to the CD markers and analyzed for PE fluorescent intensity. The fluorescent intensities were compared to standard calibration BD QuantiBRITE PE Beads (BD Biosciences, San Jose, Calif.) to determine the total number of molecules per cell/bead, which were divided by the cell/bead surface area to obtain site densities.

Treg Suppression Assay $CD4^+$ $CD25^-$ T cells were labeled with CFSE (BioLegend, San Diego, Calif.) at the concentration of 5 µM and cultured in 96-well plates at $5 \times 10^4$ cells/well in the presence and absence of 20 µg/ml phytohaemagglutinin (PHA, Sigma, St. Louis, Mo.) as positive and negative control for T cell proliferation, respectively. $CD4^+$ and $CD4^+CCR4^-$ Tregs were isolated using Treg Enrichment Kit (StemCell, Vancouver, Canada) and mAb2-3-conjugated Dynabeads M-280 (Life Technologies, Carlsbad, Calif.). $5 \times 10^3$ $CD4^+$ and $CD4^+CCR4^-$ Tregs were individually incubated with CFSE-labeled $CD4^+$ $CD25^-$ T cells at 37° C. for 7 days. To measure the proliferation of CFSE-labeled T cells, co-cultured cells were stained with Viability Dye eFluor 506 (eBioscience, San Diego, Calif.) and then the live $CFSE^+$ cells were gated and analyzed using flow cytometry.

For survival assay, $CD4+CD127^{dim/-}$ $CD49d$ Tregs were isolated from PBMCs using Treg Cell Enrichment Kit. $1 \times 10^5$ Tregs were cultured with 0.5 IU/ml IL-2, 20 µg/ml mAb2-3 IgG1, and 20 µg/ml control IgG1 separately or in combinations, and incubated at 37° C. for five days. Cells were then stained with Viability Dye (eBioscience) and analyzed using flow cytometry.

Cells

OvCA cell lines, IGROV-1, OVCAR-5, and OVCAR-8, were incubated at 37° C. in a 5% $CO_2$-containing atmosphere. OVCAR-5 and OVCAR-8 were cultured in RPMI-1640 (Life Technologies) supplemented with 10% fetal bovine serum (FBS) and 1% penicillin/streptomycin (Life Technologies). IGROV-1 was cultured in 10% FBS and 1% penicillin/streptomycin Dulbecco's modification of Eagle medium (DMEM, Life Technologies). Luciferase-expressed IGROV-1 and T cells were stably transduced with a luciferase reporter retrovirus and authenticated by detecting luminescence. No additional authentication of these cell lines was conducted by the authors.

Animals 6-8 weeks-old female NOD.Cg-Prkdc$^{scid}$ Il2rg$^{tm1Wjl}$/SzJ (NSG) mice (The Jackson Laboratory, Bar Harbor, Me.) were used in this study. $2 \times 10^6$ or $5 \times 10^6$ luciferase-expressing IGROV-1 cells were injected into the dorsolateral flank subcutaneously (s.c.) in NSG mice and incubated for one or three days, respectively. Then, mice were randomly assigned into different groups and treated with IGROV-1-primed T cells ($4\times10^6$ or $1\times10^7$) and 3 mg/kg mAb2-3 IgG1, mAb2-3 IgG4 and control mAb (twice a week for 5 weeks) by i.v. injection. Body weight and tumor size were measured using digital calipers and Xenogen imaging. Tumor volumes were calculated as length×(width)$^2$×0.52. Animal care was carried out in accordance with the guidelines of Animal Care and Use Committee of Dana-Farber Cancer Institute (Boston, Mass.).

Chemotaxis

T cells ($1\times10^6$ cells/well) were placed in transwell migration wells (Corning, Tewksbury, Mass.) with or without mAb2-3 for 5 hours at 37° C. Migrated cells were harvested from the bottom chamber containing OvCA cell-cultured medium or 100 ng/mL human CCL22 (R&D Systems) and enumerated by FACS analysis. The OvCA cell-cultured medium was harvested from the supernatant of IGROV-1-, OVCAR-5-, and OVCAR-8-cultured medium ($1\times10^6$ cells/ml). T cell migration was calculated as a percentage relative to culture or CCL22-supplemented medium.

Establishment of Tumor-Primed T (TP-T) Cells

PBMCs ($2\times10^6$/ml) were incubated with autologous IGROV-1-pulsed dendritic cells (DCs, $2\times10^5$/ml) in complete medium containing recombinant IL-2 (30 IU/ml) and IL-7 (5 ng/ml). Cells were incubated in 50-ml tissue culture flasks at 37° C. in 5% $CO_2$ incubator. PBMCs were re-stimulated with lysate-pulsed autologous DCs every 2 weeks, and the cultures were fed every 5 days with fresh medium containing recombinant IL-2 and IL-7. After 3 to 4 cycles of antigen stimulation and selection, TP-T cells were established, and cells were expanded in complete medium containing recombinant IL-2 and IL-7 for 2 weeks and were subjected to functional tests.

Analysis of Cytokine Production

TP-T cells ($1\times10^5$) were incubated with autologous IGROV-1-pulsed DCs ($2\times10^4$), unpulsed DCs ($2\times10^4$), or Dynabeads Human T-Activator CD3/CD28 (Life Technologies) in the complete medium at 37° C. After 48-hour incubation, the supernatant was harvested and IFN-γ was detected using Human IFN-γ Reagent Kit (Pierce Biotechnology, Rockford, Ill.) and Meso Scale Discovery Sector Imager 2400 (MSD, Rockville, Md.). In addition, TP-T cells were incubated with mAb2-3-conjugated beads to deplete CCR4$^+$ TP-T cells. TP-T or CCR4$^-$ TP-T cells ($1\times10^5$) were incubated with IGROV-1 ($1\times10^4$) in the presence or absence of 20 µg/ml of mAb2-3 IgG1 or IgG4 in complete medium. After 24 and 48 hours incubation, IFN-γ production by TP-T cells was assessed by MSD and intracellular FACS analysis.

Supernatant Cytokines, IL-2, and sCD25 Detection

Cytokines and soluble CD25 were detected in cell culture supernatants using ELISA Ready-SET-Go! Kits for IL-2, IL-10, and TGF-β (eBioscience) and Human IL-2 sRα ELISA Set (BD Biosciences) according to manufacturer instructions. Samples were diluted (when necessary) in RPMI-1640 medium. For IL-10 and TGF-β, autologous CD4$^+$ CD25$^-$ and CD4$^+$ CD25$^+$ T cells (1:1) were cultured with 10% FBS RPMI-1640 medium in anti-CD3/28 (1/0.5 µg/ml) coated plates in the presence or absence of 20 µg/ml antibodies. For IL-2, Teffs and Tregs alone or co-culture were incubated with 10% FBS RPMI-1640 medium in the presence or absence of exogenous IL-2 or antibodies. In the presence of exogenous IL-2 (20 IU/ml), $2\times10^5$ Mac-1 cells were cultured with or without antibodies (mAb2-3 or anti-CD25, including anti-TAC and control mAbs). For competition assay, Mac-1 cells were stained with biotinylated IL-2 in the presence or absence of different concentration of antibodies and then detected by FACS. For sCD25 study, Mac-1 cells were incubated with mAb2-3, CCL17, or CCL22 in the presence and absence of MMP-9 inhibitor (CAS 1177749-58-4) or GM6001, negative control from Calbiochem (EMD Biosciences, San Diego, Calif.). Cells were incubated for 12, 24, and 48 hours and then cultured supernatant were harvested for ELISA.

Statistical Analyses

Data were analyzed using two-sided unpaired Student t-test and two-way ANOVA for in vitro and in vivo experiments, respectively. *, , and * indicate P value<0.05, 0.01, and 0.005, respectively.

Example 2: CCR4 Expression Profiles on Human T Cell Populations

Human peripheral blood mononuclear cells (hPBMCs) were isolated from healthy donors and stained with multiple T cell surface markers to delineate the T cell subpopulations (FIG. 1A). Cell markers (CD3, CD4, CD25, and CD127) were used to identify CD4$^+$ CD25$^{high}$CD127$^{dim/-}$ Tregs and CD4$^+$ CD25$^-$ CD127$^+$ Teffs. In addition, anti-CCR7 and anti-CD45RA antibodies were used to assign Teffs into four subsets, i.e. naïve (Tnaïve), central memory (Tcm), effector memory (Tem), and other Teff populations (oTeffs). The percentage of each CD4$^+$ T cell subset from hPBMCs was measured (FIG. 1B). The CCR4 expression profiles of CD4$^+$ T cell subsets were further screened and quantified by QuantiBRITE PE beads and PE-labeled anti-CCR4 antibody using flow cytometry (FIGS. 1C, 7A, and S1B). The CCR4 molecules were uniformly expressed on Tregs (FIG. 1D) with a surface density (19,717±1416, n=3) that was circa 2.5-fold higher than on Teffs (8063±165, n=3) (FIG. 1E). Although CCR4 expression on Teffs was variable (4-40%) (FIG. 1D), similar numbers of CCR4 molecules were present on CCR4 positive cells (FIG. 7C).

Example 3: The Immunosuppression Ability of CCR4$^+$ Tregs on Teff Cell Proliferation To evaluate if the CCR4$^+$ Tregs mediate immunosuppression, CCR4 staining was performed together with CD25 and FoxP3 co-staining. In FIG. 2A, 85% of cells in the CD3$^+$, CD4$^+$, CD25$^+$, and FoxP3$^+$ T-cell gate were found to co-express CCR4. Treg suppression assay was then performed to determine the biological function of CCR4$^+$ Tregs. As shown in FIGS. 2B and 2C, Teff proliferation was suppressed in the co-cultures with total Tregs but not in the co-culture with CCR4$^-$ Tregs, suggesting that the CCR4$^+$ Treg subset plays an important role in suppressor activity.

Example 4: In Vivo Depletion of Tregs by mAB2-3 IgG1 in huPBL-NSG Mice

To investigate whether mAb2-3 treatment could modulate the Treg population in vivo, two isotypes of mAb2-3-IgG1 and IgG4 isotype were used, the latter has limited in vivo depletion activity due to its narrow range and low affinities for Fcγ receptors (FcγRs) (20). These antibodies were injected into human peripheral blood lymphocyte NSG mice (aka huPBL-NSG mice) and the Treg percentages in mouse blood were examined. As shown in FIG. 8A, at day 1 post treatment the CD4$^+$ CD25$^+$ CD127$^{dim/-}$ Treg population were markedly decreased in the mAb2-3 IgG1 group but as, expected, not in the mAb2-3 IgG4 or control mAb treated groups (FIGS. 8B and 8C). At Day 7, there was <50% recovery of Tregs in mAb2-3 treated mice compared to mAb2-3 IgG4 and control mAb treated groups. Long-term effects of mAb2-3 IgG4 multiple dose treatments in hu-PBL-NSG mice were also investigated. FIG. 9 shows that the percentage of $CD3^+$ $CD4^+$ $CD25^+$ $CD127^-$ cells in human $CD45^+$ lymphocytes in mouse blood, spleen, and bone marrow were not altered significantly over the three-week study. Interestingly, the total numbers of $CD3^+$ T cells and $CD8^+$ T cells increased in the mice treated with mAb2-3 IgG4 at the last time point (FIG. 9 C&E, respectively). These results indicate that mAb2-3 IgG1, not IgG4, leads to in vivo depletion of Tregs.

Example 5: Inhibition of OvCA-Mediated Treg Migration by mAB2-3 In Vitro and In Vivo The CCL22 expression levels in three OvCA cell lines IGROV-1, OVCAR-5 and OVCAR-8 were examined. In agreement with transcriptional profiling studies (data not shown), CCL22 expression was highest in IGROV-1, modest in OVCAR-5 and undetectable in OVCAR-8 cells (FIG. 3A). No CCR4 expression was detected on any of these cell lines (FIG. 10A). We further performed a chemotaxis assay using either culture supernatant from these cell lines or recombinant human CCL22. All three cultured mediums showed increased Treg migration compared to fresh medium. However, both mAb2-3 IgG1 and IgG4 were capable of inhibiting Treg chemotaxis induced by CCL22 containing IGROV-1 and OVCAR-5 supernatants but not by OVCAR-8 supernatants. (FIG. 3B). Treg chemotaxis to CCL22 was also inhibited by mAb2-3 in a dose-dependent manner (FIG. 10B). These results indicate that both mAb2-3 IgG1 and IgG4 were able to inhibit the recruitment of Tregs to CCL22-secreting OvCA cells in vitro.

To evaluate if mAb2-3 could block Treg recruitment in vivo, w luciferase-transduced $CD4^+$ or $CD4^+$ $CD25^+$ T cells were injected into mice bearing IGROV-1 xenograft tumors followed by treatment with mAb2-3 or control antibody. After 18 hours, bioluminescent imaging showed that the CCL22-secreting tumor recruited the $CD4^+$ and $CD4^+$ $CD25^+$ T cells in mice treated with control IgG1, but such recruitment was reduced by treatment with mAb2-3 IgG1 (FIGS. 3C and 3D, respectively). The recruitment $CD4^+$ $CD25^+$ $CD127^{dim/-}$ Tregs after 48 hours of mAb2-3 treatment was investigated and it was found that a) Tregs accumulated in tumor tissue in the control IgG1 group, b) Tregs were depleted by mAb2-3 IgG1 and c) Tregs were diffusely distributed in the mice treated with mAb2-3 IgG4 (FIG. 11A). Both mAb2-3 IgG1 and IgG4 treatment resulted in lower bioluminescent intensity in the tumor tissue (FIG. 11B) and lesser tumor-infiltrating Tregs (FIG. 11C) than control group. These results indicate that mAb2-3 IgG1 treatment resulted in Treg depletion while mAb2-3 IgG4 treatment lead to inhibition of tumor-infiltrating Treg recruitment in vivo.

Example 6: Enhanced Anti-Tumor Immunity Mediated by mAB2-3 In Vitro

Figure 12:
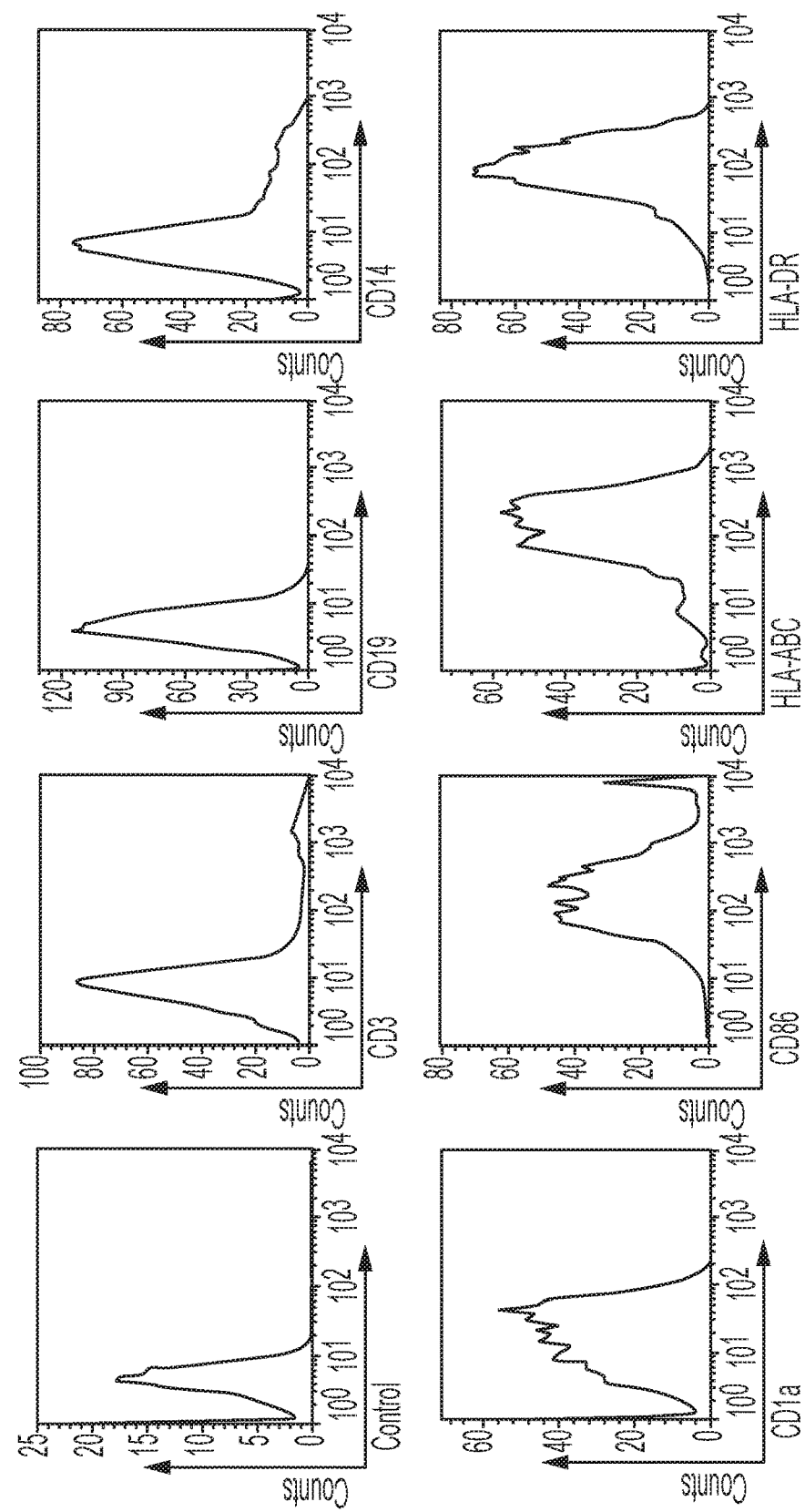
FIG. 12. Development of IGROV-1-pulsed dendritic cells and IGROV-1-primed T cells. (A) Monocytic differentiation into dendritic cells (DCs) by Granulocyte macrophage colony-stimulating factor (GM-CSF) and Interleukin-4 (IL-4) in combination. Monocytes were isolated from human PBMCs and cultured in the presence of GM-CSF (100 ng/ml) and IL-4 (100 ng/ml) combination. After culturing for 7 days, cells were harvested and analyzed by flow cytometry for surface expression of various markers for DC differentiation as indicated. (B) IFN-γ secretions were detected from the cocultured supernatant of tumor-primed T cells (TP-T cells), untreated DCs, and tumor-pulsed DCs. Bars represent ±S.D. "*" represent student's t-test p<0.05.

To establish an OvCA xenograft bearing humanized mouse model, IGROV-1-specific T cells in vitro were created that could be tested subsequently for in vivo immunotherapy. Dendritic cells (DCs) were differentiated from monocytes harvested from hPBMCs (FIG. 12A), pulsed with IGROV-1 cell lysates, and co-cultured with autologous hPBMCs to generate tumor-primed T (TP-T) cells. These TP-T cells were able to respond to tumor antigens, leading to production of IFN-γ in a co-culture with IGROV-1-pulsed DCs (FIG. 12B). Furthermore, as shown in the representative experiment in FIG. 4A, TP-T cells consisted of circa 31.6±1.4% (n=3) $CD25^+$ $CCR4^+$ T cells among all $CD4^+$ T cells. These $CCR4^+$ TP-T cells could also be removed using mAb2-3-conjugated magnetic beads (FIG. 4B). As shown in FIG. 4C, TP-T cells co-cultured with IGROV-1 cells exhibited an increased release of IFN-γ compared to TP-T cells cultured alone. Cell staining studies showed an increase in IFN-γ expression for both $CD8^+$ and $CD4^+$ TP-T cells reacting to IGROV-1 cells compared to unprimed T cells from the same donor (FIG. 4D).

Additionally, the co-culture showed enhanced IFN-γ activity when $CCR4^+$ cells were depleted with mAb2-3 from the TP-T population (FIG. 4C). However, there was no enhanced effect of soluble mAb2-3 IgG1 or IgG4 treatment compared to control IgG1. This lack of mAb2-3 enhancement suggested that Treg depletion may be required in this in vitro system to achieve reversal of TP-T suppression possible because of the high percentage of Tregs in the co-cultures, their release of suppressive mediators and/or requirement for cell-to-cell contact. Moreover, mAb2-3-depleted TP-T cells could induce higher cellular cytotoxicity on IGROV-1 cells than non-depleted TP-T cell (FIG. 4E). These data indicate that the TP-T cells, especially mAb2-3-depleted $CCR4^+$ TP-T cells, could induce anti-tumor responses and mediate tumor cell death.

Example 7: Evaluation of mAB2-3 Anti-Tumor Effect In Vivo

The functional and thus potential therapeutic relevance of the findings that reduced tumor-infiltrating Tregs by mAb2-3-mediated depletion or blockade could enhance anti-tumor activity was confirmed. Mice bearing luciferase-expressing IGROV-1 xenografts received $4 \times 10^6$ TP-T cells and were treated with mAb2-3 twice a week for five weeks. Bioluminescent images were taken every ten days to quantitate the tumor size (FIG. 5A). Mice treated with mAb2-3 IgG1 and IgG4 showed lower relative low luminescence intensity compared to control groups, with mAb2-3 IgG1 treatment showing greater anti-tumor effects than mAb2-3 IgG4 (FIG. 5B). The same observation was seen in tumor size measurement (FIG. 5C). Interestingly, the greatest reduction in mouse body weight was seen in the group treated with mAb2-3 IgG1 (FIG. 5D). The anti-tumor effect of mAb2-3 was also observed in tumor tissue (FIG. 5E) and tumor weight (FIG. 5F). These results showed that mAb2-3 mediated TP-T cells against tumor inhibiting tumor growth in vivo.

To confirm the potent therapeutic effect of mAb2-3, we increased by 2.5-fold the number of TP-T cells injected into mice bearing IGROV-1 xenografts. Under these experimental conditions, there was statistically significant inhibition of the tumor growth curves in mice treated with both mAb2-3 IgG1 and IgG4 (FIG. 13A). The body weight and tumor tissues showed similar results as FIG. 5 (FIGS. 13B and 13C). TP-T cells ($CD3^+$) were found infiltrating the site of tumor engraftment for all treatment groups (FIG. 13G, upper panel). In addition, $CD25^+$ TP-T cells were detectable and accumulated in xenografted tumor treated with PBS and control mAb, but accumulation of $CD25^+$ TP-T cells reduced in tumor treated with mAb2-3 IgG1 and IgG4 (FIG. 13G, lower panel). The TP-T cells in mouse blood were further investigated by FACS and the results showed that there were no difference in $CD4^+$ and $CD8^+$ T cells among each treatment group but the Treg population was decreased only in mAb2-3 IgG1-treated group (FIGS. 13D-F). Taken together, these data indicate that Treg depletion by mAb2-3

IgG1 and tumor-recruiting Treg blockade by mAb2-3 IgG4 could enhance anti-tumor immunity in vivo.

Example 8: Mechanisms of Action of mAB2-3

Figure 14:
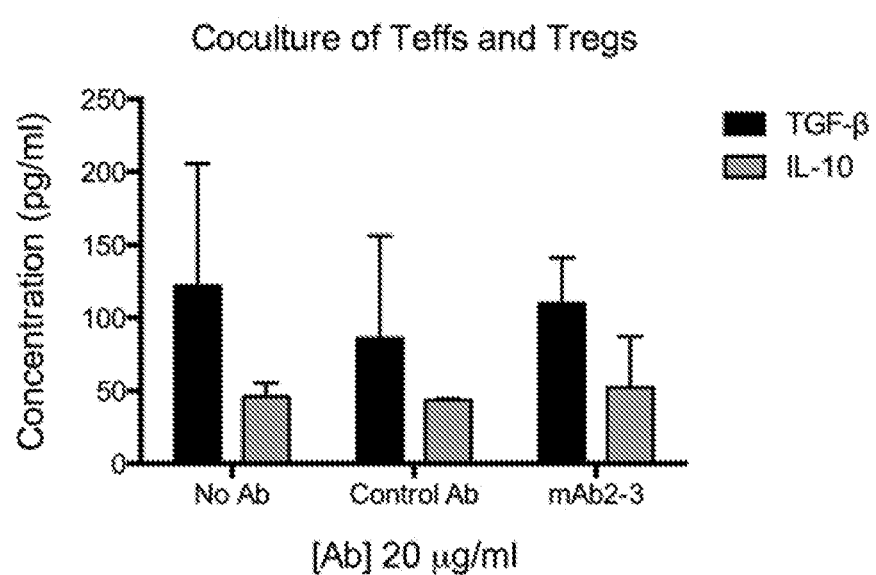
FIG. 14. Suppressive cytokine production by Tregs. Effect of antibody treatment on suppressive cytokine production by Tregs was evaluated using ELISA measurement of the IL-10 and TGF-β cytokines in the supernatants collected from cultures of non-treated, control mAb or mAb2-3 with $CD4^+$ $CD25^-$ and $CD4^+$ $CD25^+$ T cells. T cells cultured without mAbs were used as control for any detected background levels of IL-10 and TGF-β. Data are presented as mean±S.D.

The suppressive mechanisms used by Tregs include releasing inhibitory cytokines and cytolytic enzymes, as well as mediating metabolic disruption by CD25/IL-2 and CD3⁹/adenosine (21). Cytokine production by Tregs was studied and it was found that mAb2-3 did not alter the levels of suppressive cytokines, i.e. IL-10 and TGF-β (FIG. 14). Next it was determined if the binding of mAb2-3 to CCR4 on Teff and Treg could affect the interactions between CD25(TAC), the a chain of IL-2 receptor (IL-2R), and IL-2. FIG. 6A shows that endogenous IL-2 secretion from Teffs was not induced by mAb2-3 treatment. In contrast, when exogenous IL-2 was added into the Tregs culture, marked increase in IL-2 accumulation was detected in the supernatant with mAb2-3 only (FIG. 6B). In addition, a Teff/Treg co-culture system was set up in which cells were treated with mAb2-3 or control mAb and also incubated without (FIG. 6C) or with (FIG. 6D) exogenous IL-2. The results showed that mAb2-3 but not control mAb treatment lead to an increase in IL-2 levels in both co-culture supernatants.

Figure 15:
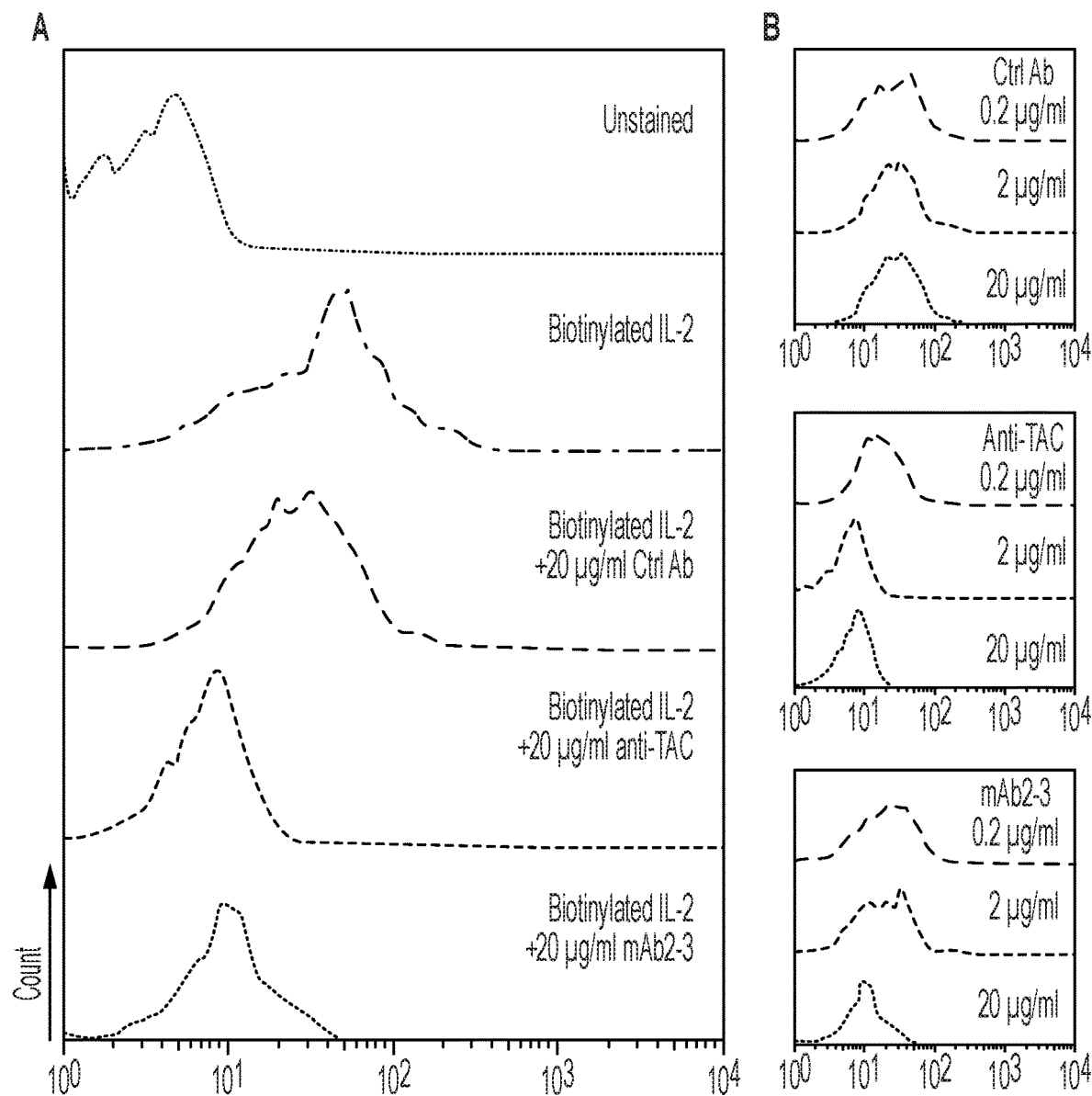
FIG. 15. Flow cytometry-based IL-2 binding and competition analyses. (A) Mac-1 cells were washed with cold PBS and then stained sequentially with 20 μg/ml or (B) three concentrations of competitive antibodies (mAb2-3, anti-TAC or control mAbs), 100 nM of biotinylated IL-2, and APC-labeled streptavidin. The binding of biotinylated IL-2 to Mac-1 cells was detected by flow cytometry.
Figure 16:
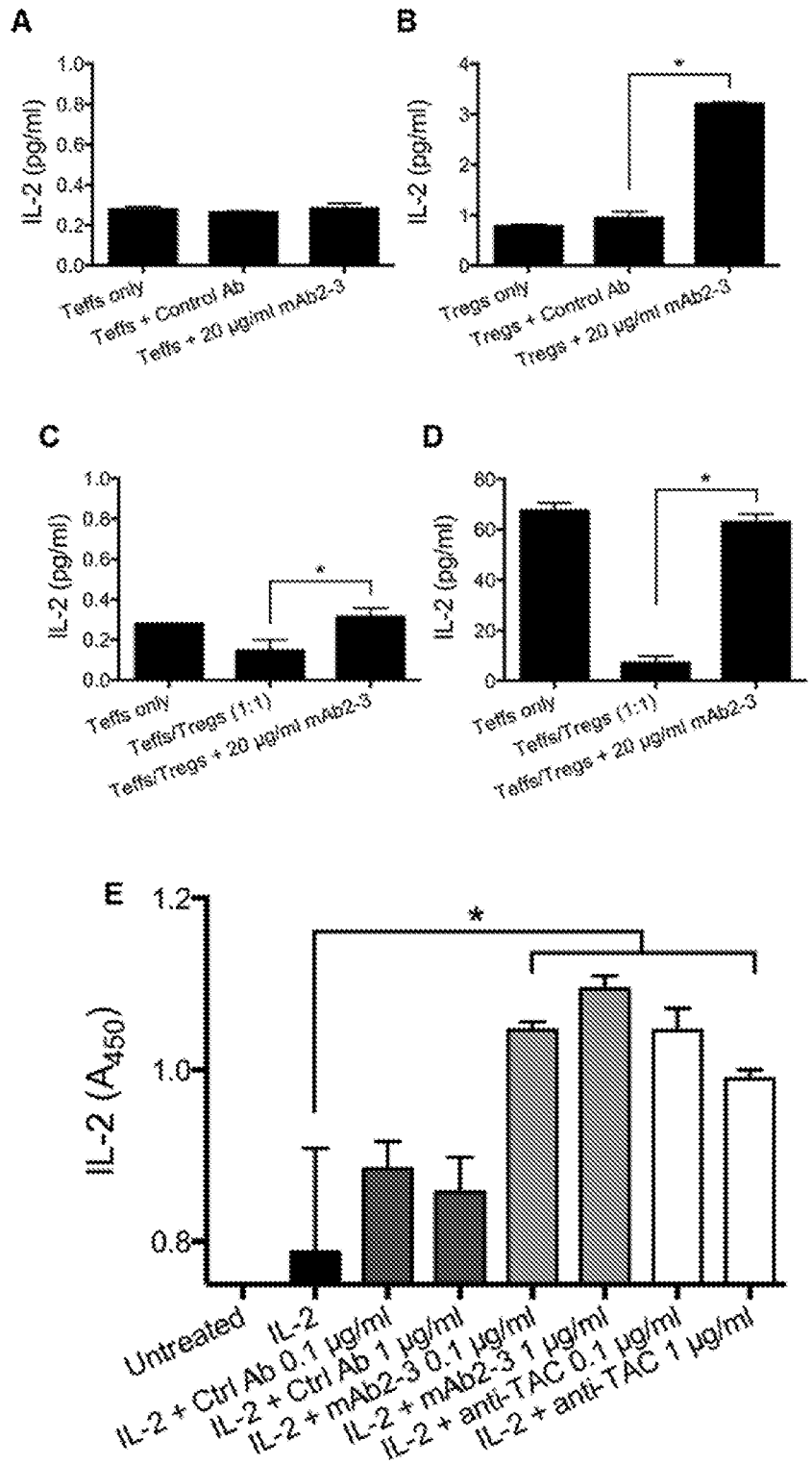
FIG. 16 Mechanisms of Actions of Ab2-3 on IL-2 binding The intermediation of mAb2-3 in the interaction between IL-2 and CD25. (A) In the absence of exogenous IL-2, endogenous IL-2 levels in $1 \times 10^4$ $CD4^+$ $CD25^-$ Teffs cultured supernatants incubated with or without mAb2-3 were analyzed by ELISA. (B) $CD4^+$ $CD127^{dim}CD49d^-$ Tregs (3000/reaction) were incubated with 0.25 IU/ml of exogenous IL-2 in the presence and absence of 20 μg/ml of mAbs and 0.5/1 μg/ml of plate-bound anti-CD3/28 antibodies. Bars represent ±S.D. (C) In the absence of exogenous IL-2, endogenous IL-2 concentration was shown from $1 \times 10^4$ Teffs alone or with Tregs and treated with 20 μg/ml of mAb2-3. Bars represent ±S.D. (D) The concentrations of IL-2 in supernatants from Teffs and Tregs coculture treated with mAb2-3 in the presence of 4 IU/ml of exogenously added IL-2. Bars represent ±S.D. (E) In the presence of exogenous IL-2 (20 IU/ml), the IL-2 concentrations of supernatants from $2 \times 10^5$ Mac-1 cells treated with or without antibodies (mAb2-3 or anti-CD25, including anti-TAC and control mAbs) were detected by ELISA. Bars represent ±S.D.

Mac-1 cells expressing both CCR4 and IL-2Rs were then used to further examine if mAb2-3 affected the binding of IL-2 to IL-2R in a competition assay. The results showed that like the anti-TAC (IL-2Rα) mAb, mAb2-3 effectively inhibited the binding of biotinylated-IL-2 to Mac-1 cells when compared to treatment with the control anti-CD25 mAb that does not block IL-2 binding (FIGS. 15A and 15B) (22). In addition, the Mac-1 culture supernatants were harvested following treatment with exogenous IL-2 and different mAbs, and subjected to ELISA assay for soluble IL-2 detection. Treatment with both anti-TAC mAb and mAb2-3 lead to increased IL-2 level in the culture supernatant presumably due to inhibition of exogenous IL-2 binding to Mac-1 cells, but control mAb-treated or untreated groups did not FIG. 6E.

It is known that IL-2Rs consists of three subunits, α, β, and γ chains, and the a chain markedly increases the affinity of the receptor to IL-2, from Kd=1 nM (βγ chains) to Kd=10 pM (αβγ chains). In control experiments with transiently transfected 293T cell, inhibition of IL-2 binding was found not to be due to direct binding of mAb2-3 to the individual α, β, and γ subunit chains or to the complex. CD25 is also reportedly cleaved to a soluble form (sCD25) (23) with Kd=30 nM following T cell activation (24). sCD25 in the culture supernatant following treatment with mAb2-3 or control mAb was monitored. The data demonstrated that level of sCD25 in the supernatant was increased when cells were treated with mAb2-3 in a dose dependent manner (FIG. 18A) and this effect was positively correlated with the time of incubation (FIGS. 17B-17D). This result suggested that mAb2-3 engagement of CCR4 resulted in T cell activation perhaps similarly to its ligands CCL17 and CCL22 (25,26). Indeed, both ligands also induced sCD25 shedding (FIG. 17A). To further determine the function of mAb2-3-mediated sCD25 shedding on Treg survival, Tregs were cultured with IL-2 and/or mAb2-3/control IgG1. IL-2 showed the capacity to maintain Treg survival, but interestingly, the positive effect of IL-2 on Treg survival was inhibited by mAb2-3 (FIG. 6F). These results demonstrate that mAb2-3 engagement of CCR4 on Tregs leads to modulation o the IL-2/IL-2R complex that can result in increased Treg death.

Since mAb2-3 can block CCL17/22 interaction with CCR4, we sought to understand whether CCL17/22 engagement of CCR4 might induce sCD25 shedding similarly to mAb2-3. FIG. 17A demonstrates that both CCL17 and CCL22 ligands showed the activity to induce sCD25 shedding which has not been previously reported.

Several studies have shown that matrix metalloproteinase 9 (MMP-9) possesses the capacity to cleave CD25 (27-29). To investigate the mechanisms of action of mAb2-3, CCL17, and CCL22 in inducing sCD25 shedding, the cultures were treated with MMP-9 inhibitor or control MMP inhibitor (FIG. 17A). Interestingly, the MMP-9 inhibitor reduced shedding of sCD25 in all treatment groups with no effect observed from the control inhibitor (FIG. 17A and FIGS. 18A-B). These results indicate that mAb2-3 treatment leads to the cleavage of CD25 in a similar manner as CCL22/17, suggesting that mAb2-3 possesses agonist activities and shares the capacity with the CCR4 ligands to activate MMP-9 function and sCD25 cleavage, with the end result being loss of IL-2 binding.

REFERENCES

1. Reznek R H. Cancer of the ovary. Cambridge, UK; New York: Cambridge University Press; 2007. xi, 176 p. p.
2. Agarwal R, Kaye S B. Ovarian cancer: strategies for overcoming resistance to chemotherapy. Nature reviews Cancer 2003; 3(7):502-16.
3. Disis M L, Rivkin S. Future directions in the management of ovarian cancer. Hematology/oncology clinics of North America 2003; 17(4):1075-85.
4. Duraiswamy J, Kaluza K M, Freeman G J, Coukos G. Dual blockade of PD-1 and CTLA-4 combined with tumor vaccine effectively restores T-cell rejection function in tumors. Cancer research 2013; 73(12):3591-603.
5. Hodi F S, Mihm M C, Soiffer R J, Haluska F G, Butler M, Seiden M V, et al. Biologic activity of cytotoxic T lymphocyte-associated antigen 4 antibody blockade in previously vaccinated metastatic melanoma and ovarian carcinoma patients. Proceedings of the National Academy of Sciences of the United States of America 2003; 100 (8):4712-7.
6. Soares K C, Rucki A A, Wu A A, Olino K, Xiao Q, Chai Y, et al. PD-1/PD-L1 blockade together with vaccine therapy facilitates effector T-cell infiltration into pancreatic tumors. Journal of immunotherapy 2015; 38(1):1-11.
7. Anagnostou V K, Brahmer J R. Cancer Immunotherapy: A Future Paradigm Shift in the Treatment of Non-Small Cell Lung Cancer. Clinical cancer research: an official journal of the American Association for Cancer Research 2015; 21(5):976-84.
8. Boon T, Cerottini J C, Van den Eynde B, van der Bruggen P, Van Pel A. Tumor antigens recognized by T lymphocytes. Annual review of immunology 1994; 12:337-65.
9. Sakaguchi S, Yamaguchi T, Nomura T, Ono M. Regulatory T cells and immune tolerance. Cell 2008; 133(5): 775-87.
10. Wood K J, Sakaguchi S. Regulatory T cells in transplantation tolerance. Nature reviews Immunology 2003; 3(3):199-210.
11. Valzasina B, Piconese S, Guiducci C, Colombo M P. Tumor-induced expansion of regulatory T cells by conversion of CD4+CD25− lymphocytes is thymus and proliferation independent. Cancer research 2006; 66(8): 4488-95.
12. Woo E Y, Chu C S, Goletz T J, Schlienger K, Yeh H, Coukos G, et al. Regulatory CD4(+)CD25(+) T cells in tumors from patients with early-stage non-small cell lung cancer and late-stage ovarian cancer. Cancer research 2001; 61(12):4766-72.
13. Curiel T J, Coukos G, Zou L, Alvarez X, Cheng P, Mottram P, et al. Specific recruitment of regulatory T cells in ovarian carcinoma fosters immune privilege and predicts reduced survival. Nature medicine 2004; 10(9):942-9.
14. Baecher-Allan C, Anderson D E. Regulatory cells and human cancer. Seminars in cancer biology 2006; 16(2): 98-105.
15. Wolf D, Wolf A M, Rumpold H, Fiegl H, Zeimet A G, Muller-Holzner E, et al. The expression of the regulatory T cell-specific forkhead box transcription factor FoxP3 is associated with poor prognosis in ovarian cancer. Clinical cancer research: an official journal of the American Association for Cancer Research 2005; 11(23):8326-31.
16. Preston C C, Maurer M J, Oberg A L, Visscher D W, Kalli K R, Hartmann L C, et al. The ratios of CD8+ T cells to CD4+CD25+ FOXP3+ and FOXP3-T cells correlate with poor clinical outcome in human serous ovarian cancer. PloS one 2013; 8(11):e80063.
17. Chang D K, Sui J, Geng S, Muvaffak A, Bai M, Fuhlbrigge R C, et al. Humanization of an anti-CCR4 antibody that kills cutaneous T-cell lymphoma cells and abrogates suppression by T-regulatory cells. Molecular cancer therapeutics 2012; 11(11):2451-61.
18. Fontenot J D, Gavin M A, Rudensky A Y. Foxp3 programs the development and function of CD4+CD25+ regulatory T cells. Nature immunology 2003; 4(4):330-6.
19. Bruhns P, Iannascoli B, England P, Mancardi D A, Fernandez N, Jorieux S, et al. Specificity and affinity of human Fcgamma receptors and their polymorphic variants for human IgG subclasses. Blood 2009; 113(16): 3716-25.
20. Vignali D A, Collison L W, Workman C J. How regulatory T cells work. Nat Rev Immunol 2008; 8(7):523-32.
21. Richardson R I, Sodroski J G, Waldmann T A, Marasco W A. Phenotypic knockout of the high-affinity human interleukin 2 receptor by intracellular single-chain antibodies against the alpha subunit of the receptor. Proceedings of the National Academy of Sciences of the United States of America 1995; 92(8):3137-41.
22. Sheu B C, Hsu S M, Ho F I N, Lien H C, Huang S C, Lin R H. A novel role of metalloproteinase in cancer-mediated immunosuppression. Cancer Res 2001; 61(1): 237-42.
23. Jacques Y, Le Mauff B, Boeffard F, Godard A, Soulillou J P. A soluble interleukin 2 receptor produced by a normal alloreactive human T cell clone binds interleukin 2 with low affinity. J Immunol 1987; 139(7):2308-16.
24. Cronshaw D G, Owen C, Brown Z, Ward S G. Activation of phosphoinositide 3-kinases by the CCR4 ligand macrophage-derived chemokine is a dispensable signal for T lymphocyte chemotaxis. Journal of immunology 2004; 172(12):7761-70.
25. Nakagawa M, Schmitz R, Xiao W, Goldman C K, Xu W, Yang Y, et al. Gain-of-function CCR4 mutations in adult T cell leukemia/lymphoma. The Journal of experimental medicine 2014; 211(13):2497-505.
26. Brusko T M, Wasserfall C H, Hulme M A, Cabrera R, Schatz D, Atkinson M A. Influence of membrane CD25 stability on T lymphocyte activity: implications for immunoregulation. PloS one 2009; 4(11):e7980.
27. De Paiva C S, Yoon K C, Pangelinan S B, Pham S, Puthenparambil L M, Chuang E Y, et al. Cleavage of functional IL-2 receptor alpha chain (CD25) from murine corneal and conjunctival epithelia by MMP-9. Journal of inflammation 2009; 6:31.
28. El Houda Agueznay N, Badoual C, Hans S, Gey A, Vingert B, Peyrard S, et al. Soluble interleukin-2 receptor and metalloproteinase-9 expression in head and neck cancer: prognostic value and analysis of their relationships. Clinical and experimental immunology 2007; 150 (1):114-23.
29. Mortier E, Bernard J, Plet A, Jacques Y. Natural, proteolytic release of a soluble form of human IL-15 receptor alpha-chain that behaves as a specific, high affinity IL-15 antagonist. J Immunol 2004; 173(3):1681-8.
30. Lanca T, Silva-Santos B. The split nature of tumor-infiltrating leukocytes: Implications for cancer surveillance and immunotherapy. Oncoimmunology 2012; 1(5): 717-25.
31. Zou W. Immunosuppressive networks in the tumour environment and their therapeutic relevance. Nature reviews Cancer 2005; 5(4):263-74.
32. Liyanage U K, Moore T T, Joo H G, Tanaka Y, Herrmann V, Doherty G, et al. Prevalence of regulatory T cells is increased in peripheral blood and tumor microenvironment of patients with pancreas or breast adenocarcinoma. Journal of immunology 2002; 169(5):2756-61.
33. Kudo-Saito C, Schlom J, Camphausen K, Coleman C N, Hodge J W. The requirement of multimodal therapy (vaccine, local tumor radiation, and reduction of suppressor cells) to eliminate established tumors. Clinical cancer research: an official journal of the American Association for Cancer Research 2005; 11(12):4533-44.
34. Mackensen A, Meidenbauer N, Vogl S, Laumer M, Berger J, Andreesen R. Phase I study of adoptive T-cell therapy using antigen-specific CD8+ T cells for the treatment of patients with metastatic melanoma. Journal of clinical oncology: official journal of the American Society of Clinical Oncology 2006; 24(31):5060-9.
35. Morse M A, Hobeika A C, Osada T, Serra D, Niedzwiecki D, Lyerly H K, et al. Depletion of human regulatory T cells specifically enhances antigen-specific immune responses to cancer vaccines. Blood 2008; 112 (3):610-8.
36. Curtin J F, Candolfi M, Fakhouri T M, Liu C, Alden A, Edwards M, et al. Treg depletion inhibits efficacy of cancer immunotherapy: implications for clinical trials. PloS one 2008; 3(4):e1983.
37. Dilek N, Poirier N, Hulin P, Coulon F, Mary C, Ville S, et al. Targeting CD28, CTLA-4 and PD-L1 costimulation differentially controls immune synapses and function of human regulatory and conventional T-cells. PloS one 2013; 8(12):e83139.
38. Simpson T R, Li F, Montalvo-Ortiz W, Sepulveda M A, Bergerhoff K, Arce F, et al. Fc-dependent depletion of tumor-infiltrating regulatory T cells co-defines the efficacy of anti-CTLA-4 therapy against melanoma. The Journal of experimental medicine 2013; 210(9):1695-710.
39. Hodi F S, Butler M, Oble D A, Seiden M V, Haluska F G, Kruse A, et al. Immunologic and clinical effects of antibody blockade of cytotoxic T lymphocyte-associated antigen 4 in previously vaccinated cancer patients. Proceedings of the National Academy of Sciences of the United States of America 2008; 105(8):3005-10.
40. Ansell S M, Lesokhin A M, Borrello I, Halwani A, Scott E C, Gutierrez M, et al. PD-1 blockade with nivolumab in relapsed or refractory Hodgkin's lymphoma. The New England journal of medicine 2015; 372(4):311-9.

41. Wolchok J D, Kluger H, Callahan M K, Postow M A, Rizvi N A, Lesokhin A M, et al. Nivolumab plus ipilimumab in advanced melanoma. The New England journal of medicine 2013; 369(2):122-33.
42. Swaika A, Hammond W A, Joseph R W. Current state of anti-PD-L1 and anti-PD-1 agents in cancer therapy. Molecular immunology 2015.
43. Han T, Abdel-Motal U M, Chang D K, Sui J, Muvaffak A, Campbell J, et al. Human anti-CCR4 minibody gene transfer for the treatment of cutaneous T-cell lymphoma. PloS one 2012; 7(9):e44455.
44. Nesspor T C, Raju T S, Chin C N, Vafa O, Brerski R J. Avidity confers FcgammaR binding and immune effector function to a glycosylated immunoglobulin G1. Journal of molecular recognition: JMR 2012; 25(3):147-54.
45. Moon E K, Wang L C, Dolfi D V, Wilson C B, Ranganathan R, Sun J, et al. Multifactorial T-cell hypofunction that is reversible can limit the efficacy of chimeric antigen receptor-transduced human T cells in solid tumors. Clinical cancer research: an official journal of the American Association for Cancer Research 2014; 20(16): 4262-73.
46. Lo AS-Y, Xu C, Murakami A, Marasco W A. Regression of established renal cell carcinoma in nude mice using lentivirus-transduced human T cells expressing a human anti-CAIX chimeric antigen receptor. Molecular Therapy—Oncolytics 2014; 1:14003.
47. Viney J M, Andrew D P, Phillips R M, Meiser A, Patel P, Lennartz-Walker M, et al. Distinct conformations of the chemokine receptor CCR4 with implications for its targeting in allergy. Journal of immunology 2014; 192(7): 3419-27.
48. Santulli-Marotto S, Boakye K, Lacy E, Wu S J, Luongo J, Kavalkovich K, et al. Engagement of two distinct binding domains on CCL17 is required for signaling through CCR4 and establishment of localized inflammatory conditions in the lung. PloS one 2013; 8(12):e81465.
49. Boyman O, Kovar M, Rubinstein M P, Surh C D, Sprent J. Selective stimulation of T cell subsets with antibody-cytokine immune complexes. Science 2006; 311(5769): 1924-7.
50. Lindqvist C A, Christiansson L H, Simonsson B, Enblad G, Olsson-Stromberg U, Loskog A S. T regulatory cells control T-cell proliferation partly by the release of soluble CD25 in patients with B-cell malignancies. Immunology 2010; 131(3):371-6.
51. Severson J J, Serracino H S, Mateescu V, Raeburn C D, McIntyre R C, Sams S B, et al. PD-1+Tim-3+ CD8+ T Lymphocytes Display Varied Degrees of Functional Exhaustion in Patients with Regionally Metastatic Differentiated Thyroid Cancer. Cancer immunology research 2015.
52. Choi S Y, Lin D, Gout P W, Collins C C, Xu Y, Wang Y. Lessons from patient-derived xenografts for better in vitro modeling of human cancer. Advanced drug delivery reviews 2014; 79-80:222-37.
53. Das R, Verma R, Sznol M, Boddupalli C S, Gettinger S N, Kluger H, et al. Combination therapy with anti-CTLA-4 and anti-PD-1 leads to distinct immunologic changes in vivo. Journal of immunology 2015; 194(3): 950-9.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A pharmaceutical composition comprising a humanized anti-CCR4 antibody in an amount effective to increase the ratio of effector T-cells to regulatory T-cells in or associated with a tumor present in a human subject to whom the pharmaceutical composition is administered one or more times, wherein the regulatory T-cells comprise $CD4^+$ $CD25^{highCD127dim/-}$ Tregs and the effector T-cells comprise $CD4^+$ $CD25^-$ Teffs, wherein the humanized anti-CCR4 antibody has a heavy chain with three CDRs comprising the amino acid sequences GYTFASAW (SEQ ID NO: 9), INPGNVNT (SEQ ID NO: 11), and STYYRPLDY (SEQ ID NO: 13) respectively and a light chain with three CDRs comprising the amino acid sequences QSILYSSNQKNY (SEQ ID NO: 10), WASTRE (SEQ ID NO: 12), and HQYMSSYT (SEQ ID NO: 14) respectively, and wherein the humanized anti-CCR4 antibody has an $IgG_4$ heavy chain constant region.

2. The pharmaceutical composition of claim 1, wherein the tumor is a solid tumor.

3. The pharmaceutical composition of claim 1, wherein the humanized anti-CCR4 IgG4 antibody is non-immunodepleting.

4. The pharmaceutical composition of claim 1, wherein the constant region comprises a S228P mutation.

* * * * *